United States Patent
Gagete Mateos et al.

(10) Patent No.: US 11,505,526 B2
(45) Date of Patent: Nov. 22, 2022

(54) ARYL-PIPERIDINE DERIVATIVES

(71) Applicant: Artax Biopharma Inc., Cambridge, MA (US)

(72) Inventors: Andrés Gagete Mateos, Valencia (ES); Damiá Tormo Carulla, Cambridge, MA (US); Luc Marti Clauzel, Cambridge, MA (US); Julio Castro Palomino, Barcelona (ES)

(73) Assignee: Artax Biopharma Inc., Cambridge, MA (US)

( * ) Notice: Subject to any disclaimer, the term of this patent is extended or adjusted under 35 U.S.C. 154(b) by 0 days.

(21) Appl. No.: 16/493,815

(22) PCT Filed: Mar. 14, 2018

(86) PCT No.: PCT/US2018/022357
§ 371 (c)(1),
(2) Date: Sep. 13, 2019

(87) PCT Pub. No.: WO2018/170078
PCT Pub. Date: Sep. 20, 2018

(65) Prior Publication Data
US 2020/0131125 A1    Apr. 30, 2020

(30) Foreign Application Priority Data
Mar. 14, 2017    (EP) .................... 17382128

(51) Int. Cl.
| C07D 211/32 | (2006.01) |
| C07D 211/56 | (2006.01) |
| C07D 401/06 | (2006.01) |
| C07D 417/06 | (2006.01) |
| A61P 37/00 | (2006.01) |
| A61P 39/02 | (2006.01) |
| A61P 37/02 | (2006.01) |

(52) U.S. Cl.
CPC ............ *C07D 211/32* (2013.01); *A61P 37/02* (2018.01); *C07D 211/56* (2013.01); *C07D 401/06* (2013.01); *C07D 417/06* (2013.01)

(58) Field of Classification Search
CPC .. C07D 211/32; C07D 211/56; C07D 401/06; C07D 417/06; A61P 37/02; A61P 37/00
USPC ...................................................... 546/245
See application file for complete search history.

(56) References Cited

U.S. PATENT DOCUMENTS

| 6,552,065 B2 | 4/2003 | Remiszewski et al. |
| 7,390,799 B2 | 6/2008 | Bruncko et al. |
| 8,138,347 B2 | 3/2012 | Knight et al. |
| 2009/0264414 A1* | 10/2009 | Andersen ............ C07D 487/08 514/217.11 |
| 2012/0149733 A1 | 6/2012 | Cherney et al. |

FOREIGN PATENT DOCUMENTS

| EP | 0416581 A1 | 3/1991 | |
| EP | 2123769 A1 | 11/2009 | |
| EP | 3375778 A1 | 9/2018 | |
| EP | 3595647 A1 | 1/2020 | |
| GB | 1276812 A | 6/1972 | |
| WO | 2001042246 A2 | 6/2001 | |
| WO | 2002088112 A1 | 11/2002 | |
| WO | 2003028459 A1 | 4/2003 | |
| WO | 2003063794 A2 | 8/2003 | |
| WO | 2004/002483 A1 | 1/2004 | |
| WO | WO-2004002483 A1 * | 1/2004 | ............ C07D 211/26 |
| WO | 2004019973 A1 | 3/2004 | |
| WO | 2004089925 A1 | 10/2004 | |
| WO | 2004106328 A1 | 12/2004 | |
| WO | 2005007623 A2 | 1/2005 | |
| WO | 2005044797 A1 | 5/2005 | |
| WO | 2005046685 A1 | 5/2005 | |
| WO | WO-2005046685 A1 * | 5/2005 | ............... A61P 9/12 |
| WO | 2005113554 A2 | 12/2005 | |
| WO | 2006078846 A1 | 7/2006 | |
| WO | 2006122806 A2 | 11/2006 | |
| WO | 2007016176 A2 | 2/2007 | |
| WO | 2007044729 A2 | 4/2007 | |
| WO | 2007053452 A1 | 5/2007 | |
| WO | 2007070514 A1 | 6/2007 | |
| WO | 2007084786 A1 | 7/2007 | |
| WO | 2007129161 A2 | 11/2007 | |
| WO | 2008039218 A2 | 4/2008 | |

(Continued)

OTHER PUBLICATIONS

Yuya Morita Application of Bioisosteres (Year: 2012).*
Susanna Nencetti et al. 3-[(Aryl)(4-fluorobenzyloxy)methyl]piperidine derivatives: high-affinity ligands for the serotonin transporter (Year: 2007).*
Zalucky, T. B., "Chemistry of some 3-Benzoylpiperidines." Journal of Pharmaceutical Sciences 54.5 (1965): 687-693.*
Al-Maghrabi et al., "Immunoglobulin and T-cell receptor gene rearrangement in Castleman's disease: molecular genetic analysis," Histopathology. 2006; 48(3):233-38.
Babbe et al., "Clonal expansions of CD8(+) T cells dominate the T cell infiltrate in active multiple sclerosis lesions as shown by micromanipulation and single cell polymerase chain reaction," J. Exp. Med. 2000; 192(3): 393-404.

(Continued)

*Primary Examiner* — John M Mauro
(74) *Attorney, Agent, or Firm* — Dechert LLP; Andrea L. C. Reid; Gang Wang

(57) ABSTRACT

An aryl-piperidine derivative of formula I, wherein the meaning of $R_3$, X, Cz, and Cy is that specified in the description, for use as inhibitors of T cells.

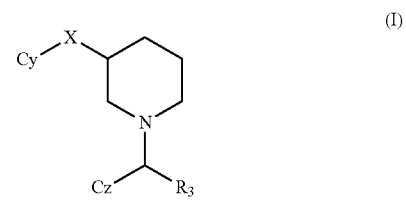

22 Claims, 3 Drawing Sheets

(56) References Cited

FOREIGN PATENT DOCUMENTS

| | | | |
|---|---|---|---|
| WO | 2008109943 | A1 | 9/2008 |
| WO | 2008118802 | A1 | 10/2008 |
| WO | 2009114512 | A1 | 9/2009 |
| WO | 2011035143 | A2 | 3/2011 |
| WO | 2011090760 | A1 | 7/2011 |
| WO | 2016073847 | A2 | 5/2016 |
| WO | 2018170078 | A1 | 9/2018 |

OTHER PUBLICATIONS

Bell et al., "Optimization of Novel Nipecotic Bis(amide) Inhibitors of the Rho/MKL1/SRF Transcriptional Pathway as Potential Anti-Metastasis Agents," Bioorg. Med. Chem. Lett. 2013; 23(13):3826-32.
Berge et al., "Pharmaceutical salts," J. Pharmaceutical Sciences. 1977; 66(1):1-19.
Caforio et al., "Genetically determined myocarditis: clinical presentation and immunological characteristics," Curr. Opin. Cardiol. 2008; 23(3):219-26.
Cai et al., "New insights of T cells in the pathogenesis of psoriasis," Cell Mol. Immunol. 2012; 9(4):302-09.
Cetkovic-Cvrlje et al., "Therapeutic potential of Janus kinase 3 (JAK3) inhibitors," Curr. Pharm. Des. 2004; 10(15):1767-84.
Cetkovic-Cvrlje et al., "Targeting Janus kinase 3 in the treatment of leukemia and inflammatory diseases," Arch. Immunol. Ther. Exp. 2004; 52(2):69-82.
Choy, "T cells in psoriatic arthritis," Curr. Rheumatol. Rep. Exp. 2007; 9(6):437-41.
Cobrin et al., "Defects in mucosal immunity leading to Crohn's disease," Immunol. Rev. 2005; 206(1):277-95.
Cope et al., "The central role of T cells in rheumatoid arthritis," Clin. Exp. Rheumatol. 2007; 25(5):S4-11.
Crispin et al., "Expanded double negative T cells in patients with systemic lupus erythematosus produce IL-17 and infiltrate the kidneys," J. Immunol. 2008; 181(12):8761-66.
Dai et al., "The T cell regulator gene SH2D2A contributes to the genetic susceptibility of multiple sclerosis," Genes Immun. 2001; 2(5):263-8.
Direskeneli, "Innate and Adaptive Responses to Heat Shock Proteins in Behcet's Disease," Genetics Research International. 2013; Article ID 249157, 6 Pages.
Evelyn et al., "Design, Synthesis and Prostate Cancer Cell-Based Studies of Analogs of the Rho/MKL1 Transcriptional Pathway Inhibitor, CCG-1423," Bioorg. Med. Chem. Lett. 2010; 20(2):665-72.
Fan et al., "Autoimmune pancreatitis," N. Am. J. Med. Sci. 2009; 1(2):148-51.
Finco et al., "Cytokine release assays: current practices and future directions," Cytokine. 2014; 66(2):143-55.
Fuller et al., "All roads lead to actin: the intimate relationship between TCR signaling and the cytoskeleton," Immunol. Rev. 2003; 292:220-36.
Gonzalez-Rey et al., "Therapeutic effect of vasoactive intestinal peptide on experimental autoimmune encephalomyelitis: down-regulation of inflammatory and autoimmune responses," Am. J. Pathol. 2006; 168(4):1179-88.
Greco et al., "Cogan's syndrome: An autoimmune inner ear disease," Autoimmunity Rev. 2013; 12(3):396-400.
Guida et al., "Clonal CD8+ TCR-Vbeta expanded populations with effector memory phenotype in Churg Strauss syndrome," Clin. Immunol. 2008; 128(1):94-102.
Hart et al., "Reaxys ID 31051130," Reed Elsevier Properties SA, 2017.
Holmdahl et al., "Collagen induced arthritis as an experimental model for rheumatoid arthritis. Immunogenetics, pathogenesis and autoimmunity," APMIS. 1989; 97(7): 575-84.

Horai et al., "Microbiota-Dependent Activation of an Autoreactive T Cell Receptor Provokes Autoimmunity in an Immunologically Privileged Site," Immunity. 2015; 43(2):343-53.
Hutchings et al., "Pharmacokinetic Optimitzation of CCG-203971: Novel Inhibitors of the Rho/MRTF/SRF Transcriptional Pathway as Potential Antifibrotic Therapeutics for Systemic Scleroderma," Bioorg. Med. Chem. Lett. 2017; 27(8):1744-1749.
Issa et al., "Role of T cells in graft rejection and transplantation tolerance," Expert Rev. Clin. Immunol. 2010; 6(1):155-69.
International Search Report and Written Opinion issued by the United States Patent Office as International Searching Authority for International Application No. PCT/US18/22357, dated Jun. 20, 2018 (12 Pages).
Irikura et al., "New Antiulcer Agents. 1. Syntheses and Biological Activities of 1-acyl-2-,-3-, and -4-substituted Benzamidopiperidines," J. Med. Chem. 1971; 14(4):357-61.
Kappeler et al., "The role of activated cytotoxic T cells in inflammatory bowel disease," Histol Histopathol. 2000; 15(1):167-72.
Kawaguchi et al., "Fluorescence Probe for Lysophospholipase C/NPP6 Activity and a Potent NPP6 Inhibitor," J. Am. Chem. Soc. 2011; 133(31):12021-30.
Kitazawa et al., "Immunization with amyloid-beta attenuates inclusion body myositis-like myopathology and motor impairment in a transgenic mouse model," J. Neuroscience. 2009; 29(19):6132-41.
Kudlacz et al., "The novel JAK-3 inhibitor CP-690550 is a potent immunosuppressive agent in various murine models," Am. J. Transplant. 2004; 4(1):51-7.
Linterman et al., "Follicular helper T cells are required for systemic autoimmunity," J. Exp. Med. 2009; 206(3):561-76.
Lyle et al., "The Syntheses of Potential Medicinal Agents From 1-methyl-3-bromo-3-piperidyl Phenyl Ketone," J. Med. Pharm. Chem. 1961; 3:597-610.
Manns et al., "Diagnosis and management of autoimmune hepatitis," Hepatology. 2010; 51(6):2193-213.
Marks et al., "Innate immunity in inflammatory bowel disease: a disease hypothesis," J Pathol. 2008; 214(2):260-66.
Mazzarella, "Effector and suppressor T cells in celiac disease," World J. Gastroenterol. 2015; 21(24):7349-56.
Meriggioli et al., "Autoimmune myasthenia gravis: emerging clinical and biological heterogeneity," Lancet Neurology. 2009; 8(5):475-90.
Morgan et al., "CD4+CD28-T cell expansion in granulomatosis with polyangiitis (Wegener's) is driven by latent cytomegalovirus infection and is associated with an increased risk of infection and mortality," Arthritis & Rheumatism. 2011; 63(7):2127-37.
Nograles et al., "IL-22-producing "T22" T cells account for upregulated IL-22 in atopic dermatitis despite reduced IL-17-producing TH17 T cells," J. Allergy Clin. Immunol. 2009; 123(6):1244-52.
Notturno et al., "Susceptibility to chronic inflammatory demyelinating polyradiculoneuropathy is associated to polymorphic GA repeat in the SH2D2A gene," J. Neuroimmunol. 2008; 197(2):124-7.
Onouchi et al., "ITPKC functional polymorphism associated with Kawasaki disease susceptibility and formation of coronary artery aneurysms," Nature Genetics. 2008; 40(1):35-42.
O'Sea et al., "A new modality for immunosuppression: targeting the JAK/STAT pathway," Nat. Rev. Drug Doscpv. 2004; 3(7):555-64.
Petukhova et al., "Genome-wide association study in alopecia areata implicates both innate and adaptive immunity," Nature. 2010; 466(7302):113-17.
Raveche et al., "Evidence of Borrelia autoimmunity-induced component of Lyme carditis and arthritis," J. Clin. Microbiol. 2005; 43(2):850-56.
Robinson, "The role of the T cell in asthma," J. Allergy Clin. Immunol. 2010; 126(6):1081-91.
Roche et al., "Sensitization to epithelial antigens in chronic mucosal inflammatory disease. Characterization of human intestinal mucosa-derived mononuclear cells reactive with purified epithelial cell-associated components in vitro," J. Clin. Invest. 1985; 75(2):522-530.
Roep, "The role of T-cells in the pathogenesis of Type 1 diabetes: From cause to cure," Diabetologia. 2003; 46(3):305-21.
Shlomchik, "Graft-versus-host disease," Nature Rev. Immunology. 2007; 7:340-52.

(56) References Cited

OTHER PUBLICATIONS

Silva et al., "Diagnosis and classification of autoimmune orchitis," Autoimmun Rev. 2014; 13(4-5):431-34.
Boivin et al., "A flexible, convergent approach to piperidines, pyridines, azepines, and related derivatives," Tetrahedron Letters. 1999; 40(19):3701-3704.
Germain et al., "Identification of small-molecule inhibitors of replication," Bioorganic & Medicinal Chemistry Letters. 2011; 21(23):7197-7200.
Nencetti et al., "3-[(aryl)(4-fluorobenzyloxy)methyl]piperidine derivatives: high-affinity ligands for the serotonin transporter," Pharmaceutical and Clinical Research. 2007; 59(10):1439-1445.
Orjales et al., "Syntheses and Binding Studies of New [(Aryl)(aryloxy)methyl]piperidine Derivatives and Related Compounds as Potential Antidepressant Drugs with High Affinity for Serotonin (5-HT) and Norepinephrine (NE) Transporters," Journal of Medicinal Chemistry. 2003; 46(25):5512-5532.
Remya et al., "An in silico approach for the identification of inhibitors against Acetylcholinesterase," Medicinal Chemistry Research. 2011; 21(10):2779-2787.
Singh et al., "Lyme borreliosis: from infection to autoimmunity," Paediatric Rheumatology. 2004; 10(7):598-614.
Smith, "Update on Ankylosing Spondylitis: Current Concepts in Pathogenesis," Curr Allergy Asthma Rep. 2015; 15(1):489.
Sneller et al., "Autoimmune lymphoproliferative syndrome," Curr. Opin. Rheumatology. 2003; 15(4):417-21.
Teachey et al., "Unmasking Evans syndrome: T-cell phenotype and apoptotic response reveal autoimmune lymphoproliferative syndrome (ALPS)," Blood. 2004; 105(6):2443-48.
Tse et al., "Suppression of allogeneic T-cell proliferation by human marrow stromal cells: implications in transplantation," Transplantation. 2003; 75(3):389-97.
Van den Wijngaard et al., "Local immune response in skin of generalized vitiligo patients. Destruction of melanocytes is associated with the prominent presence of CLA+ T cells at the perilesional site," Lab Invest. 2000; 80(8):1299-309.
Van Steijvoort et al., "Remote Functionalization: Palladium-Catalyzed C5(sp3)-H Arylation of 1-Boc-3-aminopiperidine through the Use of a Bidentate Directing Group," ACS Catal. 2016; 6(7): 4486-4490.
Zenewicz et al., "CD4 T-cell differentiation and inflammatory bowel disease," Trends Mol. Med. 2009; 15(5):199-207.
Extended European Search Report issued by the European Patent Office for European Patent Application No. 17382128 dated May 30, 2017 (16 pages).

* cited by examiner

ARYL-PIPERIDINE DERIVATIVES

The present invention relates to aryl-piperidine derivatives of formula I useful for the treatment and/or prevention of an autoimmune disease, a mast-cell mediated allergy, a rejection of an allotransplant or a xenotransplant of an organ or a tissue, a lymphoma or a T-cell leukaemia, through the inhibition of T cells. Moreover, the invention relates to a process for the preparation thereof, and to pharmaceutical compositions that comprise these compounds.

STATE OF THE ART

T cells are directly involved in the pathogenesis of autoimmune diseases (ADs), allergies, and diseases associated with abnormal performance of the immune system. T cells require three signals for their activation to take place, signal 1, derived from the T cell antigen receptors (TCR); signal 2, derived from co-stimulatory receptors, e.g. CD28 upon binding to its ligands on the antigen-presenting cells (APC); and signal 3, a signal derived from cytokine receptors responsible for T cells proliferation and differentiation. The mechanism of action of the currently-used immunosuppressant drugs is based on the inhibition of the activation of signals 2 or 3, and include drugs such as belatacept and basiliximab, reslizumab, etc., respectively. The drawback of acting on signals 2 and 3 is that these signals are not limited to the activation of T cells. This means that currently-used immunosuppressant drugs do not inhibit T cells in a specific manner, and therefore, present high toxicity. In contrast the TCR signal is limited to T cells. The T cell recognizes antigen peptides associated to the major histocompatibility complex, also known as MHC, (pMHC) through TCR. The TCR is formed by 6 subunits, 2 of which, namely, TCRα and TCRβ, are responsible for the recognition of the antigen peptide associated MHC; whereas the other 4 subunits (i.e. CD3γ, CD3δ, CD3ε and CD3ζ) are responsible for the transmission of signals to the T cell cytoplasm. One of the initial processes that takes place following ligation of the TCR by the MHC is activation of the src-family tyrosine kinases Lck and Fyn, which phosphorylate the tyrosines in the immunoreceptor tyrosine-based activation motifs (ITAM) of the CD3 subunits. These, in turn, become anchor sites for the Syk-family tyrosine kinases (ZAP70 and Syk). In addition, the TCR undergoes a conformational change that results in the direct recruitment of the Nck adaptor to a proline-rich sequence (PRS) of the CD3E subunit. This TCR-Nck interaction takes place between the PRS portion of CD3ε, and the amino-terminal SH3.1 domain of Nck. Therefore, Nck is necessary for the activation of T lymphocytes in response to stimulation of the TCR. The compounds of the present invention surprisingly act blocking the TCR-Nck interaction, and consequently the abnormal proliferation of T cells.

Autoimmune diseases and diseases associated with abnormal performance of the immune system, in general, such as mast-cells mediated allergies, lymphomas and rejection of allotransplants, are a diverse group of diseases whereby the adaptive immune system (in particular, through T cells) attacks the body's antigens. These diseases are extremely relevant, both from the social and the economic standpoint. The latest statistics indicate that between 3 and 5% of the population suffers from autoimmune diseases. This incidence, and the chronic nature of these diseases, represent a high cost for health systems.

State of the art document WO2005046685A1 discloses also aryl-piperidines derivatives, as well as their medical use. In particular, the therein disclosed compounds are used in the treatment of diseases mediated by the inhibition of 11-β-hydroxysteroid dehydrogenase type 1 enzyme (11βHSD1), hence, metabolic syndromes, such as diabetes type II and obesity.

Therefore, there is a need in the field to provide new compounds capable of blocking the TCR-Nck interaction, and consequently capable of inhibiting T cells abnormal activation/proliferation.

DESCRIPTION OF THE INVENTION

All terms as used herein, unless otherwise provided, shall be understood in their ordinary meaning as known in the art. Other more specific definitions for certain terms as used in the present application are as set forth below and are intended to apply uniformly throughout the description and claims unless an otherwise expressly set out definition provides a broader one.

Section I. A first aspect of the present invention relates to a compound of formula I:

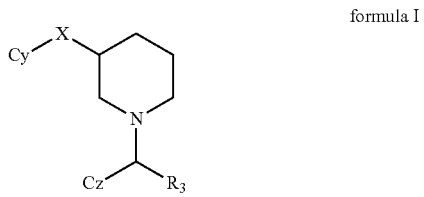

formula I or a pharmaceutically acceptable salt thereof, or a pharmaceutical composition that comprises the compound of formula I, or the pharmaceutically acceptable salt thereof and one or more pharmaceutically acceptable excipients, wherein:

Cz represents a phenyl group, a 5- or 6-membered aromatic heterocycle containing 1 or 2 heteroatoms selected from O, N and S at any available position on the ring, wherein Cz is optionally substituted with one or more $R_1$ groups;

each $R_1$ independently represents —H, halogen, —CN, —$OR_2$ or —$C_{1-4}$ alkyl, wherein $C_{1-4}$ alkyl is optionally substituted with one or more halogen groups;

each $R_2$ and $R'_2$ independently represents —H or —$C_{1-4}$ alkyl;

Cy represents a phenyl group, a 5- or 6-membered aromatic heterocycle containing 1 or 2 heteroatoms selected from O, N and S at any available position on the ring, wherein Cy is optionally substituted with one or more $R_1$ groups;

$R_3$ represents —H or =O;

X represents —CO—, —C(OH)—, —C($OR_4$)—, —C($NR_5R'_5$)—, —N($R_2$)—CO—, —CO—N($R_2$)— or —C(H$C_w$)—;

$C_w$ represents a 5- or 6-membered saturated or unsaturated heterocycle containing 1 or 2 N at any available position on the ring;

$R_4$ represents —$C_{1-4}$ alkyl, optionally substituted with halogen, —$OR_2$, —$NR_2R'_2$ or —$C_{1-4}$ alkyl-C'y;

each C'y independently represents a phenyl group, a 5- or 6-membered aromatic heterocycle containing 1 or 2 heteroatoms selected from O, N and S at any available position on the ring, wherein C'y is optionally substituted with one or more $R_1$ groups; and $R_5$ and $R'_5$ independently represent —H, —$C_{1-4}$ alkyl or —$C_{1-4}$ alkyl-C'y; for use in the prevention and/or treatment of a disease associated with an abnormal activation of T cells.

In a particular embodiment, the invention relates to the compound of formula I, or the pharmaceutically acceptable salt thereof, or the pharmaceutical composition, for use as previously defined, wherein the disease associated with an abnormal activation of T cells is selected from the group consisting of: an autoimmune disease, a mast-cell mediated allergy, a rejection of an allotransplant or a xenotransplant of an organ or a tissue, a lymphoma and a T-cell leukaemia.

In a particular embodiment, the invention relates to the compound of formula I, or the pharmaceutically acceptable salt thereof, or the pharmaceutical composition, for use as previously defined, wherein the autoimmune disease is selected from the group consisting of: rheumatoid arthritis, vitiligo, autoimmune hepatitis, myasthenia gravis, ankylosing spondylitis, inflammatory bowel disease, Crohn's disease, ulcerative colitis, psoriatic arthritis, transplant rejection, psoriasis, type I diabetes, multiple sclerosis, systemic lupus erythematosus, asthma, uveitis and atopic dermatitis.

Alternatively, the invention relates to the use of a compound of formula I as previously defined, or a pharmaceutically acceptable salt thereof, or a pharmaceutical composition that comprises the compound of formula I and one or more pharmaceutically acceptable excipients, for the preparation or manufacture of a medicament for the prevention and/or treatment of a disease associated with an abnormal activation of T cells. Alternatively, the invention relates to a method for the prevention and/or treatment of a disease associated with an abnormal activation of T cells comprising administering a compound of formula I as previously defined, or a pharmaceutically acceptable salt thereof, or a pharmaceutical composition that comprises the compound of formula I and one or more pharmaceutically acceptable excipients.

In a particular embodiment, the invention relates to the compound of formula I, or the pharmaceutically acceptable salt thereof, or the pharmaceutical composition, for use as previously defined, wherein Cy represents a phenyl group, optionally substituted with one or more $R_1$ groups.

In a particular embodiment, the invention relates to the compound of formula I, or the pharmaceutically acceptable salt thereof, or the pharmaceutical composition, for use as previously defined, wherein Cy represents a 5- or 6-membered aromatic heterocycle containing 1 or 2 heteroatoms selected from N, O and S at any available position on the ring, and wherein Cy is optionally substituted with one or more $R_1$ groups.

In another particular embodiment, the invention relates to the compound of formula I, or the pharmaceutically acceptable salt thereof, or the pharmaceutical composition, for use as previously defined, wherein Cy is substituted with two $R_1$ groups.

In another particular embodiment, the invention relates to the compound of formula I, or the pharmaceutically acceptable salt thereof, or the pharmaceutical composition, for use as previously defined, wherein the two $R_1$ groups of Cy represent —H.

In a particular embodiment, the invention relates to the compound of formula I, or the pharmaceutically acceptable salt thereof, or the pharmaceutical composition, for use as previously defined, wherein the two $R_1$ groups of Cy independently represent —H, halogen, —CN, —$OC_{1-4}$ alkyl or —$C_{1-4}$ alkyl.

In another particular embodiment, the invention relates to the compound of formula I, or the pharmaceutically acceptable salt thereof, or the pharmaceutical composition, for use as previously defined, wherein Cz represents a phenyl group, optionally substituted with one or more $R_1$ groups.

In another particular embodiment, the invention relates to the compound of formula I, or the pharmaceutically acceptable salt thereof, or the pharmaceutical composition, for use as previously defined, wherein Cz represents a 5- or 6-membered aromatic heterocycle containing one or two heteroatoms selected from N, O and S at any available position on the ring, optionally substituted with one or more $R_1$ groups.

In another particular embodiment, the invention relates to the compound of formula I, or the pharmaceutically acceptable salt thereof, or the pharmaceutical composition, for use as previously defined, wherein Cz is substituted with two $R_1$ groups.

In a particular embodiment, the invention relates to the compound of formula I, or the pharmaceutically acceptable salt thereof, or the pharmaceutical composition, for use as previously defined, wherein the two $R_1$ groups of Cz represent —H.

In a particular embodiment, the invention relates to the compound of formula I, or the pharmaceutically acceptable salt thereof, or the pharmaceutical composition, for use as previously defined, wherein the two $R_1$ groups are independently selected from —H, halogen, —CN, —$O_{C1-4}$ alkyl or —$C_{1-4}$ alkyl.

In a particular embodiment, the invention relates to the compound of formula I, or the pharmaceutically acceptable salt thereof, or the pharmaceutical composition, for use as previously defined, wherein X represents —CO—, —C(OH), or —N($R_2$)—CO—.

In a particular embodiment, the invention relates to the compound of formula I, or the pharmaceutically acceptable salt thereof, or the pharmaceutical composition, for use as previously defined, wherein X represents —CO— or —C(OH).

In a particular embodiment, the invention relates to the compound of formula I, or the pharmaceutically acceptable salt thereof, or the pharmaceutical composition, for use as previously defined, wherein $R_3$ represents =O.

In a particular embodiment, the invention relates to the compound of formula I, or the pharmaceutically acceptable salt thereof, or the pharmaceutical composition, for use as previously defined, wherein $R_3$ represents —H.

In another embodiment, the invention relates to the compound of formula I, or the pharmaceutically acceptable salt thereof, or the pharmaceutical composition, for use as previously defined, selected from:

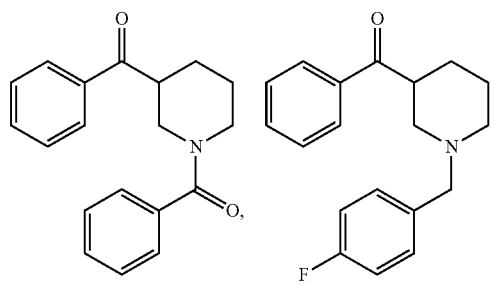

-continued

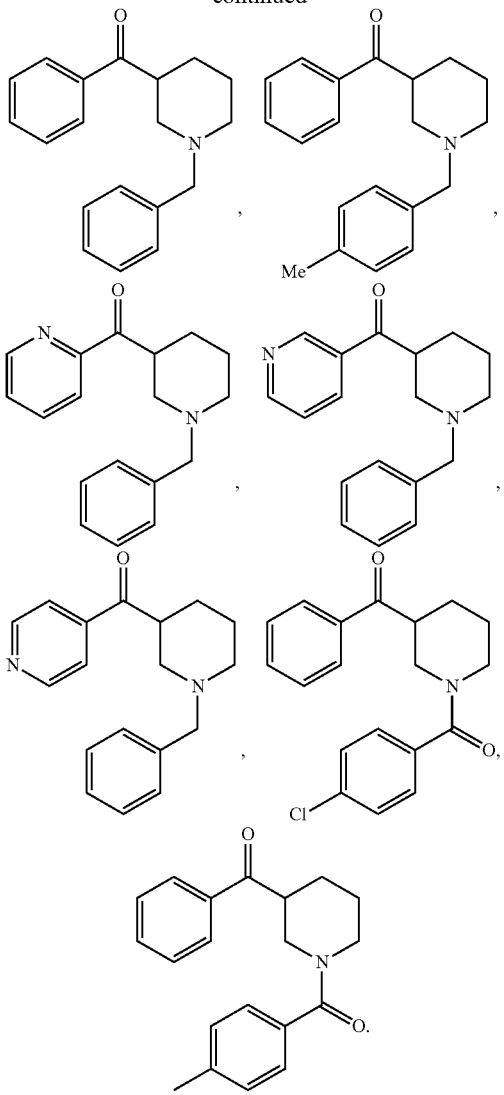

The invention also relates to all possible combinations of the above aspect and particular embodiments of the invention.

Section II. Another aspect of the invention relates to a compound of formula I:

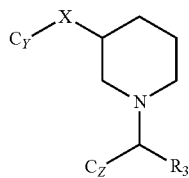

or a pharmaceutically acceptable salt thereof, wherein:

Cz represents a phenyl group, a 5- or 6-membered aromatic heterocycle containing 1 or 2 heteroatoms selected from O, N and S at any available position on the ring, wherein Cz is optionally substituted with one or more $R_1$ groups; each $R_1$ independently represents —H, halogen, —CN, —$OR_2$ or —$C_{1-4}$ alkyl, wherein —$C_{1-4}$ alkyl is optionally substituted with one or more halogen groups; each $R_2$ and $R'_2$ independently represents —H or —$C_{1-4}$ alkyl;

Cy represents a phenyl group, a 5- or 6-membered aromatic heterocycle containing 1 or 2 heteroatoms selected from O, N and S at any available position on the ring, wherein Cy is optionally substituted with one or more $R_1$ groups;

$R_3$ represents =O;

X represents —C(OH)— or —C($OR_4$)—;

$R_4$, represents —$C_{1-4}$ alkyl, optionally substituted with halogen, —$OR_2$, —$NR_2R'_2$ or —$C_{1-4}$ alkyl-C'y; and C'y represents a phenyl group, a 5- or 6-membered aromatic heterocycle containing 1 or 2 heteroatoms selected from O, N and S at any available position on the ring, wherein C'y is optionally substituted with one or more $R_1$ groups;

with the condition that the compound of formula I is not methanone, (5-bromo-2-thienyl)[(3R)-3-[(R)-(4fluorophenyl)hydroxymethyl]-1-piperidinyl].

In another particular embodiment, the invention relates to the compound of formula I, or the pharmaceutically acceptable salt thereof, as defined in Section II, wherein X represents —C(OH)—.

In another particular embodiment, the invention relates to the compound of formula I, or the pharmaceutically acceptable salt thereof, as defined in Section II, wherein Cy and Cz independently represent a phenyl group, optionally substituted with one or two $R_1$ groups.

In another particular embodiment, the invention relates to a compound of formula II, or a pharmaceutically active salt thereof:

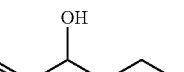

formula II

In another particular embodiment, the invention relates to a pharmaceutical composition that comprises the compound of formula I as defined in Section II, or the pharmaceutical acceptable salt thereof, or the compound of formula II, or the pharmaceutically acceptable salt thereof, and one or more pharmaceutically acceptable excipients.

Another aspect of the present invention relates to the compound of formula I, as defined in Section II, or the pharmaceutical acceptable salt thereof, or the pharmaceutical composition, or the compound of formula II, or the pharmaceutically acceptable salt thereof, or the pharmaceutical composition, for use as a medicament.

Another aspect of the present invention relates to the compound of formula I, as defined in Section II, or the pharmaceutical acceptable salt thereof, or the pharmaceutical composition, or the compound of formula II, or the pharmaceutically acceptable salt thereof, or the pharmaceutical composition, for use in the treatment and/or prevention of a disease associated with an abnormal activation of T cells.

In another embodiment, the disease associated with an abnormal activation of T cells is selected from the group consisting of: an autoimmune disease, a mast-cell mediated allergy, a rejection of an allotransplant or a xenotransplant of an organ or a tissue, a lymphoma and a T-cell leukaemia. In another embodiment, the autoimmune disease is selected from the group consisting of: rheumatoid arthritis, vitiligo, autoimmune hepatitis, myasthenia gravis, ankylosing spondylitis, inflammatory bowel disease, Crohn's disease, ulcerative colitis, psoriatic arthritis, transplant rejection, psoriasis, type I diabetes, multiple sclerosis, systemic lupus erythematosus, asthma, uveitis and atopic dermatitis.

Alternatively, the invention relates to the use of a compound, or a pharmaceutical acceptable salt thereof, or a pharmaceutical composition, any of them as defined in Section II, for the preparation or manufacture of a medicament. Alternatively, the invention relates to the use of a compound, or a pharmaceutical acceptable salt thereof, or a pharmaceutical composition, any of them as defined in Section II, for the preparation or manufacture of a medicament for the treatment and/or prevention of a disease associated with an abnormal activation of T cells. Alternatively, the invention relates to a method for preventing and/or treating a disease associated with an abnormal activation of T cells comprising administering a compound, or a pharmaceutical acceptable salt thereof, or a pharmaceutical composition, any of them as defined in Section II.

Another aspect of the present invention relates to a process for preparing compounds of formula I of Section II, wherein the process comprises:

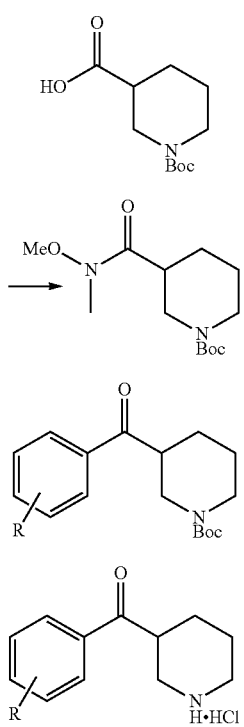

(1) reacting piperidine-1,3-dicarboxylic acid 1-tert-butyl ester of formula 1 with N,O-dimethylhydroxylamine to obtain the corresponding 3-(Methoxy-methyl-carbamoyl)-piperidine-1-carboxylic acid tert-butyl ester of formula 2; (2) reaction of the compound obtained in step (1) with the corresponding substituted benzyl halide under basic conditions to provide the corresponding 3-Benzoyl-piperidine-1-carboxylic acid tert-butyl ester of formula 3; (3) deprotection of the compound obtained in step (3) to yield substituted phenyl-piperidin-3-yl-methanone of formula 4; (4) reacting the compound obtained in step (3) with the corresponding substituted benzyl and benzoyl halide under basic conditions; and (5) reducing the compound obtained in step (4) using sodium borohydride.

The invention also relates to all possible combinations of the above aspects and particular embodiments of the invention.

Section III. In all the preceding definitions, the term $C_{1-4}$ alkyl, as a group or a part of a group, means a linear- or branched-chain alkyl group containing between 1 and 4 C atoms, and includes the methyl, ethyl, propyl, isopropyl, butyl, isobutyl, sec-butyl and tert-butyl groups.

A halogen radical, or its abbreviation "halo", means fluorine, chlorine, bromine or iodine.

"=O" or "—CO—" refers to the binding of an oxygen to an available carbon in the molecule by means of a double bond to form a carbonyl group.

"—C(OH)—" refers to the binding of an —OH group to the carbon by means of a single bond to form a hydroxyl group.

"—C(OR$_4$)—" refers to the binding of an —OR$_4$ group to the carbon by means of a single bond to form an alkoxyl group.

"—C(NR$_5$R'$_5$)—" refers to the binding of —R$_5$ and —R'$_5$ groups to the carbon by means of a single bond to form an amine.

"—N(R$_2$)—CO—" and "—CO—N(R$_2$)—" refer to amide groups.

"—C(HC$_w$)—" refers to the binding of —H and —C$_w$ groups to the carbon by means of a single bond.

The expression "optionally substituted with one or more" as used herein means the possibility of a group being substituted with one or more substituents. In a particular embodiment of the invention, with 1, 2, 3 or 4 substituents. In another particular embodiment, with 1, 2 or 3 substituents. In another particular embodiment, with 1 or 2 substituents, provided that said group has sufficient available positions susceptible to being substituted. If they are present, said substituents may be identical or different, and may be located at any available position.

Throughout the present description, the terms "treatment" and "treating" as used herein refer to the elimination, reduction or decrease of the cause or the effects of a disease. For purposes of this invention, "treatment" and "treating" includes, without being limited thereto, alleviating, reducing or eliminating one or more symptoms of the disease, reducing the grade of the disease, stabilising (i.e. not worsening) the state of the disease, delaying or slowing the progression of the disease, alleviating or improving the state of the disease, and remission (whether total or partial) of the disease.

As used in the present invention, the terms "prevention", "preventing" and "prevent" refer to the administration of a compound, or a pharmaceutically acceptable salt thereof, or a pharmaceutical composition according to the invention to a subject who has not been diagnosed as possibly having the disease at the time of the administration. Prevention also includes avoiding the reappearance of the disease in a subject who has previously suffered said disease. The prevention may be complete or partial.

The terms "subject", "individual", "animal" and "patient" include any subject, particularly a mammalian subject, for whom therapy and/or prevention is desired. Mammalian subjects include humans, domestic animals, farm animals, and zoo or pet animals. In a particular embodiment of the invention, the subject is a mammal. In a more particular embodiment, the subject is a human, preferably a human of any race and sex.

In another embodiment, the invention relates to the compounds of formula I that produce inhibition of T cells proliferation in a T cells inhibition assay such as the one described in the activity example.

The compounds of the present invention contain one or more basic nitrogens and, therefore, may form salts by reacting with acids, both organic and inorganic. Examples of said salts include without limitation: salts of inorganic acids, such as hydrochloric acid, hydrobromic acid, hydriodic acid, nitric acid, perchloric acid, sulfuric acid or phosphoric acid; and salts of organic acids, such as methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, citric acid, lactic acid, tartaric acid, malonic acid, glycolic acid, succinic acid and propionic acid, amongst others. Some compounds of the present invention may contain one or more acidic protons and, therefore, may also form salts by reacting with bases. Examples of said salts include, without limitation: salts of inorganic cations, such as sodium, potassium, calcium, magnesium, lithium, aluminium, zinc, etc.; and salts formed with pharmaceutically acceptable amines, such as ammonia, alkylamines, hydroxyalkylamines, lysine, arginine, N-methylglucamine, procaine and similar ones.

There are no limitations as to the types of salts that may be used, provided that they are pharmaceutically acceptable to be used for therapeutic purposes. Pharmaceutically acceptable salts are understood to mean those salts which, according to medical criteria, are adequate to be used in contact with human beings' or other mammals' tissues without causing undue toxicity, irritation, allergic responses or similar effects. Pharmaceutically acceptable salts are widely known to a person skilled in the art.

The salts of a compound of the invention may be obtained during the final isolation and purification of the compounds of the invention or be prepared by treating a compound of the invention with a sufficient quantity of the desired acid or base to produce the salt in a conventional manner. The salts of compounds of the invention may, in turn, be converted into other salts by means of ion-exchange using an ion-exchange resin.

The compounds of the invention and the salts thereof may differ in terms of certain physical properties, but, for purposes of the invention, are equivalent. All the salts of compounds of the invention are included within the scope of the invention.

The compounds of the present invention may form complexes with solvents with which they are made to react or from which they are precipitated or crystallised. These complexes are known as solvates. As used herein, the term "solvate" refers to a complex of variable stoichiometry formed by a solute (a compound of the invention or a salt thereof) and a solvent. Examples of solvents include pharmaceutically acceptable solvents such as, without limitation, water, ethanol and similar ones. A complex formed by water is known as a hydrate. Solvates of the compounds of the invention (or the salts thereof), including hydrates, are included within the scope of the invention.

The compounds of the invention may exist in different physical forms, i.e. in amorphous form and in crystalline forms. Moreover, the compounds of the present invention may be capable of crystallising in more than one form, a characteristic known as polymorphism. Polymorphs may differ in some physical properties widely known to persons skilled in the art, such as, for example, X-ray diffractograms, melting points or solubility. All the physical forms of the compounds of the invention, including all the polymorphic forms thereof ("polymorphs"), are included within the scope of the present invention.

Some compounds of the present invention may exist in the form of several diastereoisomers and/or several optical isomers. Diastereoisomers may be separated by means of conventional techniques, such as fractional chromatography or crystallisation. Optical isomers may be resolved by means of conventional optical resolution techniques, to produce optically pure isomers. This resolution may be performed on chiral synthesis intermediate compounds or on the compounds of the invention. The optically pure isomers may also be individually obtained using enantiospecific syntheses. The present invention includes both individual isomers and mixtures thereof (for example, racemic mixtures or mixtures of diastereoisomers), whether obtained by means of synthesis or by physical mixing. The compounds of formula I wherein X is a ketone have two enantiomers. Similarly, the compounds of formula I wherein X is an —OH have 2 diastereoisomers. We described the detailed synthesis of such compounds, each of them representing a racemic mixture of 2 enantiomers, i.e. the 2 diasteroisomers VII-1-01 and VII-1-02, or VII-2-01 and VII-2-02.

The present invention also relates to a pharmaceutical composition that comprises a compound of the invention (or a pharmaceutically acceptable salt or solvate thereof) and one or more pharmaceutically acceptable excipients. The excipients must be "acceptable" in the sense of being compatible with the remaining ingredients of the composition and not be harmful for those taking said composition.

The compounds of the present invention may be administered in the form of any pharmaceutical formulation, the nature whereof, as is well known, will be dependent on the nature of the active principle and its administration route. In principle, any administration route may be used, for example, oral, parenteral, nasal, ocular, rectal, and topical.

Solid compositions for oral administration include tablets, granules and capsules. In any case, the manufacturing method will be based on simple mixing, dry granulation or wet granulation of the active principle with excipients. These excipients may be, for example, diluents such as lactose, microcrystalline cellulose, mannitol or calcium hydrogen phosphate; binding agents such as, for example, starch, gelatine or polyvinylpyrrolidone; disaggregating agents such as sodium carboxymethyl starch or sodium croscarmellose; and lubricating agents such as, for example, magnesium stearate, stearic acid or talc. The tablets may further be coated with adequate excipients by means of known techniques, in order to delay the disaggregation and absorption thereof in the gastrointestinal tract, and thus achieve a sustained action over a longer period of time, or simply improve their organoleptic properties or their stability. The active principle may also be incorporated by coating inert pellets using natural or synthetic filmogenic polymers. It is also possible to manufacture soft gelatine capsules, wherein the active principle is mixed with water or with an oily medium, such as, for example, coconut oil, liquid paraffin or olive oil.

Powders and granules may be obtained in order to prepare oral 10 suspensions by adding water, mixing the active principle with dispersing or wetting agents, suspending agents and preservatives. Other excipients may also be added, for example, sweetening, flavouring and colouring agents.

Liquid forms for oral administration may include emulsions, solutions, suspensions, syrups and elixirs that contain commonly used inert diluents, such as distilled water, ethanol, sorbitol, glycerol, polyethylene glycols (macrogols) and propylene glycol. Said compositions may also contain adjuvants, such as wetting, suspending, sweetening and flavouring agents, preservatives and pH regulators.

According the present invention, injectable preparations, for parenteral administration, comprise sterile solutions, suspensions or emulsions, in an aqueous or non-aqueous solvent, such as propylene glycol, polyethylene glycol or vegetable oils. These compositions may also contain adjuvants, such as wetting, emulsifying and dispersing agents, and preservatives. They may be sterilised by means of any commonly known method or prepared as sterile solid compositions that are subsequently dissolved in water or any other sterile injectable medium immediately prior to use. It is also possible to start from sterile raw materials and keep them under these conditions during the entire manufacturing process.

For rectal administration, the active principle may be preferably formulated as suppositories on oily bases, such as, for example, vegetable oils or semi-synthetic solid glycerides, or on hydrophilic bases, such as polyethylene glycols (macrogols).

The compounds of the invention may also be formulated for topical application, for the treatment of pathologies that affect areas or organs that are accessible by said route, such as the eyes, the skin and the intestinal tract. These formulations include creams, lotions, gels, powders, solutions and patches wherein the compound is dispersed or dissolved in adequate excipients.

For nasal administration or inhalation, the compound may be formulated in the form of an aerosol, wherefrom it is conveniently released using adequate propellants.

The appropriate dosage as well as the dosing frequency of the compounds of the invention, or the salts thereof, within the pharmaceutical composition will depend on the nature of the disease to be treated or prevented, the severity and the course of the disease, the subject's age, gender, general condition and weight, whether the composition is administered for preventive or therapeutic purposes, among other factors. The amount of the compound of the invention, or salt thereof, or the pharmaceutical composition is administered to the subject at one time or over a series of treatments. Depending on the type and severity of the disease, an appropriate dosage level will generally be about 0.01 to 1,000 mg per kg patient body weight per day which can be administered in single or multiple doses. Preferably, the dosage level will be about 0.1 to about 500 mg/kg per day; more preferably about 0.25 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. For oral administration, the composition is preferably provided in the form of tablets, containing about 1.0 to about 1,000 mg of active compound, particularly at least about 1.0, at least about 5.0, at least about 10.0, at least about 15.0, at least about 20.0, at least about 25.0, at least about 50.0, at least about 75.0, at least about 100.0, at least about 150.0, at least about 200.0, at least about 250.0, at least about 300.0, at least about 400.0, at least about 500.0, at least about 600.0, at least about 750.0, at least about 800.0, at least about 900.0 or at least about 1000.0 mg. The compound, salt thereof, or pharmaceutical composition may be administered on a regime of 1 to 4 times per day, preferably one or twice per day.

The compounds of this invention may be prepared by means of the processes described below. In order to facilitate the description of the processes, we have used specific examples, which do not in any way limit the scope of the present invention.

Throughout the description and claims, the word "comprises" and variants thereof are not intended to exclude other technical features, additives, components or steps. Additional objects, advantages and features of the invention will become apparent to those skilled in the art upon examination of the description or may be learned by practice of the invention. The following examples are provided for illustrative purposes, and are not intended to limit the scope of the present invention. Furthermore, the present invention covers all possible combinations of particular embodiments.

Certain Embodiments of the Invention

As described herein, compounds of the present invention, and pharmaceutically acceptable salt thereof, are capable of inhibiting the TCR-Nck interaction, and T cell abnormal activation/proliferation. Compounds of the present invention, and pharmaceutically acceptable salts and compositions thereof, are useful for treating a variety of diseases, disorders or conditions as described herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

I. Compounds

In some embodiments, the present invention provides a compound of formula (III):

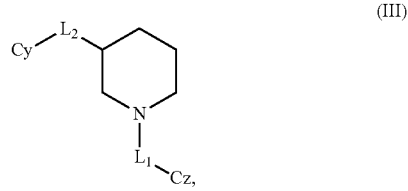

(III)

or a pharmaceutically acceptable salt thereof, wherein:

Cy is phenyl, or a 5- or 6-membered aromatic heterocycle containing 1 or 2 heteroatoms selected from O, N and S at any available position on the ring, wherein Cy is optionally substituted with one or more $R_1$ groups;

Cz is phenyl, or a 5- or 6-membered aromatic heterocycle containing 1 or 2 heteroatoms selected from O, N and S at any available position on the ring, wherein Cz is optionally substituted with one or more $R_1$ groups;

each $R_1$ independently represents —H, halogen, —CN, —OR$_2$, or —C$_{1-4}$alkyl, wherein —C$_{1-4}$ alkyl is optionally substituted with one or more halogen groups;

each $R_2$ independently represents H or —C$_{1-4}$alkyl;

$L_1$ is —C(O)— or —CH$_2$—;

$L_2$ is —C(O)— or —CH(OH)—;

provided that the compound is not methanone, (5-bromo-2-thienyl)[(3R)-3-[(R)-(4-fluorophenyl)hydroxymethyl]-1-piperidinyl].

As defined generally above, Cy is phenyl, or a 5- or 6-membered aromatic heterocycle containing 1 or 2 heteroatoms selected from O, N and S at any available position on the ring, wherein Cy is optionally substituted with one or more $R_1$ groups, wherein each $R_1$ is independently as described in embodiments herein.

In some embodiments, Cy is phenyl, optionally substituted with one or more $R_1$ groups, wherein each $R_1$ is independently as described in embodiments herein. In some embodiments, Cy is a 5-membered aromatic heterocycle containing 1 or 2 heteroatoms selected from O, N and S at any available position on the ring, optionally substituted with one or more $R_1$ groups, wherein each $R_1$ is independently as described in embodiments herein. In some embodiments, Cy is a 6-membered aromatic heterocycle containing 1 or 2 heteroatoms selected from O, N and S at any available position on the ring, optionally substituted with one or more $R_1$ groups, wherein each $R_1$ is independently as described in embodiments herein.

In some embodiments, Cy is phenyl. In some embodiments, Cy is phenyl, substituted with one $R_1$ group, wherein $R_1$ is as described in embodiments herein. In some embodiments, Cy is phenyl, substituted with two $R_1$ groups, wherein each $R_1$ is independently as described in embodiments herein. In some embodiments, Cy is phenyl, substituted with three $R_1$ groups, wherein each $R_1$ is independently as described in embodiments herein. In some embodiments, Cy is phenyl, substituted with four $R_1$ groups, wherein each $R_1$ is independently as described in embodiments herein.

In some embodiments, Cy is a 5- or 6-membered aromatic heterocycle containing 1 or 2 heteroatoms selected from O, N and S at any available position on the ring. In some embodiments, Cy is a 5- or 6-membered aromatic heterocycle containing 1 or 2 heteroatoms selected from O, N and S at any available position on the ring, substituted with one $R_1$ group, wherein $R_1$ is as described in embodiments herein. In some embodiments, Cy is a 5- or 6-membered aromatic heterocycle containing 1 or 2 heteroatoms selected from O, N and S at any available position on the ring, substituted with two $R_1$ groups, wherein each $R_1$ is independently as described in embodiments herein. In some embodiments, Cy is a 5- or 6-membered aromatic heterocycle containing 1 or 2 heteroatoms selected from O, N and S at any available position on the ring, substituted with three $R_1$ groups, wherein each $R_1$ is independently as described in embodiments herein. In some embodiments, Cy is a 5- or 6-membered aromatic heterocycle containing 1 or 2 heteroatoms selected from O, N and S at any available position on the ring, substituted with four $R_1$ groups, wherein each $R_1$ is independently as described in embodiments herein.

In some embodiments, Cy is a 5- or 6-membered aromatic heterocycle containing 1 heteroatom selected from O, N and S at any available position on the ring. In some embodiments, Cy is a 5- or 6-membered aromatic heterocycle containing 1 heteroatom selected from O, N and S at any available position on the ring, substituted with one $R_1$ group, wherein $R_1$ is as described in embodiments herein. In some embodiments, Cy is a 5- or 6-membered aromatic heterocycle containing 1 heteroatom selected from O, N and S at any available position on the ring, substituted with two $R_1$ groups, wherein each $R_1$ is independently as described in embodiments herein. In some embodiments, Cy is a 5- or 6-membered aromatic heterocycle containing 1 heteroatom selected from O, N and S at any available position on the ring, substituted with three $R_1$ groups, wherein each $R_1$ is independently as described in embodiments herein. In some embodiments, Cy is a 5- or 6-membered aromatic heterocycle containing 1 heteroatom selected from O, N and S at any available position on the ring, substituted with four $R_1$ groups, wherein each $R_1$ is independently as described in embodiments herein.

In some embodiments, Cy is selected from

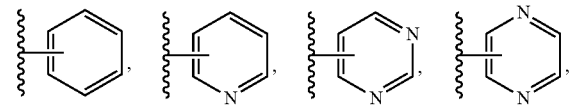

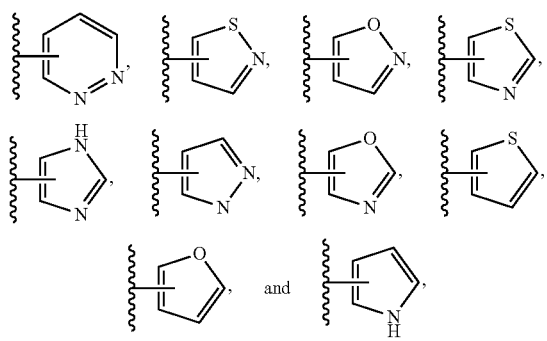

optionally substituted with one or more $R_1$ groups, wherein each $R_1$ is independently as described in embodiments herein.

In some embodiments, Cy is selected from

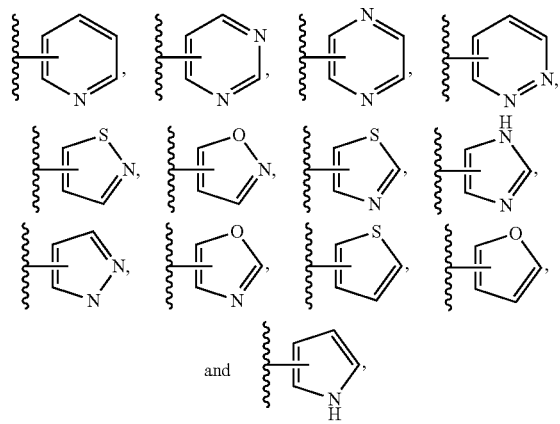

optionally substituted with one or more $R_1$ groups, wherein each $R_1$ is independently as described in embodiments herein.

In some embodiments, Cy is selected from

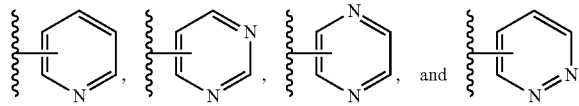

optionally substituted with one or more $R_1$ groups, wherein each $R_1$ is independently as described in embodiments herein.

In some embodiments, Cy is selected from

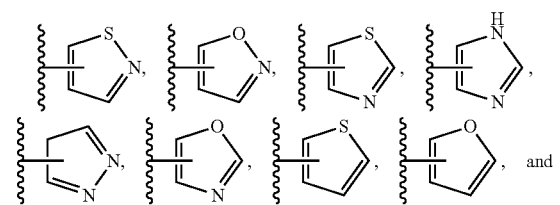

optionally substituted with one or more $R_1$ groups, wherein each $R_1$ is independently as described in embodiments herein.

In some embodiments, Cy is selected from

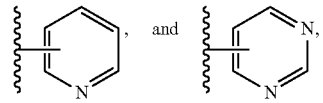

optionally substituted with one or more $R_1$ groups, wherein each $R_1$ is independently as described in embodiments herein.

In some embodiments, Cy is selected from

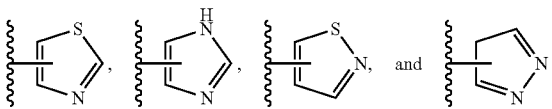

optionally substituted with one or more $R_1$ groups, wherein each $R_1$ is independently as described in embodiments herein.

In some embodiments $C_Y$ is selected from

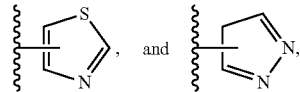

optionally substituted with one or more $R_1$ groups, wherein each $R_1$ is independently as described in embodiments herein.

In some embodiments, Cy is selected from

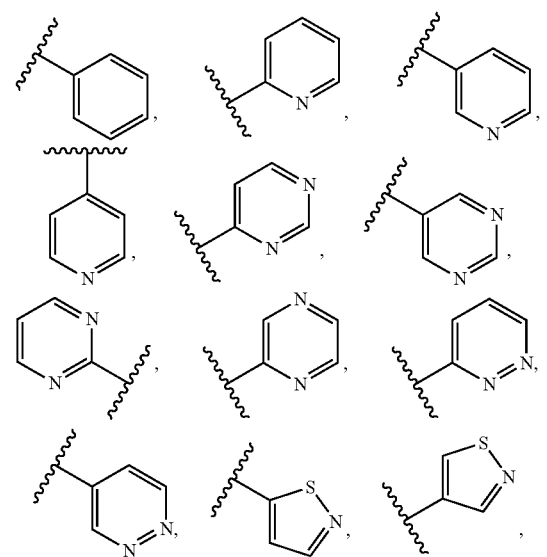

-continued

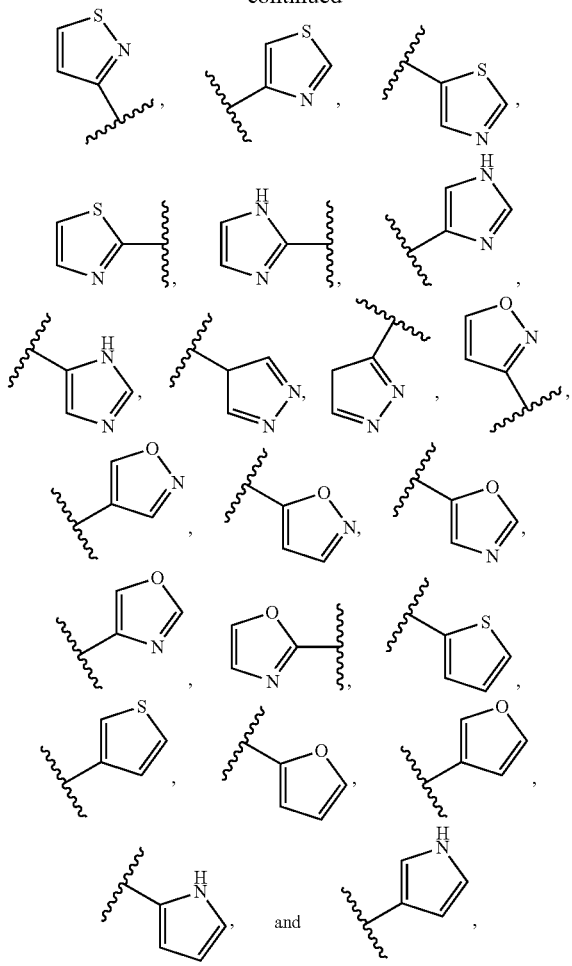

optionally substituted with one or more $R_1$ groups, wherein each $R_1$ is independently as described in embodiments herein.

In some embodiments, Cy is selected from

-continued

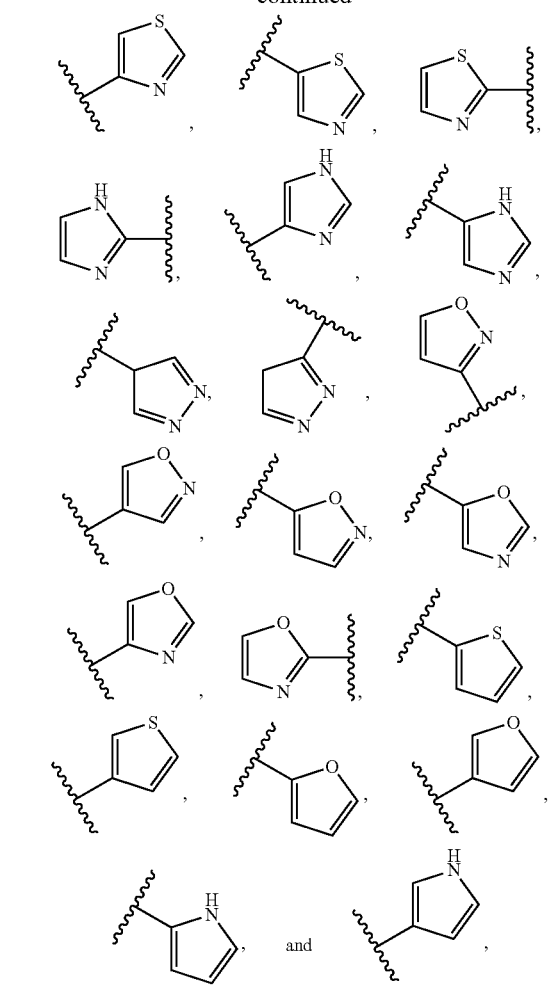

optionally substituted with one or more $R_1$ groups, wherein each $R_1$ is independently as described in embodiments herein.

In some embodiments, Cy is selected from

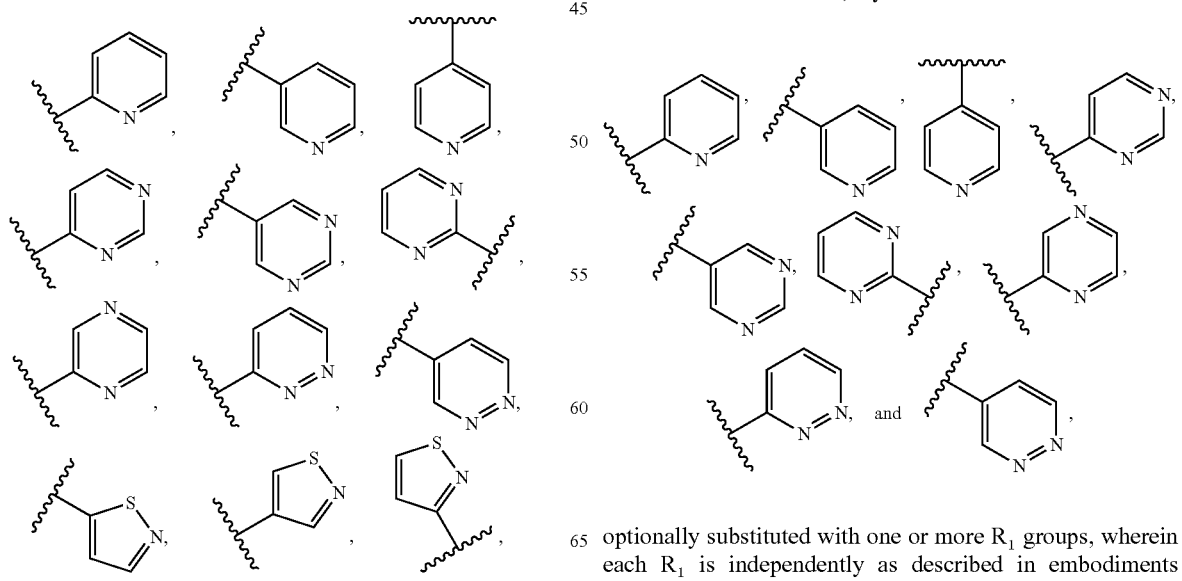

optionally substituted with one or more $R_1$ groups, wherein each $R_1$ is independently as described in embodiments herein.

In some embodiments, Cy is selected from

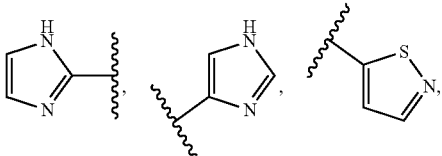

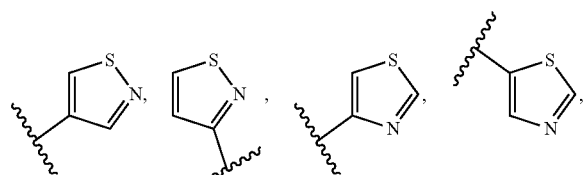

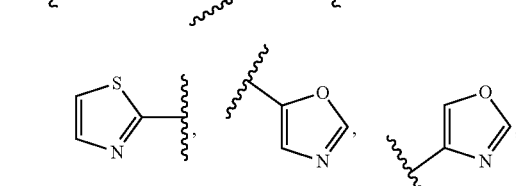

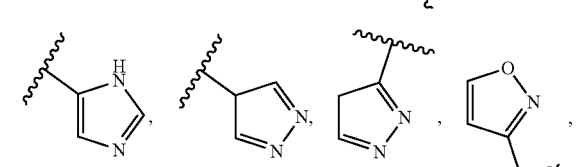

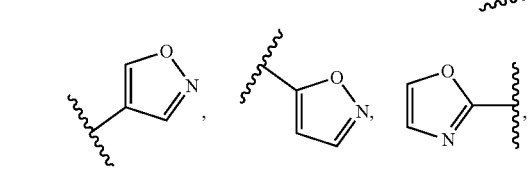

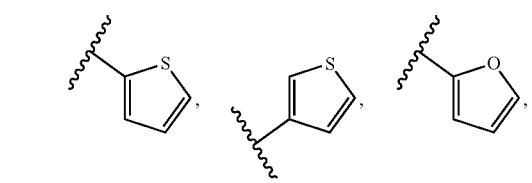

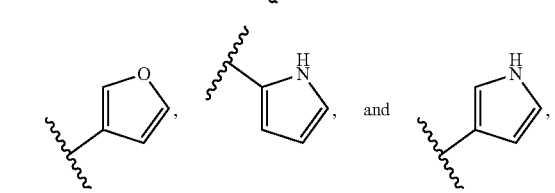

optionally substituted with one or more R₁ groups, wherein each R₁ is independently as described in embodiments herein.

In some embodiments, Cy is selected from

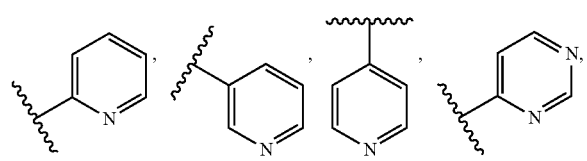

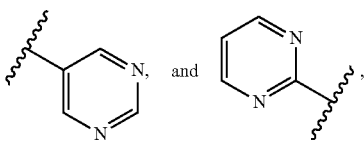

and, optionally substitute with one or more $R_1$ groups, wherein each $R_1$ is independently as described in embodiments herein.

In some embodiments, Cy is selected from

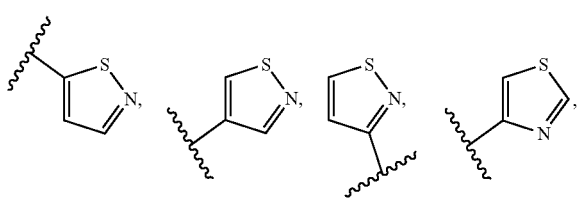

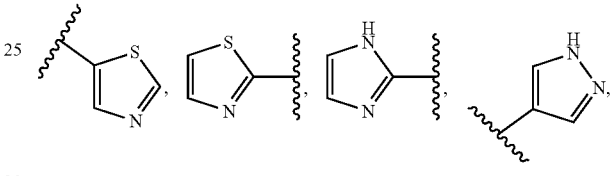

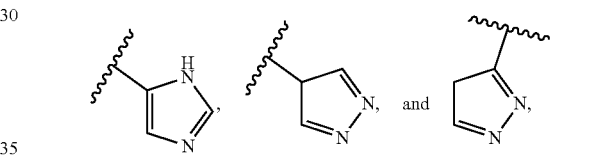

optionally substituted with one or more $R_1$ groups.

In some embodiments, Cy is selected from

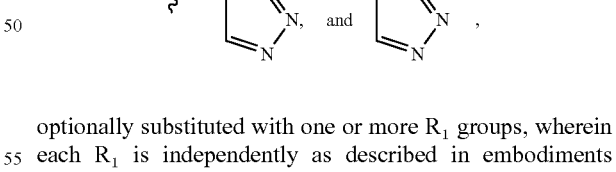

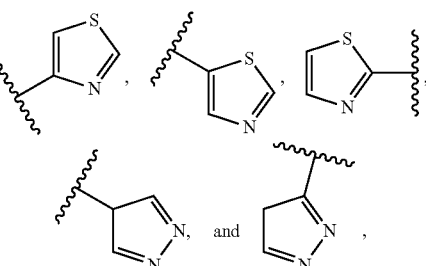

and, optionally substituted with one or more $R_1$ groups, wherein each $R_1$ is independently as described in embodiments herein.

In some embodiments, Cy is selected from

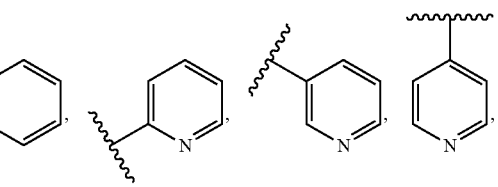

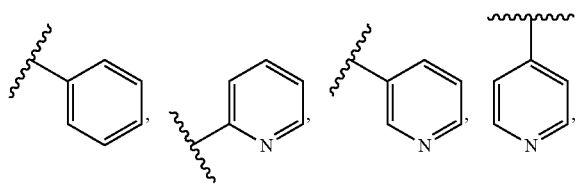

-continued

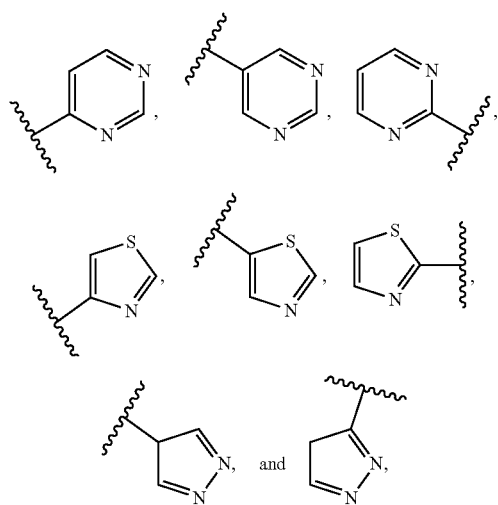

optionally substituted with one or more $R_1$ groups, wherein each $R_1$ is independently as described in embodiments herein.

In some embodiments, Cy is selected from

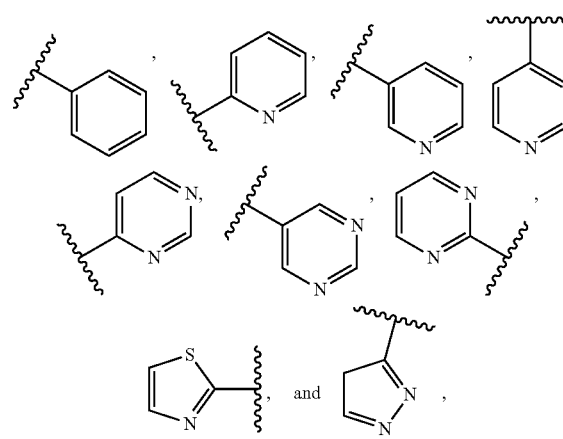

optionally substituted with one or more $R_1$ groups, wherein each $R_1$ is independently as described in embodiments herein.

In some embodiments, Cy is selected from

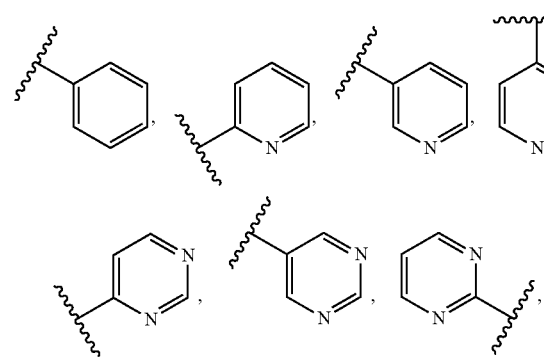

-continued

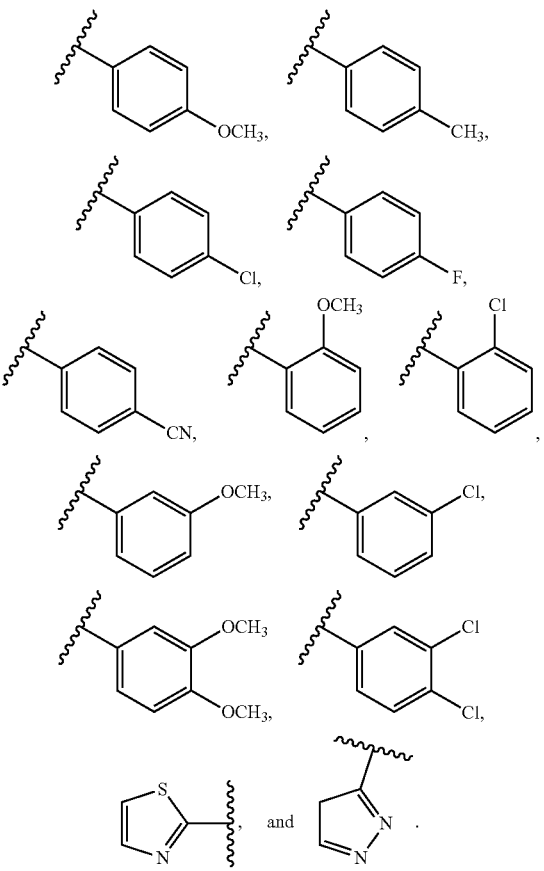

In some embodiments, Cy is selected from

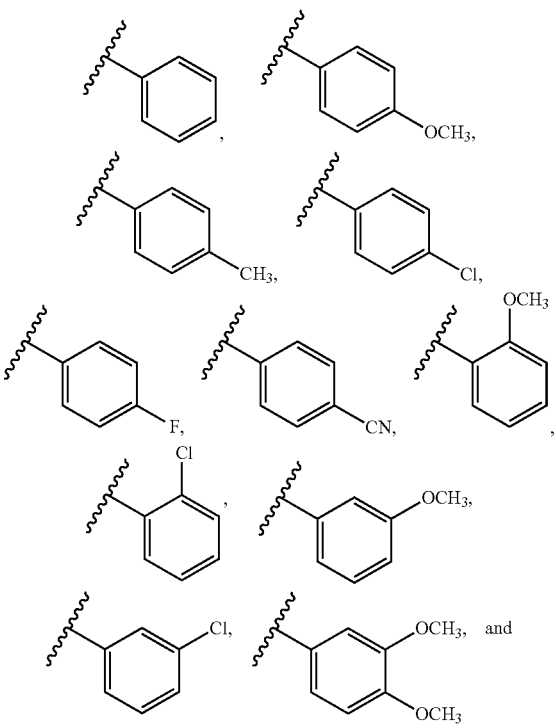

-continued

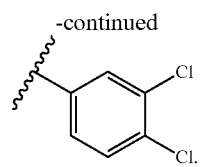

In some embodiments, Cy is selected from

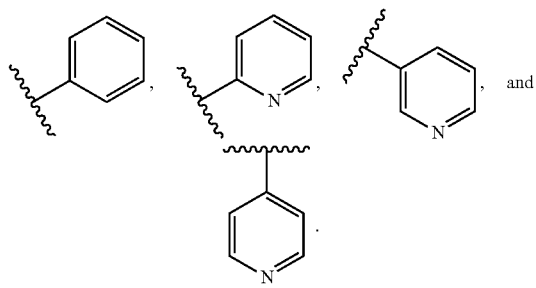

In some embodiments, Cy is selected from

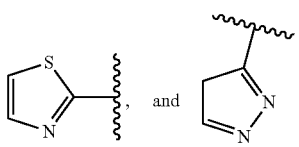

In some embodiments, Cy is selected from those depicted in Tables 1-4 below.

As defined generally above, Cz is phenyl, or a 5- or 6-membered aromatic heterocycle containing 1 or 2 heteroatoms selected from O, N and S at any available position on the ring, wherein Cz is optionally substituted with one or more $R_1$ groups, wherein each $R_1$ is independently as described in embodiments herein.

In some embodiments, Cz is phenyl, optionally substituted with one or more $R_1$ groups, wherein each $R_1$ is independently as described in embodiments herein. In some embodiments, Cz is a 5-membered aromatic heterocycle containing 1 or 2 heteroatoms selected from O, N and S at any available position on the ring, optionally substituted with one or more $R_1$ groups, wherein each $R_1$ is independently as described in embodiments herein. In some embodiments, Cz is a 6-membered aromatic heterocycle containing 1 or 2 heteroatoms selected from O, N and S at any available position on the ring, optionally substituted with one or more $R_1$ groups, wherein each $R_1$ is independently as described in embodiments herein.

In some embodiments, Cz is phenyl. In some embodiments, Cz is phenyl, substituted with one $R_1$ group, wherein $R_1$ is as described in embodiments herein. In some embodiments, Cz is phenyl, substituted with two $R_1$ groups, wherein each $R_1$ is independently as described in embodiments herein. In some embodiments, Cz is phenyl, substituted with three $R_1$ groups, wherein each $R_1$ is independently as described in embodiments herein. In some embodiments, Cz is phenyl, substituted with four $R_1$ groups, wherein each $R_1$ is independently as described in embodiments herein.

In some embodiments, Cz is a 5- or 6-membered aromatic heterocycle containing 1 or 2 heteroatoms selected from O, N and S at any available position on the ring. In some embodiments, Cz is a 5- or 6-membered aromatic heterocycle containing 1 or 2 heteroatoms selected from O, N and S at any available position on the ring, substituted with one $R_1$ group, wherein $R_1$ is as described in embodiments herein. In some embodiments, Cz is a 5- or 6-membered aromatic heterocycle containing 1 or 2 heteroatoms selected from O, N and S at any available position on the ring, substituted with two $R_1$ groups, wherein each $R_1$ is independently as described in embodiments herein. In some embodiments, Cz is a 5- or 6-membered aromatic heterocycle containing 1 or 2 heteroatoms selected from O, N and S at any available position on the ring, substituted with three $R_1$ groups, wherein each $R_1$ is independently as described in embodiments herein. In some embodiments, Cz is a 5- or 6-membered aromatic heterocycle containing 1 or 2 heteroatoms selected from O, N and S at any available position on the ring, substituted with four $R_1$ groups, wherein each $R_1$ is independently as described in embodiments herein.

In some embodiments, Cz is a 5- or 6-membered aromatic heterocycle containing 1 heteroatom selected from O, N and S at any available position on the ring. In some embodiments, Cz is a 5- or 6-membered aromatic heterocycle containing 1 heteroatom selected from O, N and S at any available position on the ring, substituted with one $R_1$ group, wherein $R_1$ is as described in embodiments herein. In some embodiments, Cz is a 5- or 6-membered aromatic heterocycle containing 1 heteroatom selected from O, N and S at any available position on the ring, substituted with two $R_1$ groups, wherein each $R_1$ is independently as described in embodiments herein. In some embodiments, Cz is a 5- or 6-membered aromatic heterocycle containing 1 heteroatom selected from O, N and S at any available position on the ring, substituted with three $R_1$ groups, wherein each $R_1$ is independently as described in embodiments herein. In some embodiments, Cz is a 5- or 6-membered aromatic heterocycle containing 1 heteroatom selected from O, N and S at any available position on the ring, substituted with four $R_1$ groups, wherein each $R_1$ is independently as described in embodiments herein.

In some embodiments, Cz is

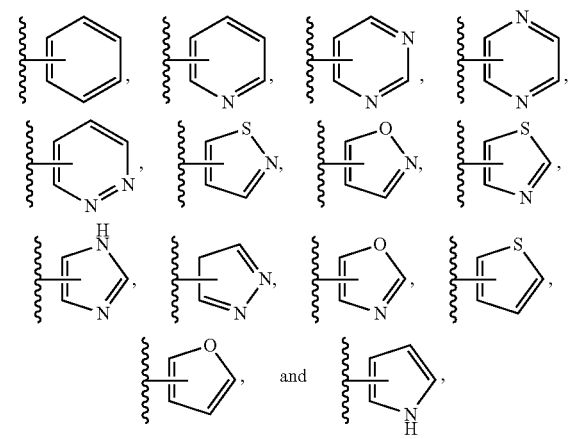

optionally substituted with one or more $R_1$ groups, wherein each $R_1$ is independently as described in embodiments herein.

In some embodiments, $C_Z$ is selected from

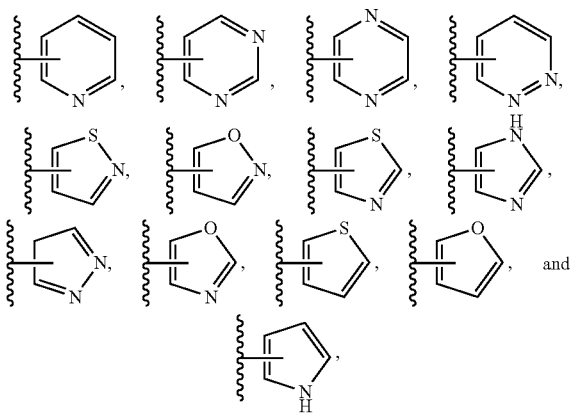

optionally substituted with one or more $R_1$ groups, wherein each $R_1$ is independently as described in embodiments herein.

In some embodiments, $C_Z$ is selected from

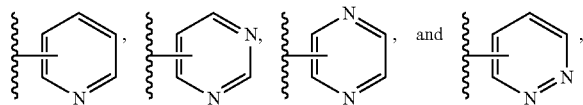

optionally substituted with one or more $R_1$ groups, wherein each $R_1$ is independently as described in embodiments herein.

In some embodiments, $C_Z$ is selected from

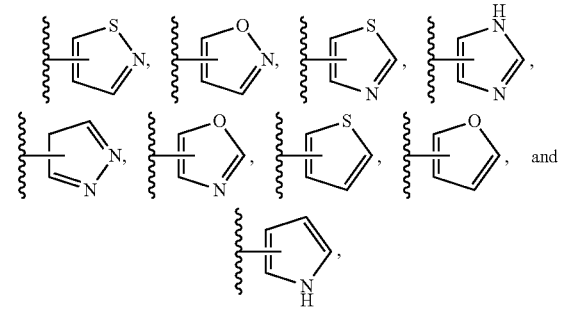

optionally substituted with one or more $R_1$ groups, wherein each $R_1$ is independently as described in embodiments herein.

In some embodiments, $C_Z$ is selected from

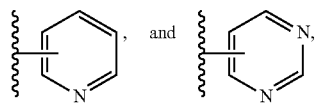

optionally substituted with one or more $R_1$ groups, wherein each $R_1$ is independently as described in embodiments herein.

In some embodiments, $C_Z$ is selected from

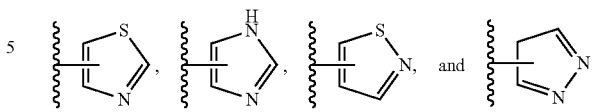

optionally substituted with one or more $R_1$ groups, wherein each $R_1$ is independently as described in embodiments herein.

In some embodiments, $C_Z$ is selected from

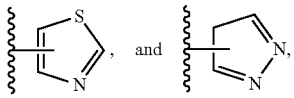

optionally substituted with one or more $R_1$ groups, wherein each $R_1$ is independently as described in embodiments herein.

In some embodiments, $C_Z$ is selected from

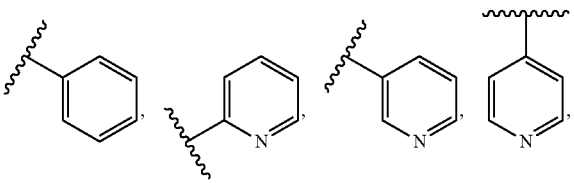

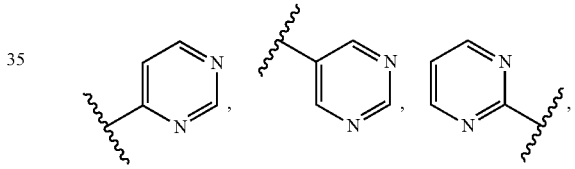

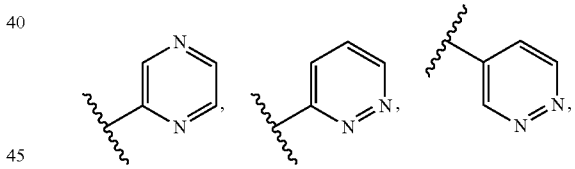

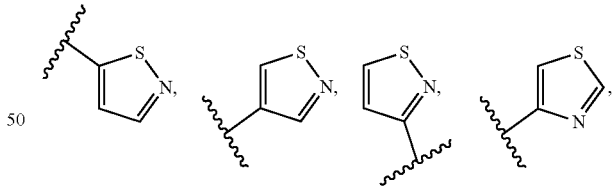

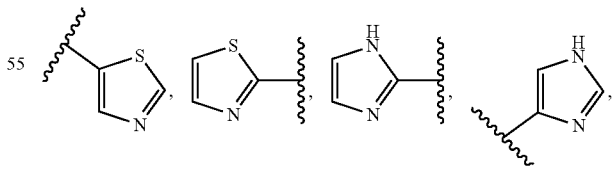

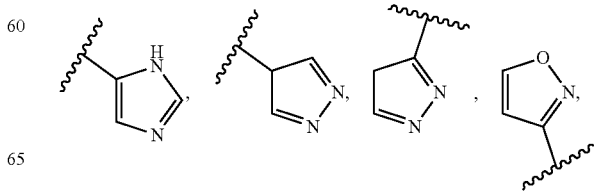

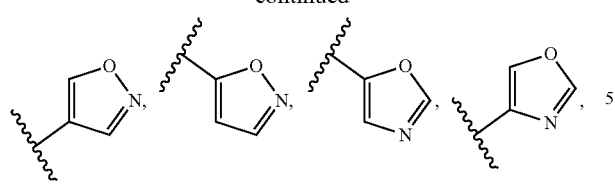

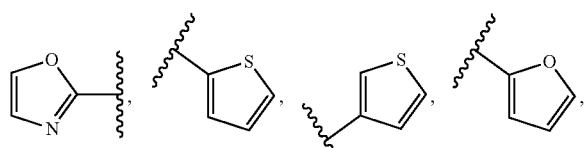

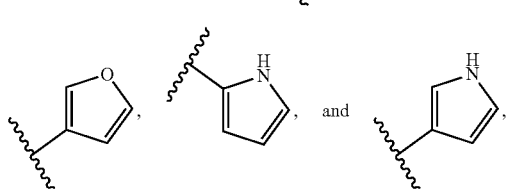

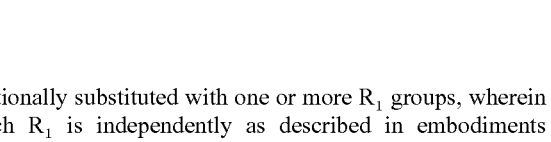

optionally substituted with one or more R₁ groups, wherein each R₁ is independently as described in embodiments herein.

In some embodiments, $C_Z$ is selected from

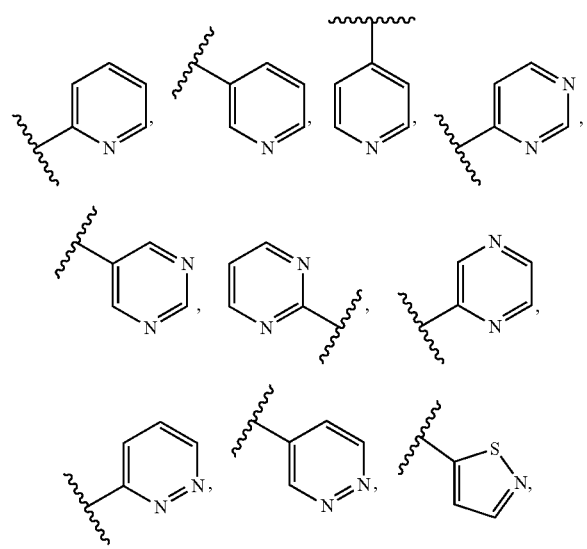

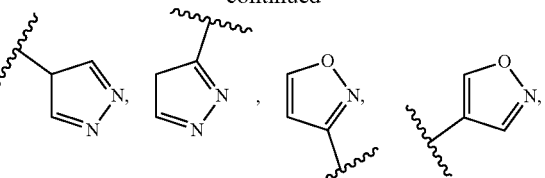

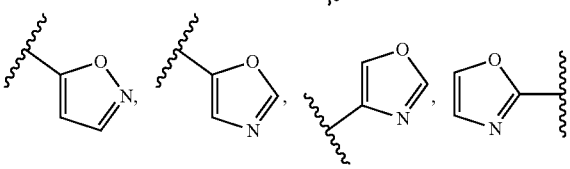

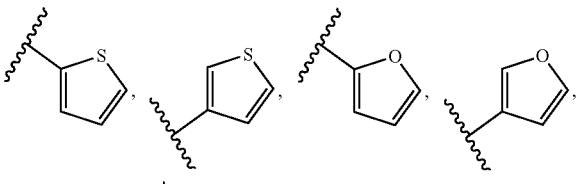

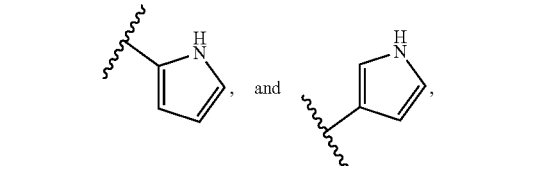

optionally substituted with one or more R₁ groups, wherein each R₁ is independently as described in embodiments herein.

In some embodiments, $C_Z$ is selected from

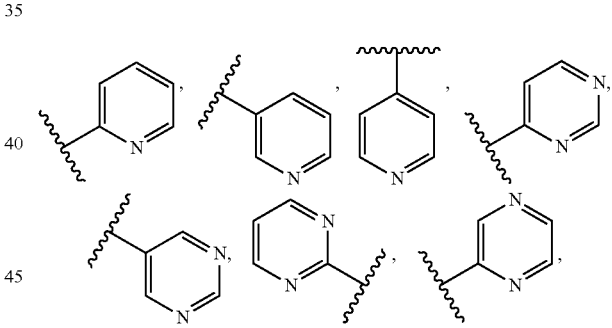

optionally substituted with one or more R₁ groups, wherein each R₁ is independently as described in embodiments herein.

In some embodiments, $C_Z$ is selected from

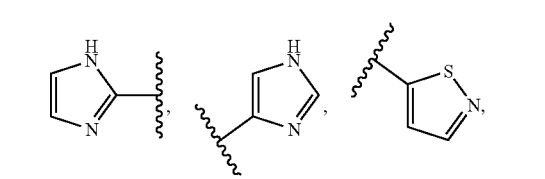

-continued

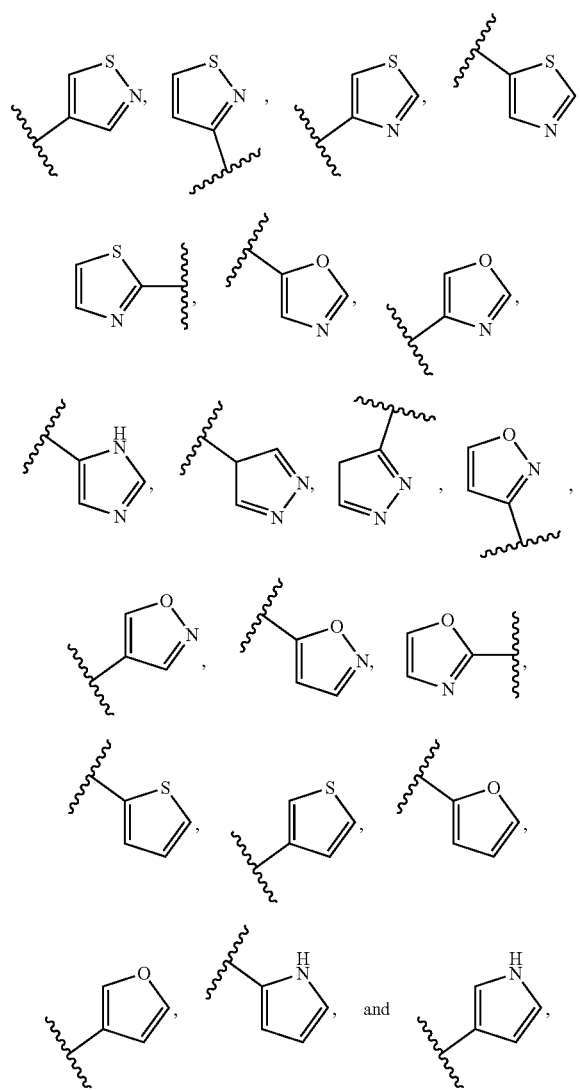

optionally substituted with one or more $R_1$ groups, wherein each $R_1$ is independently as described in embodiments herein.

In some embodiments $C_Z$ is selected from and

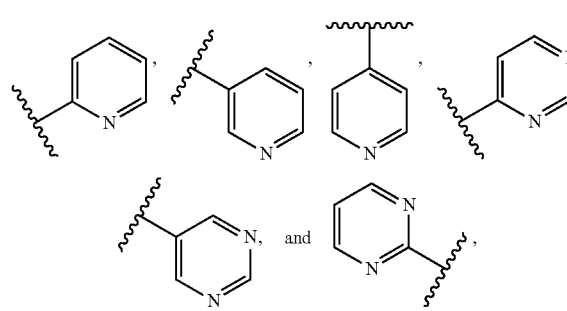

optionally substituted with one or more $R_1$ groups, wherein each $R_1$ is independently as described in embodiments herein.

In some embodiments, $C_Z$ is selected from

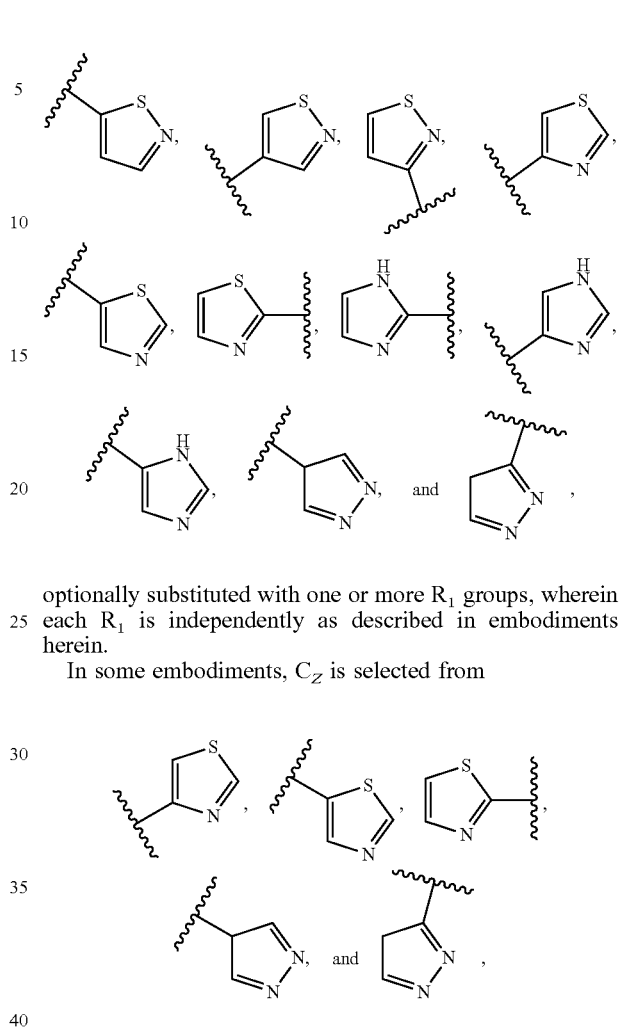

optionally substituted with one or more $R_1$ groups, wherein each $R_1$ is independently as described in embodiments herein.

In some embodiments, $C_Z$ is selected from optionally substituted with one or more $R_1$ groups, wherein each $R_1$ is independently as described in embodiments herein.

In some embodiments, $C_Z$ is selected from

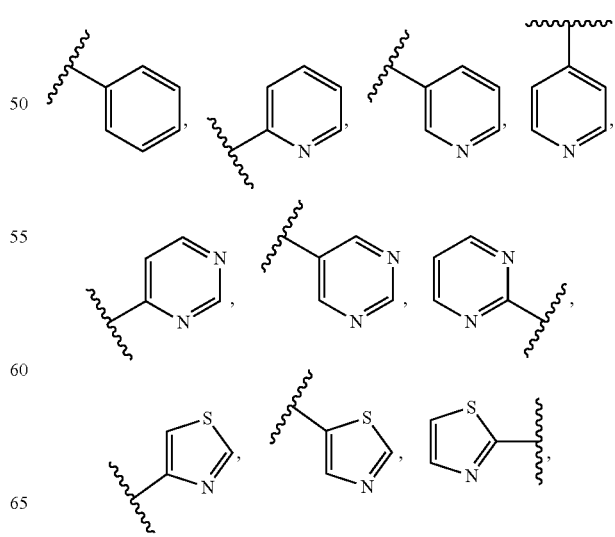

-continued

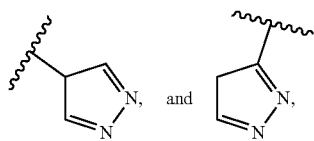

optionally substituted with one or more $R_1$ groups, wherein each $R_1$ is independently as described in embodiments herein.

In some embodiments, $C_Z$ is selected from

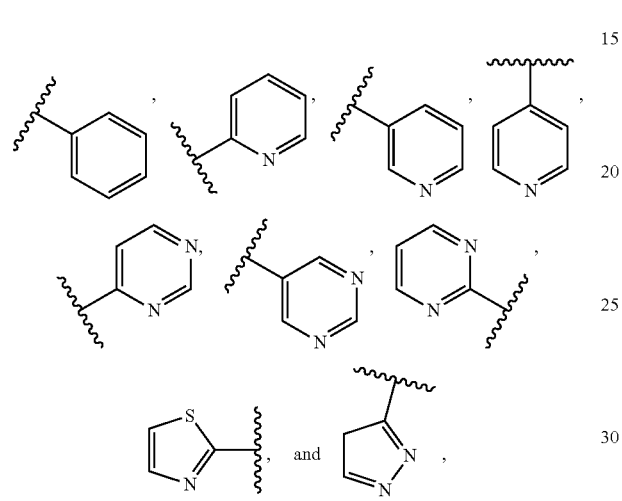

optionally substituted with one or more $R_1$ groups, wherein each $R_1$ is independently as described in embodiments herein.

In some embodiments, $C_Z$ is selected from

-continued

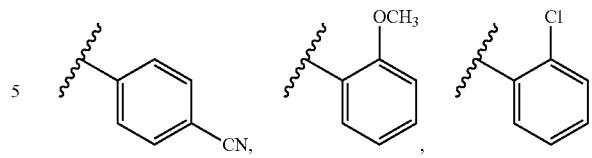

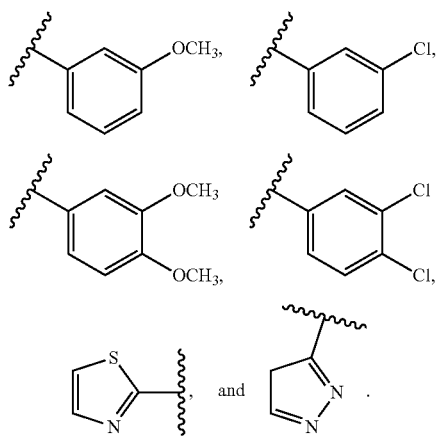

In some embodiments, $C_Z$ is selected from

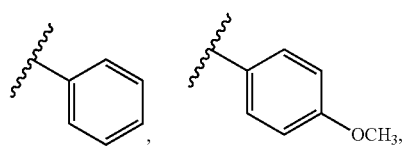

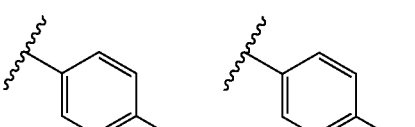

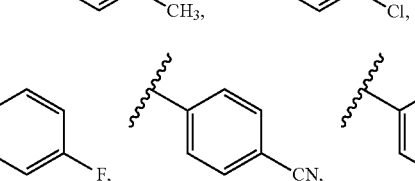

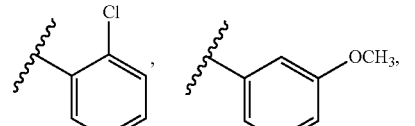

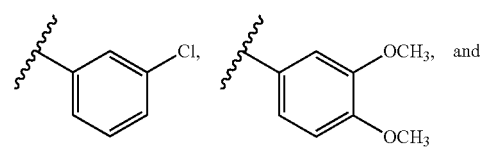

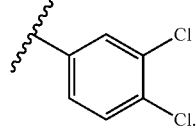

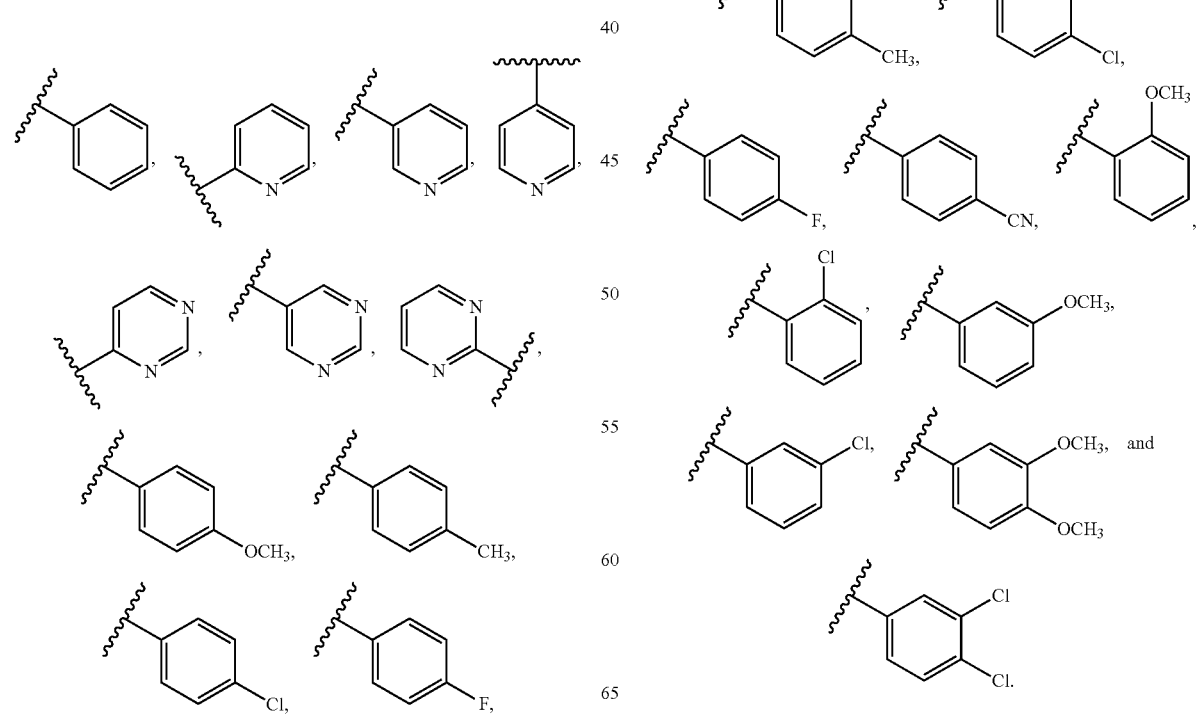

In some embodiments, $C_Z$ is selected from

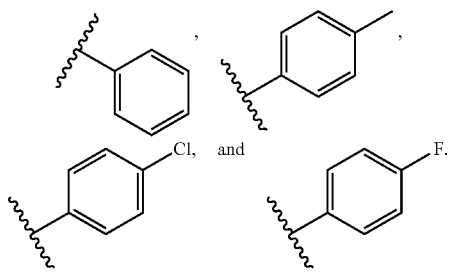

In some embodiments, $C_Z$ is selected from

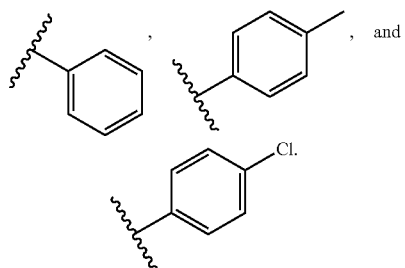

In some embodiments, $C_Z$ is selected from

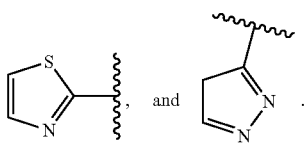 [SMILES: *c1nccs1 ; *C1=NN=CC1]

In some embodiments, $C_Z$ is selected from those depicted in Tables 1-4 below.

As defined generally above, each $R_1$ independently represents —H, halogen, —CN, —$OR_2$, or —$C_{1-4}$alkyl, wherein —$C_{1-4}$alkyl is optionally substituted with one or more halogen groups.

In some embodiments, $R_1$ is —H. In some embodiments, $R_1$ is halogen, —CN, —$OR_2$, or —$C_{1-4}$alkyl, wherein —$C_{1-4}$alkyl is optionally substituted with one or more halogen groups.

In some embodiments, $R_1$ is halogen or —$C_{1-4}$alkyl.

In some embodiments, $R_1$ is halogen. In some embodiments, $R_1$ is F. In some embodiments, $R_1$ is Cl. In some embodiments, $R_1$ is Br. In some embodiments, $R_1$ is I.

In some embodiments, $R_1$ is —CN.

In some embodiments, $R_1$ is —OH.

In some embodiments, $R_1$ is —$C_{1-4}$alkyl, optionally substituted with one or more halogen groups. In some embodiments, $R_1$ is —$C_{1-4}$alkyl. In some embodiments, $R_1$ is —$C_{1-4}$alkyl, substituted with one halogen group. In some embodiments, $R_1$ is —$C_{1-4}$alkyl, substituted with two halogen groups. In some embodiments, $R_1$ is —$C_{1-4}$alkyl, substituted with three halogen groups. In some embodiments, $R_1$ is —$C_{1-4}$alkyl, substituted with four halogen groups.

In some embodiments, $R_1$ is —O—$C_{1-4}$alkyl, wherein —$C_{1-4}$alkyl is optionally substituted with one or more halogen groups. In some embodiments, $R_1$ is —O—$C_{1-4}$alkyl. In some embodiments, $R_1$ is —O—$C_{1-4}$alkyl, substituted with one halogen group. In some embodiments, $R_1$ is —O—$C_{1-4}$alkyl, substituted with two halogen groups. In some embodiments, $R_1$ is —O—$C_{1-4}$alkyl, substituted with three halogen groups. In some embodiments, $R_1$ is —O—$C_{1-4}$alkyl, substituted with four halogen groups.

In some embodiments, $R_1$ is —$CH_3$. In some embodiments, $R_1$ is —$OCH_3$.

In some embodiments, $R_1$ is selected from those depicted in Tables 1-4 below.

As defined generally above, each $R_2$ independently represents —H or —$C_{1-4}$alkyl.

In some embodiments, $R_2$ is —H.

In some embodiments, $R_2$ is —$C_{1-4}$alkyl. In some embodiments, $R_2$ is methyl. In some embodiments, $R_2$ is ethyl. In some embodiments, $R_2$ is propyl. In some embodiments, $R_2$ is isopropyl. In some embodiments, $R_2$ is n-butyl. In some embodiments, $R_2$ is isobutyl. In some embodiments, $R_2$ is t-butyl.

In some embodiments, $R_2$ is selected from those depicted in Tables 1-4 below.

As defined generally above, $L_1$ is —C(O)— or —$CH_2$—.
In some embodiments, $L_1$ is —C(O)—.
In some embodiments, $L_1$ is —$CH_2$—.
In some embodiments, $L_1$ is selected from those depicted in Tables 1-4 below.

As defined generally above, $L_2$ is —C(O)— or —$CH_2$—.
In some embodiments, $L_2$ is —C(O)—.
In some embodiments, $L_2$ is —$CH_2$—.
In some embodiments, $L_2$ is selected from those depicted in Tables 1-4 below.

In some embodiments, the present invention provides a compound of Formula IV:

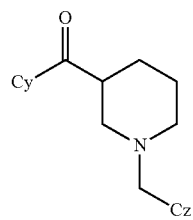

IV or a pharmaceutically acceptable salt thereof, wherein each of Cy and Cz is as defined above and described in embodiments herein, both singly and in combination.

In some embodiments, the present invention provides a compound of Formula V:

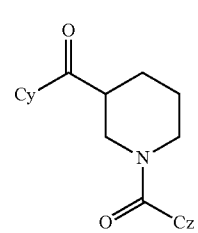

V or a pharmaceutically acceptable salt thereof, wherein each of Cy and Cz is as defined above and described in embodiments herein, both singly and in combination.

In some embodiments, the present invention provides a compound of Formula VI:

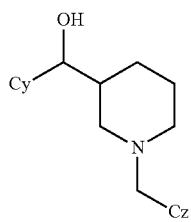

or a pharmaceutically acceptable salt thereof, wherein each of Cy and Cz is as defined above and described in embodiments herein, both singly and in combination.

In some embodiments, the present invention provides a compound of Formula VII:

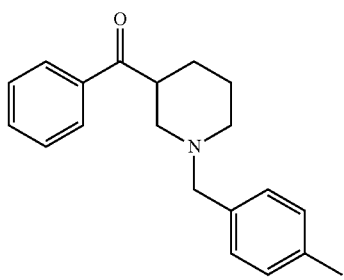 [SMILES: Cc1ccc(CN2CCCC(C(=O)c3ccccc3)C2)cc1]

or a pharmaceutically acceptable salt thereof, wherein each of Cy and Cz is as defined above and described in embodiments herein, both singly and in combination.

In some embodiments, the present invention provides a compound of Table 1.

TABLE 1

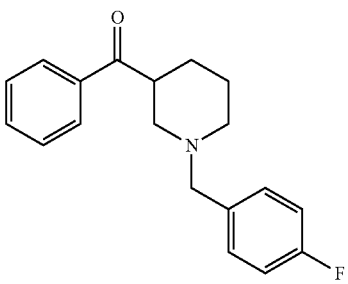 [SMILES: O=C(c1ccccc1)C1CCCN(Cc2ccc(F)cc2)C1]

IV-1

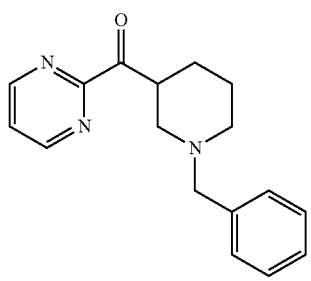

IV-2

TABLE 1-continued

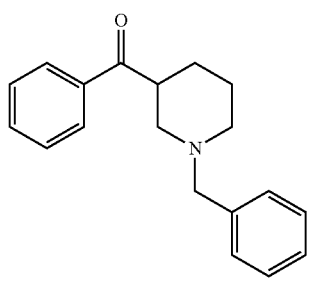 [SMILES: O=C(c1ccccc1)C1CCCN(Cc2ccccc2)C1]

IV-3

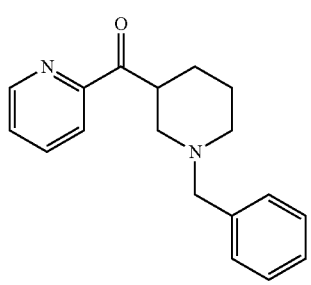 [SMILES: O=C(c1ccccn1)C1CCCN(Cc2ccccc2)C1]

IV-4

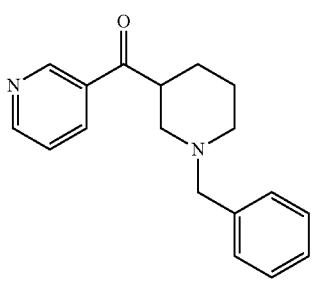

IV-5

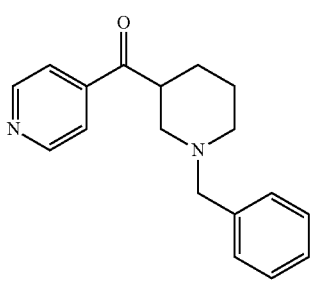 [SMILES: O=C(c1ccncc1)C1CCCN(Cc2ccccc2)C1]

IV-6

IV-7

TABLE 1-continued
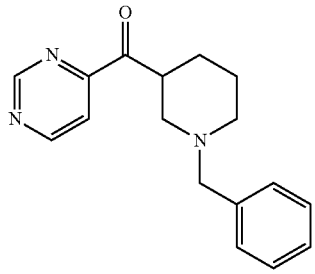
IV-8
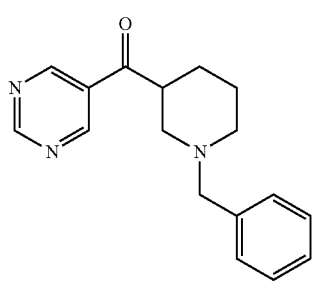 [SMILES: O=C(c1cncnc1)C1CCCN(Cc2ccccc2)C1]
IV-9
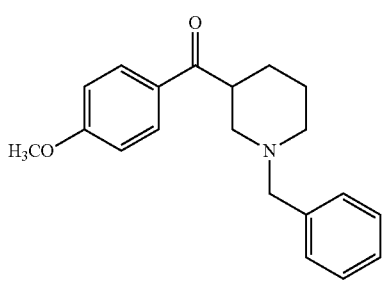 [SMILES: COc1ccc(C(=O)C2CCCN(Cc3ccccc3)C2)cc1]
IV-10
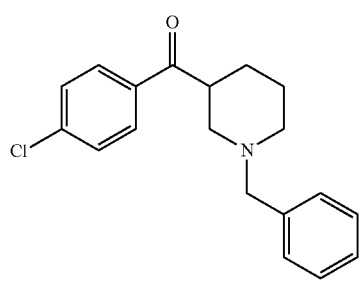 [SMILES: O=C(c1ccc(Cl)cc1)C1CCCN(Cc2ccccc2)C1]
IV-11
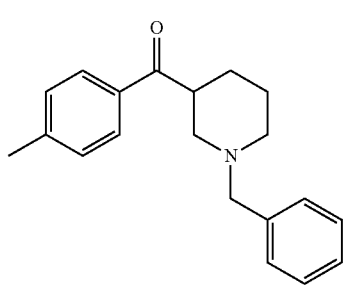 [SMILES: Cc1ccc(C(=O)C2CCCN(Cc3ccccc3)C2)cc1]
IV-12
TABLE 1-continued
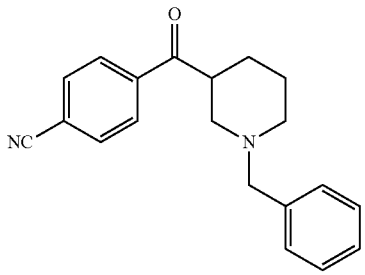
IV-13
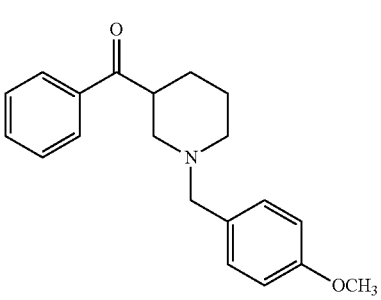 [SMILES: COc1ccc(CN2CCCC(C(=O)c3ccccc3)C2)cc1]
IV-14
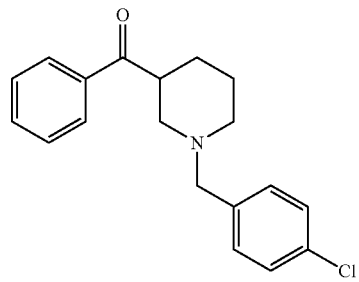 [SMILES: O=C(c1ccccc1)C1CCCN(Cc2ccc(Cl)cc2)C1]
IV-15
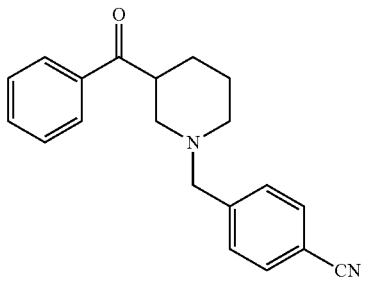 [SMILES: N#Cc1ccc(CN2CCCC(C(=O)c3ccccc3)C2)cc1]
IV-16
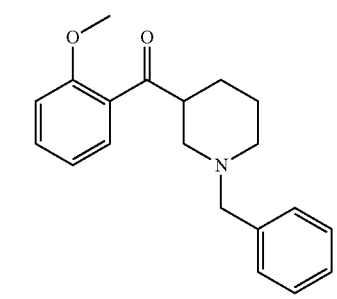 [SMILES: COc1ccccc1C(=O)C1CCCN(Cc2ccccc2)C1]
IV-17

TABLE 1-continued
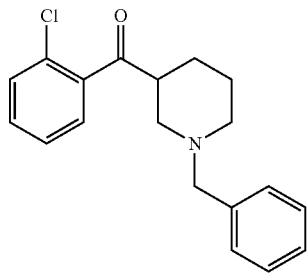 [SMILES: O=C(c1ccccc1Cl)C1CCCN(Cc2ccccc2)C1] IV-18
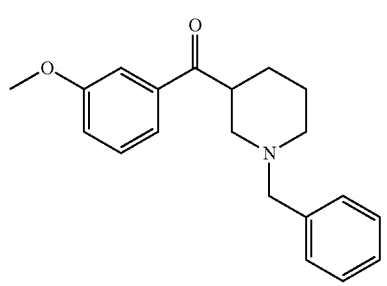 [SMILES: COc1cccc(C(=O)C2CCCN(Cc3ccccc3)C2)c1] IV-19
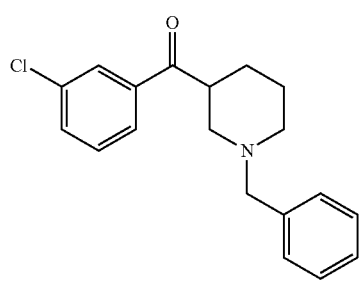 [SMILES: O=C(c1cccc(Cl)c1)C1CCCN(Cc2ccccc2)C1] IV-20
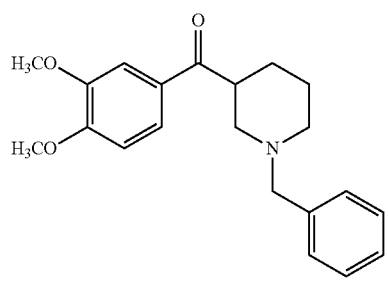 [SMILES: COc1ccc(C(=O)C2CCCN(Cc3ccccc3)C2)cc1OC] IV-21
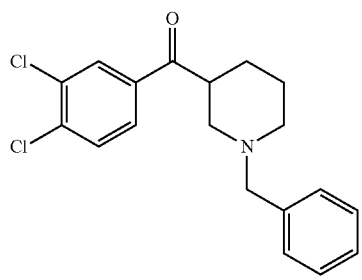 [SMILES: O=C(c1ccc(Cl)c(Cl)c1)C1CCCN(Cc2ccccc2)C1] IV-22
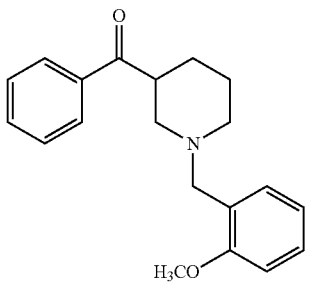 [SMILES: COc1ccccc1CN1CCCC(C(=O)c2ccccc2)C1] IV-23
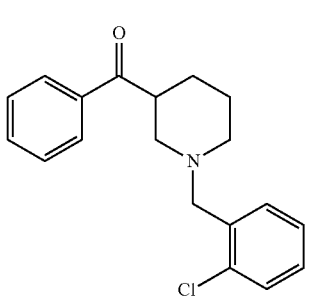 [SMILES: O=C(c1ccccc1)C1CCCN(Cc2ccccc2Cl)C1] IV-24
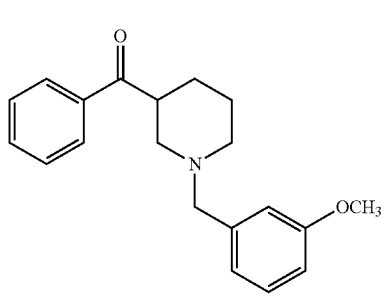 [SMILES: COc1cccc(CN2CCCC(C(=O)c3ccccc3)C2)c1] IV-25
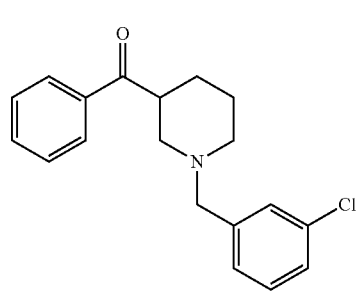 [SMILES: O=C(c1ccccc1)C1CCCN(Cc2cccc(Cl)c2)C1] IV-26
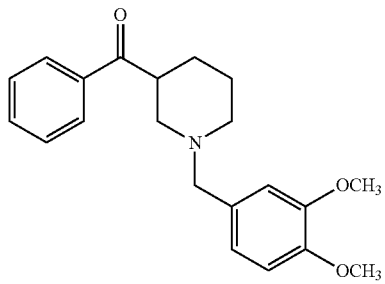 IV-27

TABLE 1-continued
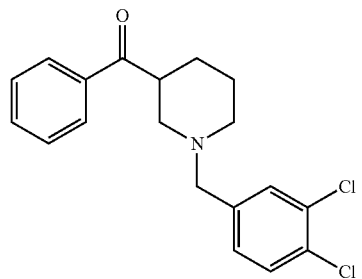 [SMILES: O=C(c1ccccc1)C1CCCN(Cc2ccc(Cl)c(Cl)c2)C1]
IV-28
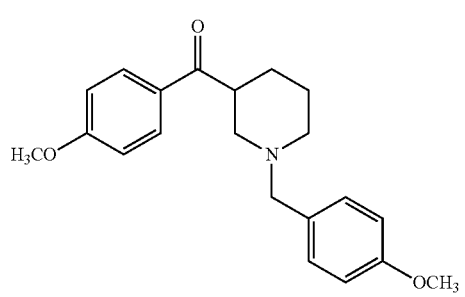 [SMILES: COc1ccc(CN2CCCC(C(=O)c3ccc(OC)cc3)C2)cc1]
IV-29
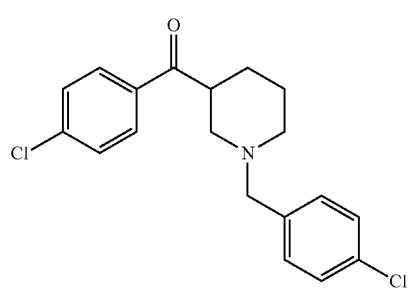 [SMILES: O=C(c1ccc(Cl)cc1)C1CCCN(Cc2ccc(Cl)cc2)C1]
IV-30
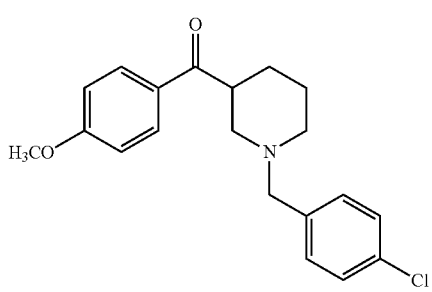
IV-31
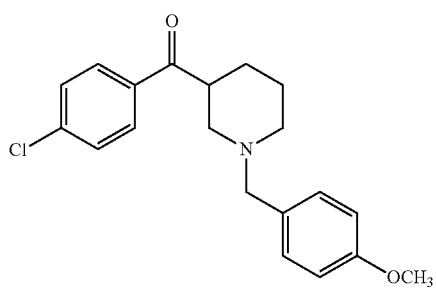 [SMILES: COc1ccc(CN2CCCC(C(=O)c3ccc(Cl)cc3)C2)cc1]
IV-32
TABLE 1-continued
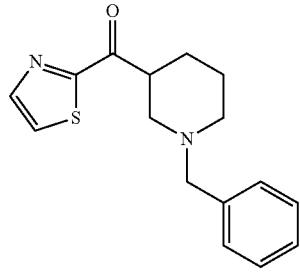 [SMILES: O=C(c1nccs1)C1CCCN(Cc2ccccc2)C1]
IV-33
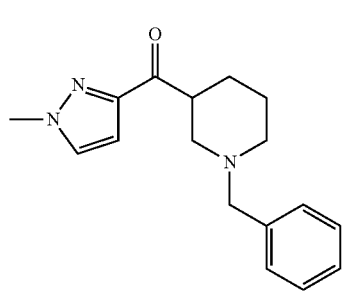 [SMILES: Cn1ccc(C(=O)C2CCCN(Cc3ccccc3)C2)n1]
IV-34
In some embodiments, the present invention provides a compound of Table 2.
TABLE 2
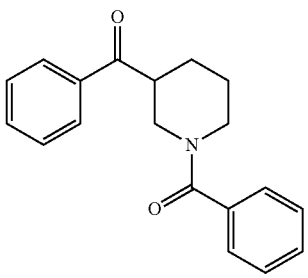 [SMILES: O=C(c1ccccc1)C1CCCN(C(=O)c2ccccc2)C1]
V-1
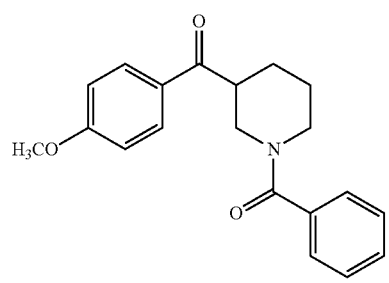 [SMILES: COc1ccc(C(=O)C2CCCN(C(=O)c3ccccc3)C2)cc1]
V-2
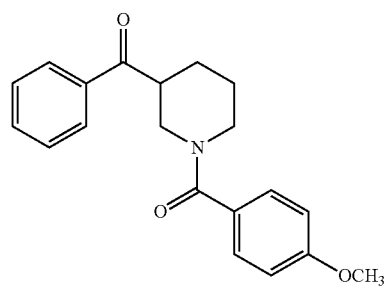 [SMILES: COc1ccc(C(=O)N2CCCC(C(=O)c3ccccc3)C2)cc1]
V-3

TABLE 2-continued
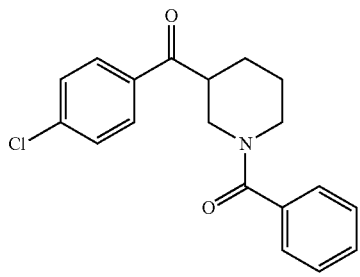 [SMILES: O=C(c1ccc(Cl)cc1)C1CCCN(C(=O)c2ccccc2)C1] V-4
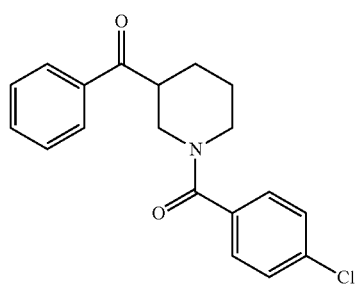 [SMILES: O=C(c1ccccc1)C1CCCN(C(=O)c2ccc(Cl)cc2)C1] V-5
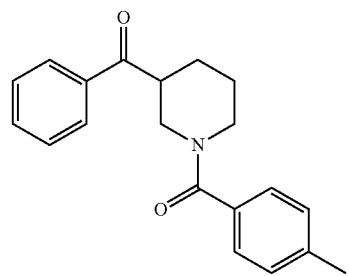 [SMILES: Cc1ccc(C(=O)N2CCCC(C(=O)c3ccccc3)C2)cc1] V-6
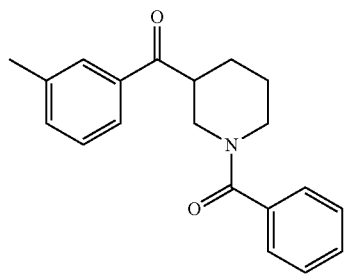 V-7
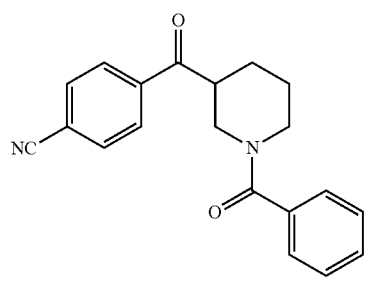 [SMILES: N#Cc1ccc(C(=O)C2CCCN(C(=O)c3ccccc3)C2)cc1] V-8
TABLE 2-continued
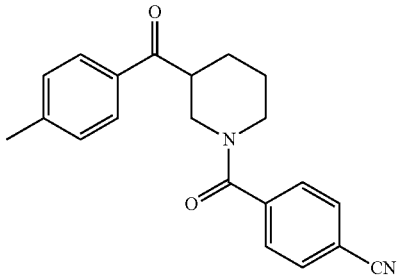 [SMILES: Cc1ccc(C(=O)C2CCCN(C(=O)c3ccc(C#N)cc3)C2)cc1] V-9
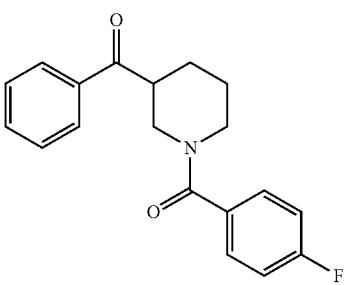 [SMILES: O=C(c1ccccc1)C1CCCN(C(=O)c2ccc(F)cc2)C1] V-10
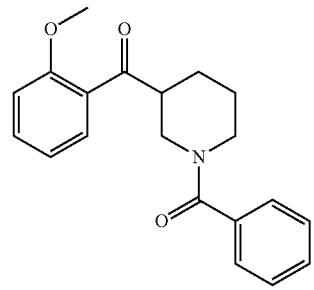 [SMILES: COc1ccccc1C(=O)C1CCCN(C(=O)c2ccccc2)C1] V-11
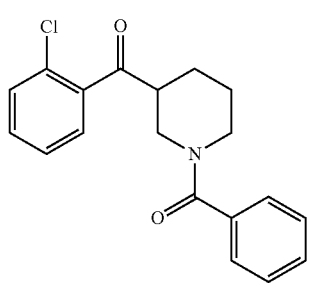 [SMILES: O=C(c1ccccc1Cl)C1CCCN(C(=O)c2ccccc2)C1] V-12
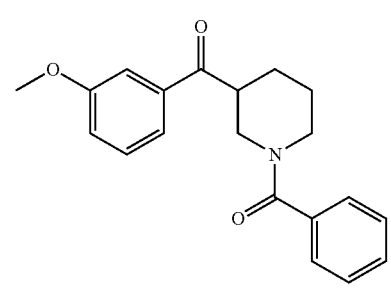 [SMILES: COc1cccc(C(=O)C2CCCN(C(=O)c3ccccc3)C2)c1] V-13

TABLE 2-continued
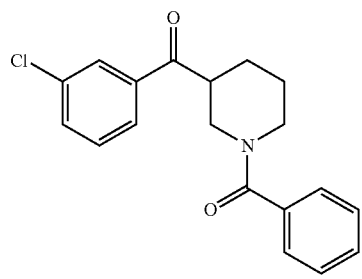 [SMILES: O=C(c1cccc(Cl)c1)C1CCCN(C(=O)c2ccccc2)C1] V-14
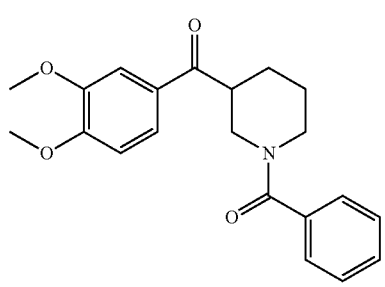 [SMILES: COc1ccc(C(=O)C2CCCN(C(=O)c3ccccc3)C2)cc1OC] V-15
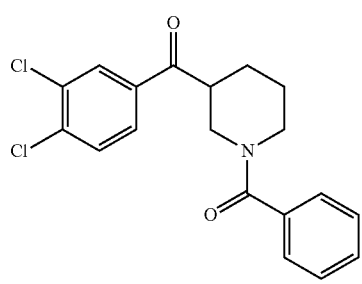 [SMILES: O=C(c1ccc(Cl)c(Cl)c1)C1CCCN(C(=O)c2ccccc2)C1] V-16
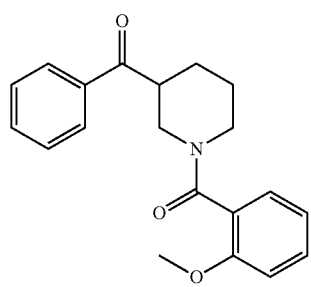 [SMILES: COc1ccccc1C(=O)N1CCCC(C(=O)c2ccccc2)C1] V-17
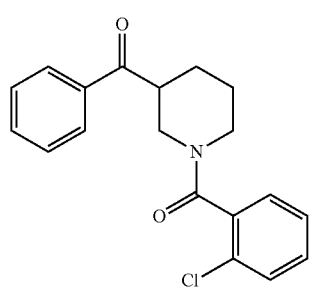 [SMILES: O=C(c1ccccc1)C1CCCN(C(=O)c2ccccc2Cl)C1] V-18
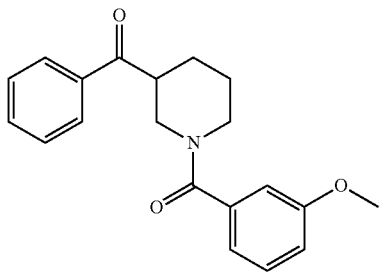 [SMILES: COc1cccc(C(=O)N2CCCC(C(=O)c3ccccc3)C2)c1] V-19
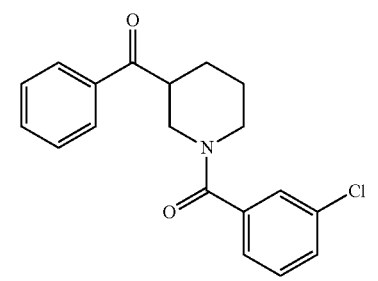 [SMILES: O=C(c1ccccc1)C1CCCN(C(=O)c2cccc(Cl)c2)C1] V-20
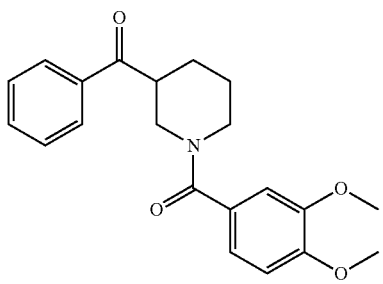 [SMILES: COc1ccc(C(=O)N2CCCC(C(=O)c3ccccc3)C2)cc1OC] V-21
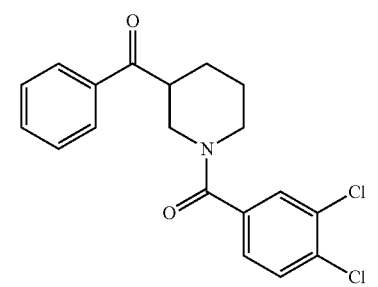 [SMILES: O=C(c1ccccc1)C1CCCN(C(=O)c2ccc(Cl)c(Cl)c2)C1] V-22
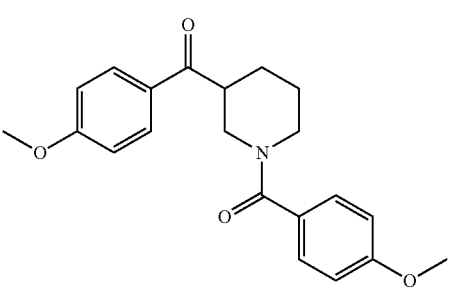 V-23

TABLE 2-continued
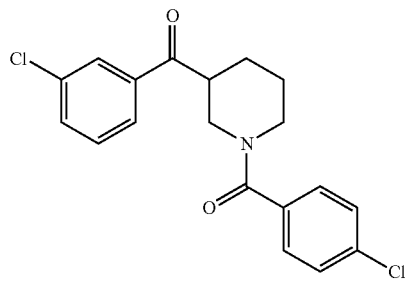 [SMILES: O=C(c1cccc(Cl)c1)C1CCCN(C(=O)c2ccc(Cl)cc2)C1] V-24
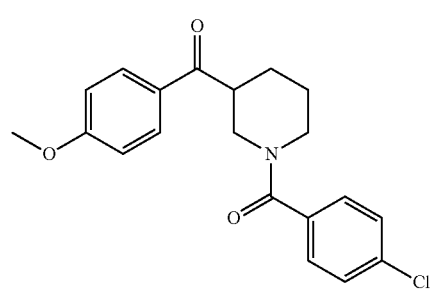 [SMILES: COc1ccc(C(=O)C2CCCN(C(=O)c3ccc(Cl)cc3)C2)cc1] V-25
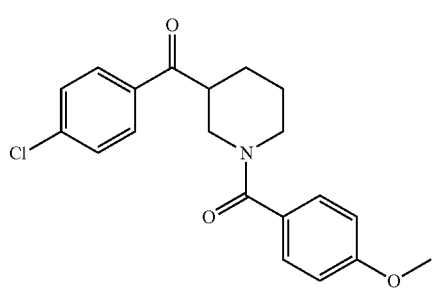 [SMILES: COc1ccc(C(=O)N2CCCC(C(=O)c3ccc(Cl)cc3)C2)cc1] V-26
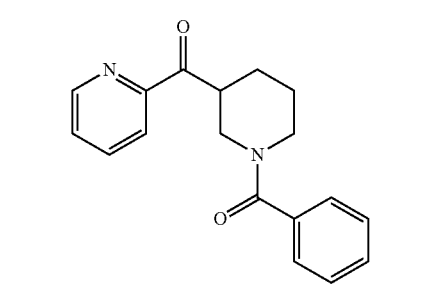 [SMILES: O=C(c1ccccn1)C1CCCN(C(=O)c2ccccc2)C1] V-27
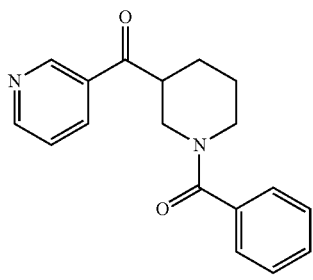 [SMILES: O=C(c1cccnc1)C1CCCN(C(=O)c2ccccc2)C1] V-28
TABLE 2-continued
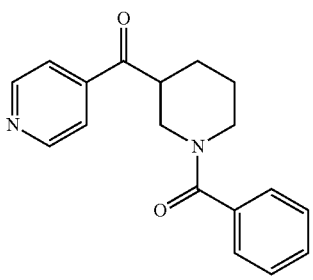 [SMILES: O=C(c1ccncc1)C1CCCN(C(=O)c2ccccc2)C1] V-29
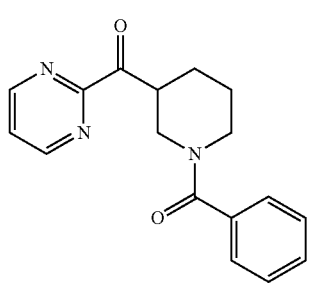 [SMILES: O=C(c1ncccn1)C1CCCN(C(=O)c2ccccc2)C1] V-30
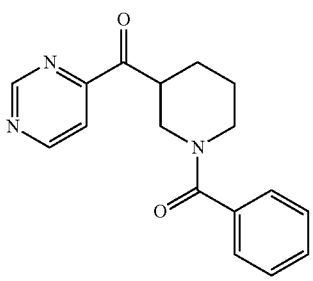 [SMILES: O=C(c1ccncn1)C1CCCN(C(=O)c2ccccc2)C1] V-31
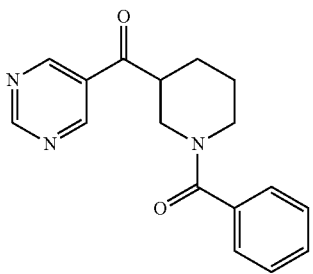 [SMILES: O=C(c1cncnc1)C1CCCN(C(=O)c2ccccc2)C1] V-32
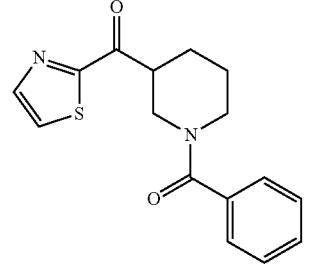 [SMILES: O=C(c1nccs1)C1CCCN(C(=O)c2ccccc2)C1] V-33

TABLE 2-continued

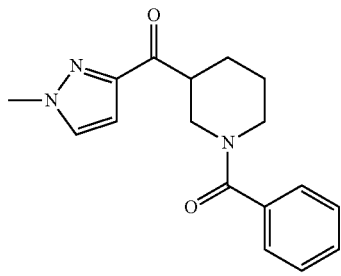 [SMILES: Cn1ccc(C(=O)C2CCCN(C(=O)c3ccccc3)C2)n1]

V-34

In some embodiments, the present invention provides a compound of Table 3.

TABLE 3

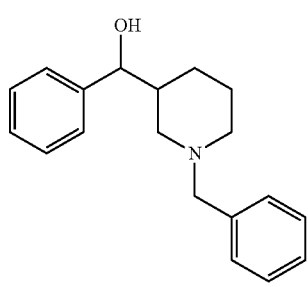 [SMILES: OC(c1ccccc1)C1CCCN(Cc2ccccc2)C1]

VI-1

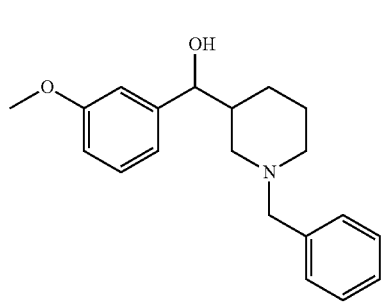 [SMILES: COc1cccc(C(O)C2CCCN(Cc3ccccc3)C2)c1]

VI-2

In some embodiments, compound VI-1 is of formula

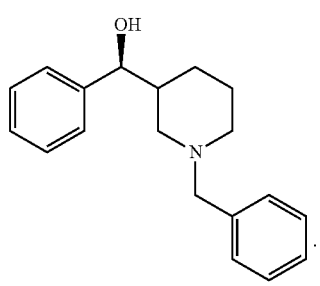 [SMILES: O[C@H](c1ccccc1)C1CCCN(Cc2ccccc2)C1]

In some embodiments, compound VI-1 is of formula

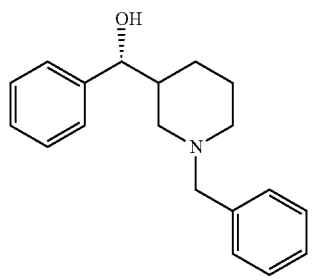

In some embodiments, compound VI-2 is of formula

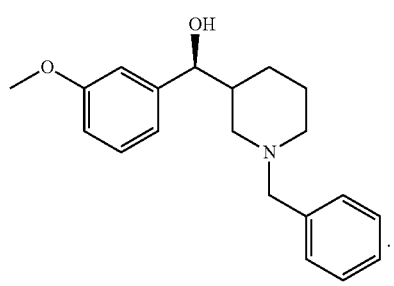 [SMILES: COc1cccc([C@@H](O)C2CCCN(Cc3ccccc3)C2)c1]

In some embodiments, compound VI-2 is of formula

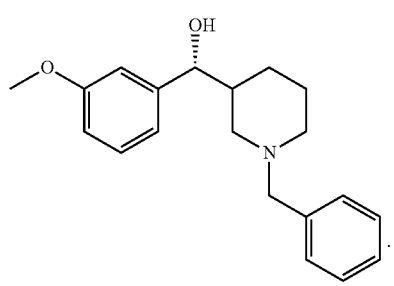 [SMILES: COc1cccc([C@H](O)C2CCCN(Cc3ccccc3)C2)c1]

In some embodiments, the present invention provides a compound of Table 4.

TABLE 4

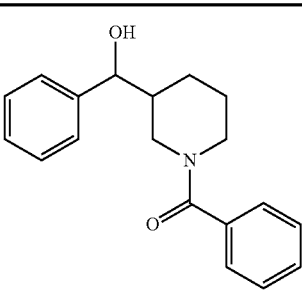

VII-1

TABLE 4-continued
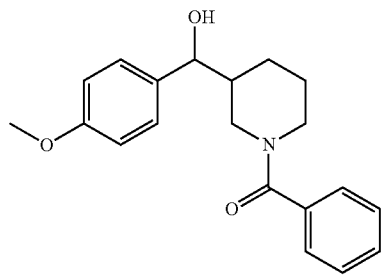 [SMILES: COc1ccc(C(O)C2CCCN(C(=O)c3ccccc3)C2)cc1] VII-2
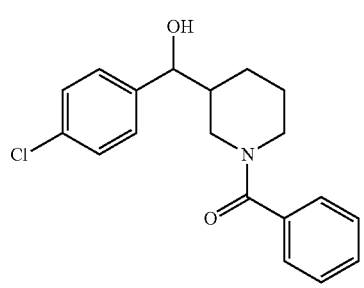 [SMILES: O=C(c1ccccc1)N1CCCC(C(O)c2ccc(Cl)cc2)C1] VII-3
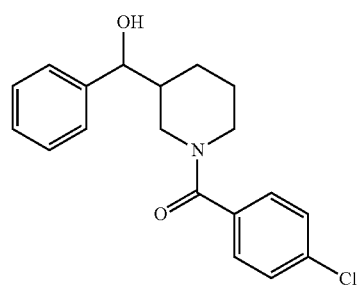 [SMILES: O=C(c1ccc(Cl)cc1)N1CCCC(C(O)c2ccccc2)C1] VII-4
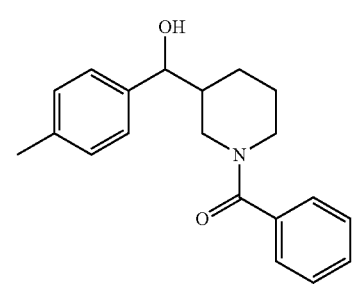 [SMILES: Cc1ccc(C(O)C2CCCN(C(=O)c3ccccc3)C2)cc1] VII-5
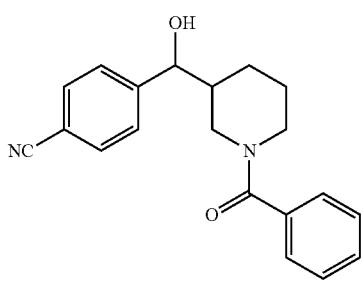 [SMILES: N#Cc1ccc(C(O)C2CCCN(C(=O)c3ccccc3)C2)cc1] VII-6
TABLE 4-continued
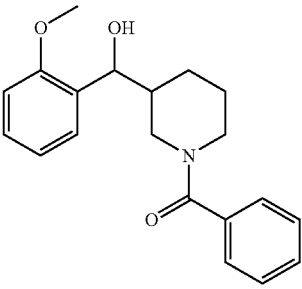 [SMILES: COc1ccccc1C(O)C1CCCN(C(=O)c2ccccc2)C1] VII-7
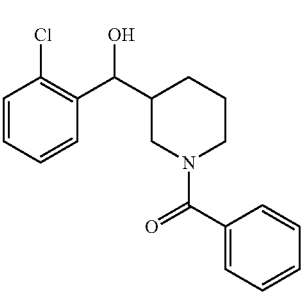 VII-8
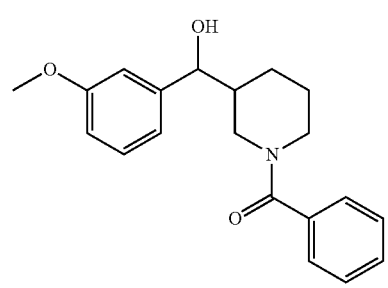 [SMILES: COc1cccc(C(O)C2CCCN(C(=O)c3ccccc3)C2)c1] VII-9
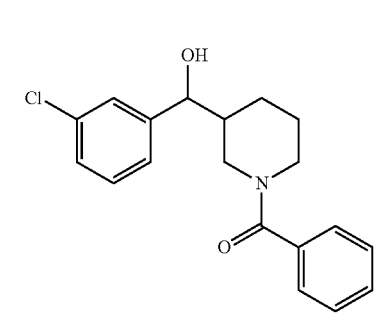 [SMILES: O=C(c1ccccc1)N1CCCC(C(O)c2cccc(Cl)c2)C1] VII-10
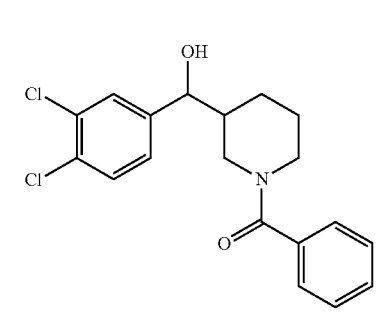 [SMILES: O=C(c1ccccc1)N1CCCC(C(O)c2ccc(Cl)c(Cl)c2)C1] VII-11

TABLE 4-continued
| | |
|---|---|
| 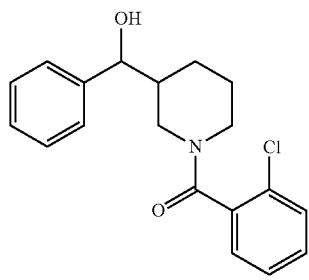 [SMILES: O=C(c1ccccc1Cl)N1CCCC(C(O)c2ccccc2)C1] VII-12 | 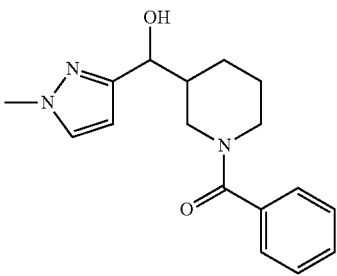 VII-17 |
| 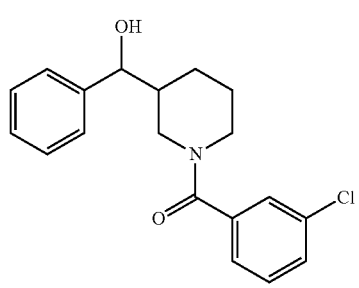 VII-13 | |
In some embodiments, compound VII-1 is of formula
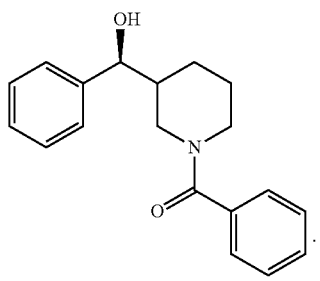
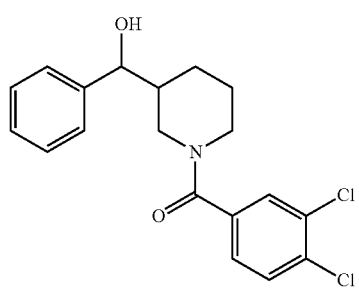 [SMILES: O=C(c1ccc(Cl)c(Cl)c1)N1CCCC(C(O)c2ccccc2)C1] VII-14
In some embodiments, compound VII-1 is of formula
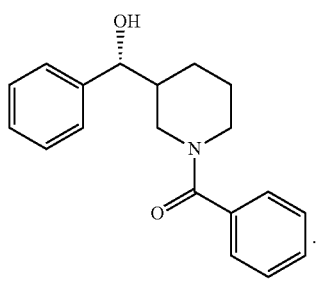
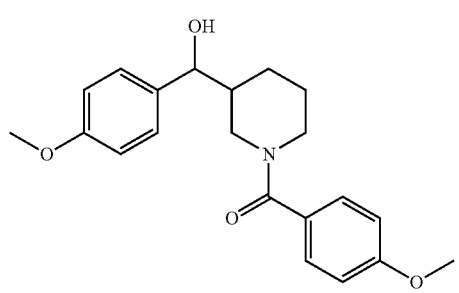 VII-15
In some embodiments, compound VII-2 is of formula
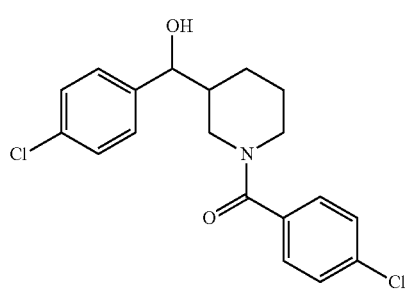 [SMILES: O=C(c1ccc(Cl)cc1)N1CCCC(C(O)c2ccc(Cl)cc2)C1] VII-16
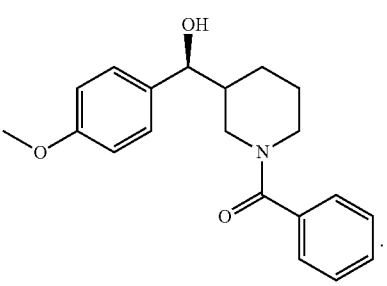 [SMILES: COc1ccc([C@@H](O)C2CCCN(C(=O)c3ccccc3)C2)cc1]

In some embodiments, compound VII-2 is of formula

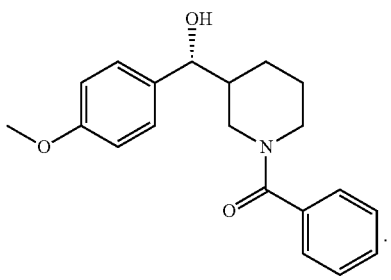 [SMILES: COc1ccc([C@H](O)C2CCCN(C(=O)c3ccccc3)C2)cc1]

In some embodiments, compound VII-3 is of formula

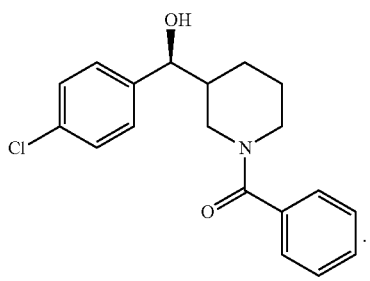 [SMILES: O=C(c1ccccc1)N1CCCC([C@H](O)c2ccc(Cl)cc2)C1]

In some embodiments, compound VII-3 is of formula

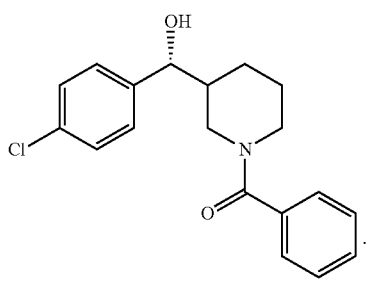 [SMILES: O=C(c1ccccc1)N1CCCC([C@@H](O)c2ccc(Cl)cc2)C1]

In some embodiments, compound VII-4 is of formula

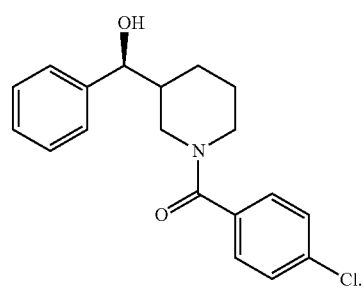 [SMILES: O=C(c1ccc(Cl)cc1)N1CCCC([C@H](O)c2ccccc2)C1]

In some embodiments, compound VII-4 is of formula

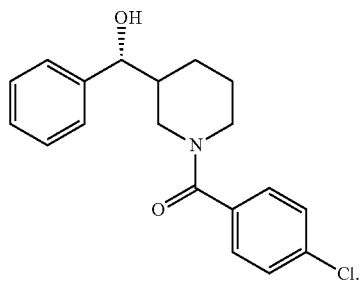 [SMILES: O=C(c1ccc(Cl)cc1)N1CCCC([C@@H](O)c2ccccc2)C1]

In some embodiments, compound VII-5 is of formula

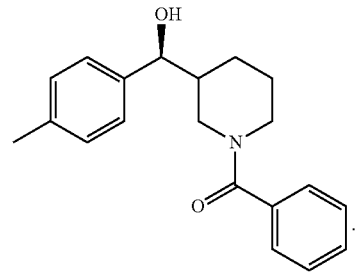 [SMILES: Cc1ccc([C@@H](O)C2CCCN(C(=O)c3ccccc3)C2)cc1]

In some embodiments, compound VII-5 is of formula

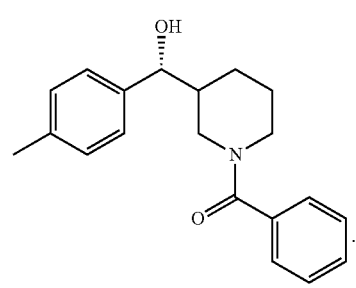 [SMILES: Cc1ccc([C@H](O)C2CCCN(C(=O)c3ccccc3)C2)cc1]

In some embodiments, compound VII-6 is of formula

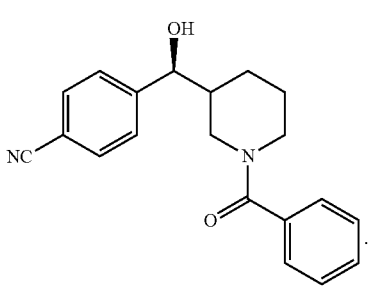 [SMILES: N#Cc1ccc([C@@H](O)C2CCCN(C(=O)c3ccccc3)C2)cc1]

In some embodiments, compound VII-6 is of formula

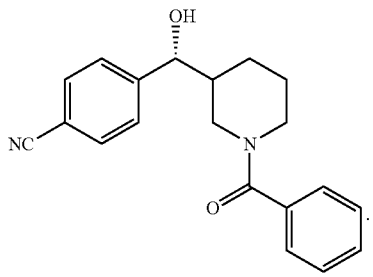 [SMILES: N#Cc1ccc([C@H](O)C2CCCN(C(=O)c3ccccc3)C2)cc1]

In some embodiments, compound VII-7 is of formula

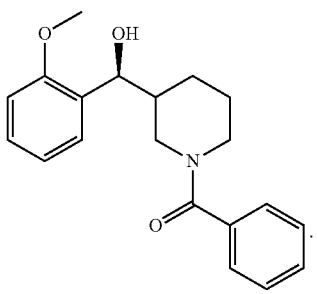 [SMILES: COc1ccccc1[C@@H](O)C1CCCN(C(=O)c2ccccc2)C1]

In some embodiments, compound VII-7 is of formula

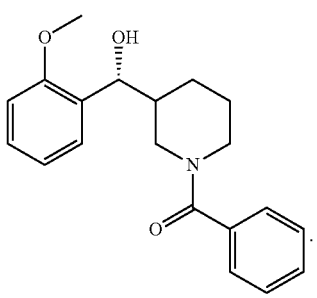 [SMILES: COc1ccccc1[C@H](O)C1CCCN(C(=O)c2ccccc2)C1]

In some embodiments, compound VII-8 is of formula

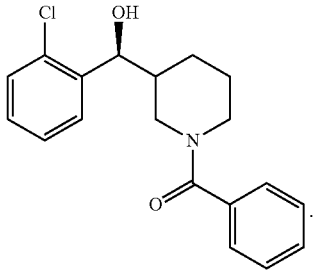 [SMILES: O=C(c1ccccc1)N1CCCC([C@H](O)c2ccccc2Cl)C1]

In some embodiments, compound VII-8 is of formula

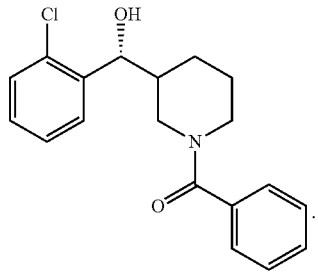

In some embodiments, compound VII-9 is of formula

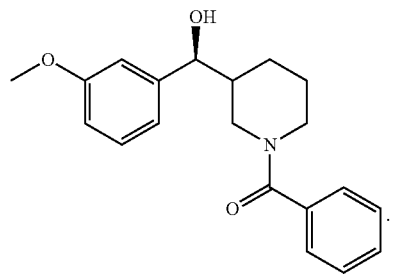 [SMILES: COc1cccc([C@@H](O)C2CCCN(C(=O)c3ccccc3)C2)c1]

In some embodiments, compound VII-9 is of formula

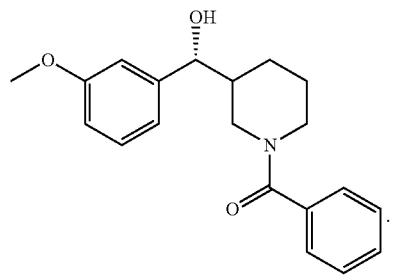 [SMILES: COc1cccc([C@H](O)C2CCCN(C(=O)c3ccccc3)C2)c1]

In some embodiments, compound VII-10 is of formula

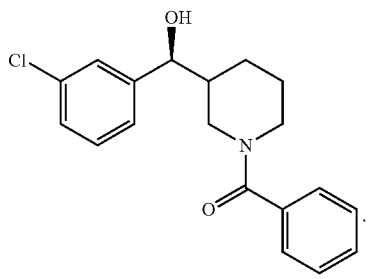 [SMILES: O=C(c1ccccc1)N1CCCC([C@H](O)c2cccc(Cl)c2)C1]

In some embodiments, compound VII-10 is of formula

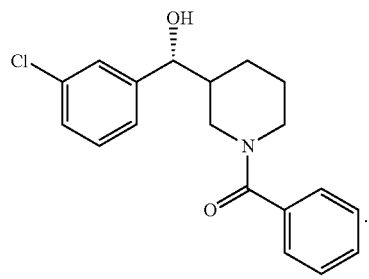 [SMILES: O=C(c1ccccc1)N1CCCC([C@@H](O)c2cccc(Cl)c2)C1]

In some embodiments, compound VII-11 is of formula

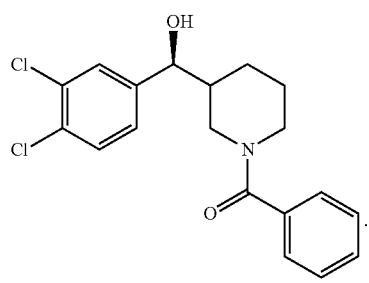 [SMILES: O=C(c1ccccc1)N1CCCC([C@H](O)c2ccc(Cl)c(Cl)c2)C1]

In some embodiments, compound VII-11 is of formula

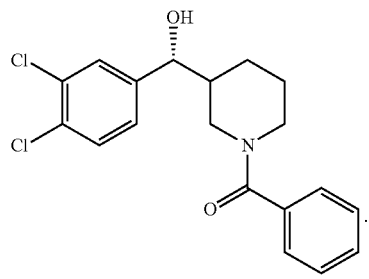 [SMILES: O=C(c1ccccc1)N1CCCC([C@@H](O)c2ccc(Cl)c(Cl)c2)C1]

In some embodiments, compound VII-12 is of formula

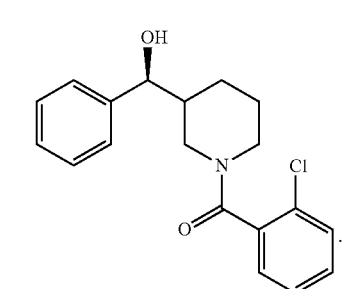

In some embodiments, compound VII-12 is of formula

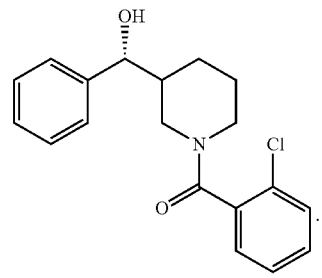

In some embodiments, compound VII-13 is of formula

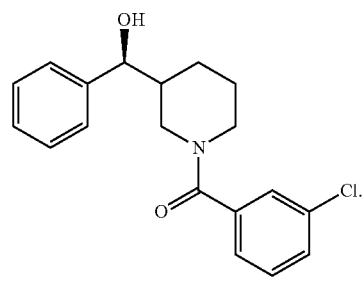 [SMILES: O=C(c1cccc(Cl)c1)N1CCCC([C@H](O)c2ccccc2)C1]

In some embodiments, compound VII-13 is of formula

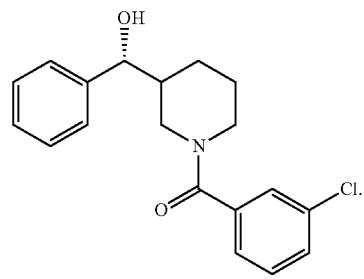 [SMILES: O=C(c1cccc(Cl)c1)N1CCCC([C@@H](O)c2ccccc2)C1]

In some embodiments, compound VII-14 is of formula

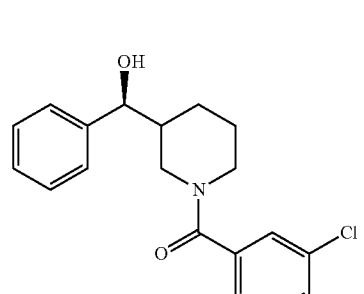

In some embodiments, compound VII-14 is of formula

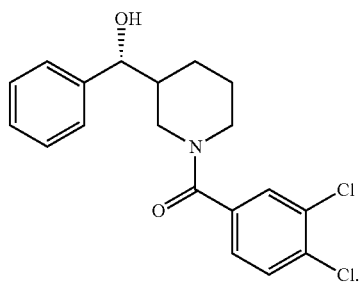 [SMILES: O=C(c1ccc(Cl)c(Cl)c1)N1CCCC([C@@H](O)c2ccccc2)C1]

In some embodiments, compound VII-15 is of formula

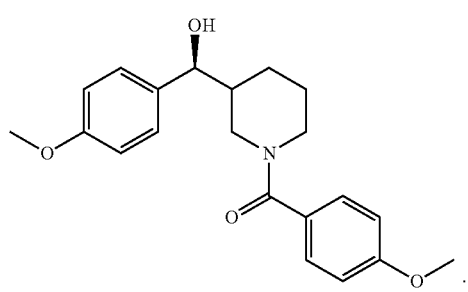

In some embodiments, compound VII-15 is of formula

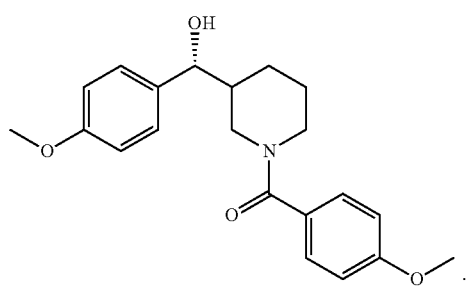

In some embodiments, compound VII-16 is of formula

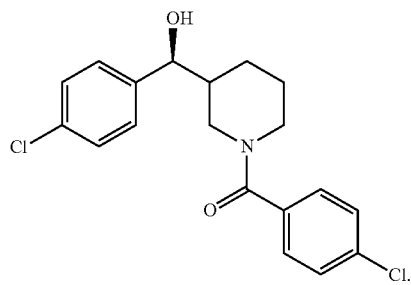 [SMILES: O=C(c1ccc(Cl)cc1)N1CCCC([C@H](O)c2ccc(Cl)cc2)C1]

In some embodiments, compound VII-16 is of formula

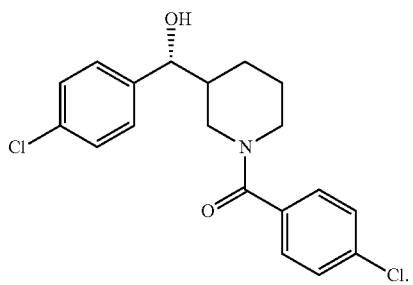 [SMILES: O=C(c1ccc(Cl)cc1)N1CCCC([C@@H](O)c2ccc(Cl)cc2)C1]

In some embodiments, compound VII-17 is of formula

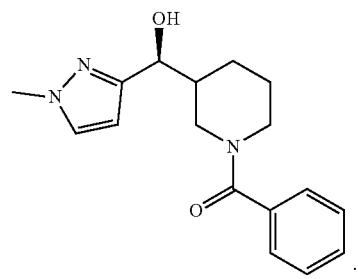

In some embodiments, compound VII-17 is of formula

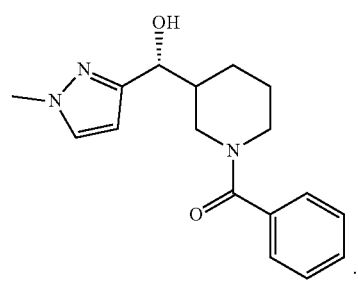 [SMILES: Cn1ccc([C@H](O)C2CCCN(C(=O)c3ccccc3)C2)n1]

In some embodiments, the present invention is compound I-1:

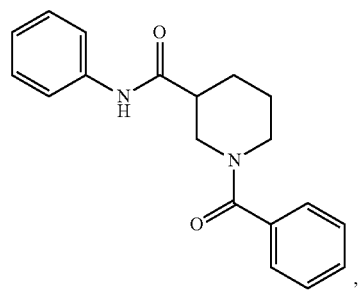 [SMILES: O=C(Nc1ccccc1)C1CCCN(C(=O)c2ccccc2)C1]

or a pharmaceutically acceptable salt thereof.

In some embodiments, the compound of the present invention is other than a compound in Table A.

TABLE A
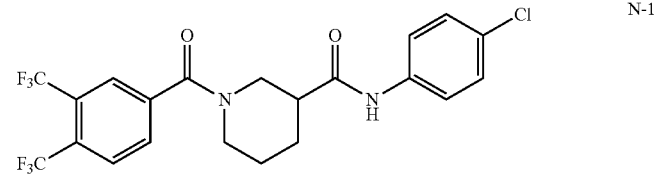
N-1
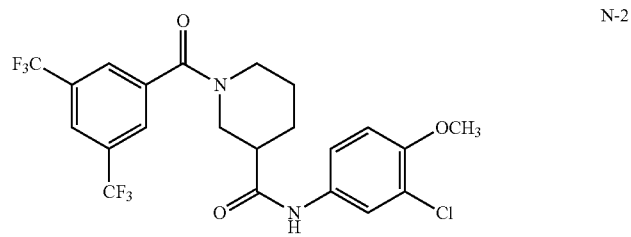
N-2
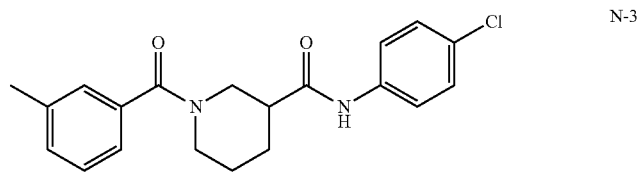
N-3
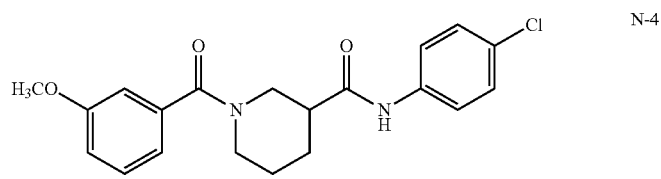
N-4
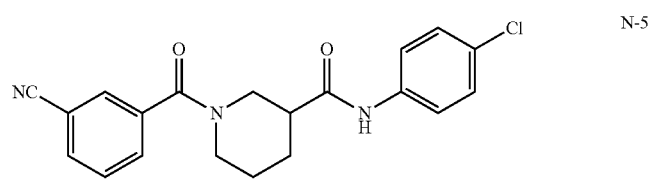
N-5
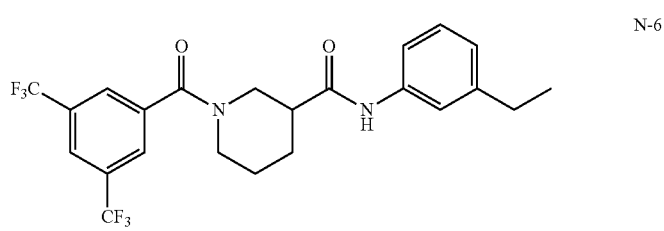
N-6
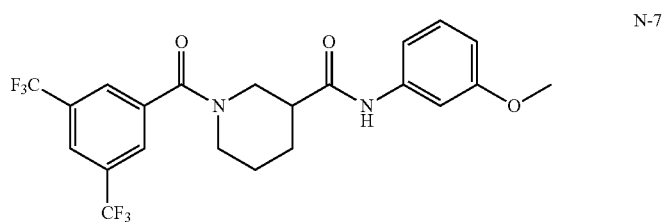
N-7

TABLE A-continued
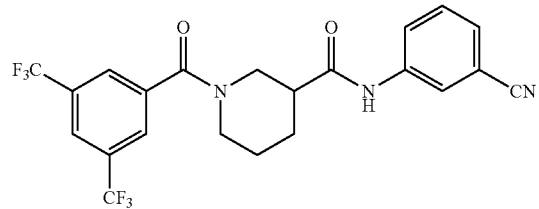 [SMILES: N#Cc1cccc(NC(=O)C2CCCN(C(=O)c3cc(C(F)(F)F)cc(C(F)(F)F)c3)C2)c1] N-8
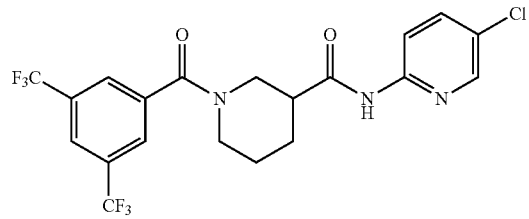 [SMILES: O=C(Nc1ccc(Cl)cn1)C1CCCN(C(=O)c2cc(C(F)(F)F)cc(C(F)(F)F)c2)C1] N-9
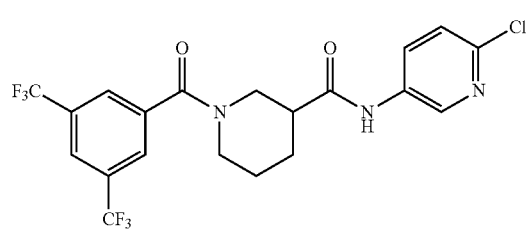 [SMILES: O=C(Nc1ccc(Cl)nc1)C1CCCN(C(=O)c2cc(C(F)(F)F)cc(C(F)(F)F)c2)C1] N-10
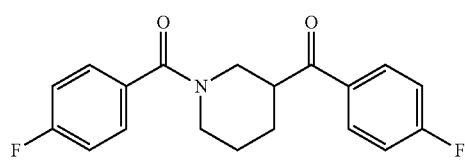 [SMILES: O=C(c1ccc(F)cc1)C1CCCN(C(=O)c2ccc(F)cc2)C1] N-11
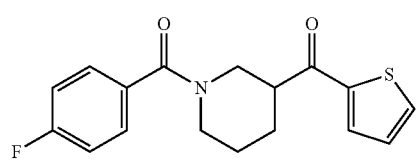 N-12
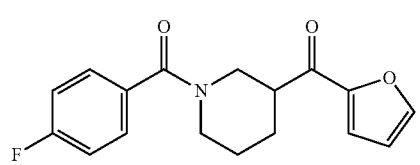 [SMILES: O=C(c1ccco1)C1CCCN(C(=O)c2ccc(F)cc2)C1] N-13
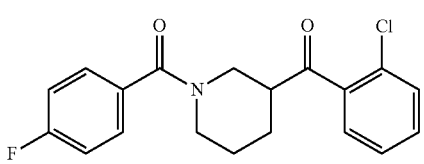 [SMILES: O=C(c1ccccc1Cl)C1CCCN(C(=O)c2ccc(F)cc2)C1] N-14
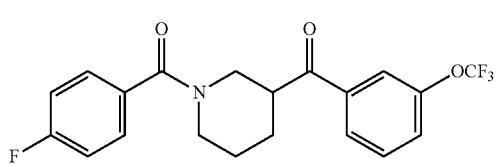 [SMILES: O=C(c1cccc(OC(F)(F)F)c1)C1CCCN(C(=O)c2ccc(F)cc2)C1] N-15

TABLE A-continued
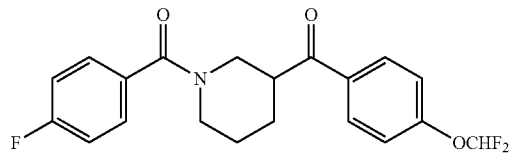 [SMILES: O=C(c1ccc(OC(F)F)cc1)C1CCCN(C(=O)c2ccc(F)cc2)C1]
N-16
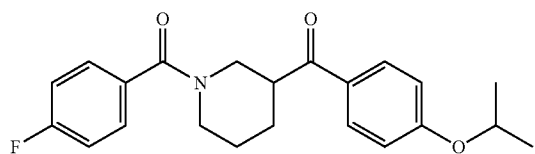 [SMILES: CC(C)Oc1ccc(C(=O)C2CCCN(C(=O)c3ccc(F)cc3)C2)cc1]
N-17
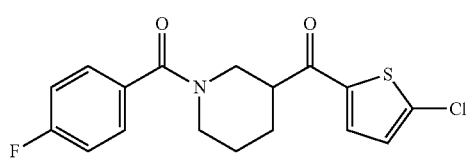 [SMILES: O=C(c1ccc(Cl)s1)C1CCCN(C(=O)c2ccc(F)cc2)C1]
N-18
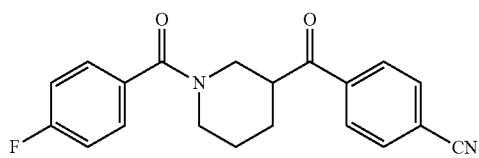 [SMILES: N#Cc1ccc(C(=O)C2CCCN(C(=O)c3ccc(F)cc3)C2)cc1]
N-19
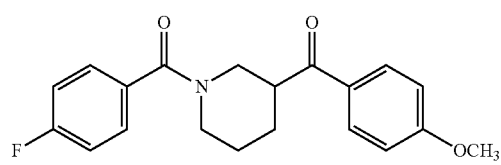 [SMILES: COc1ccc(C(=O)C2CCCN(C(=O)c3ccc(F)cc3)C2)cc1]
N-20
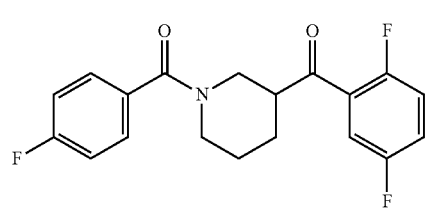 [SMILES: O=C(c1cc(F)ccc1F)C1CCCN(C(=O)c2ccc(F)cc2)C1]
N-21
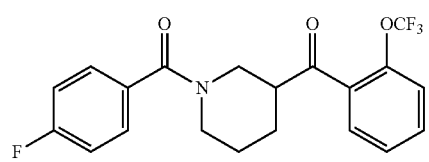 [SMILES: O=C(c1ccccc1OC(F)(F)F)C1CCCN(C(=O)c2ccc(F)cc2)C1]
N-22
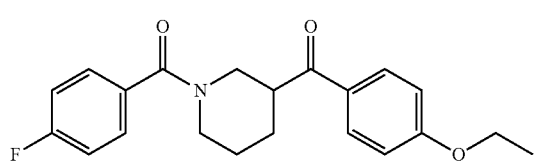 [SMILES: CCOc1ccc(C(=O)C2CCCN(C(=O)c3ccc(F)cc3)C2)cc1]
N-23
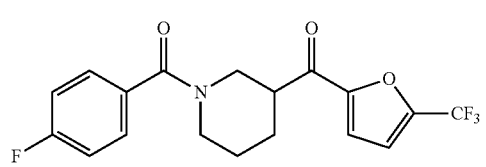 [SMILES: O=C(c1ccc(C(F)(F)F)o1)C1CCCN(C(=O)c2ccc(F)cc2)C1]
N-24

TABLE A-continued
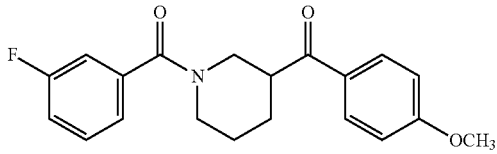 [SMILES: COc1ccc(C(=O)C2CCCN(C(=O)c3cccc(F)c3)C2)cc1] N-25
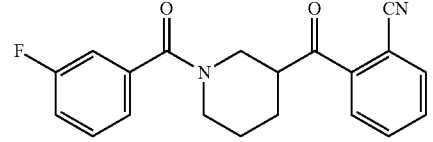 [SMILES: N#Cc1ccccc1C(=O)C1CCCN(C(=O)c2cccc(F)c2)C1] N-26
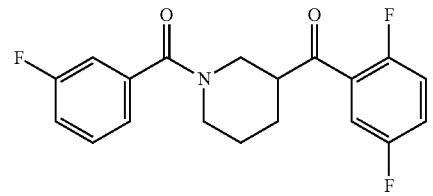 [SMILES: O=C(c1cc(F)ccc1F)C1CCCN(C(=O)c2cccc(F)c2)C1] N-27
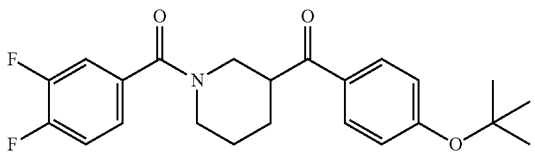 [SMILES: CC(C)(C)Oc1ccc(C(=O)C2CCCN(C(=O)c3ccc(F)c(F)c3)C2)cc1] N-28
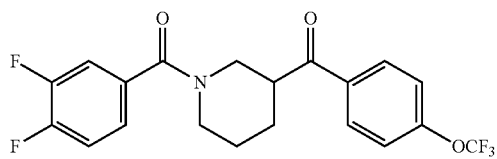 [SMILES: O=C(c1ccc(OC(F)(F)F)cc1)C1CCCN(C(=O)c2ccc(F)c(F)c2)C1] N-29
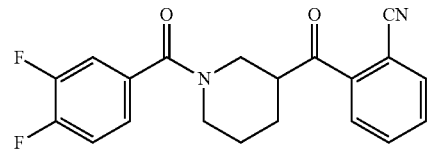 [SMILES: N#Cc1ccccc1C(=O)C1CCCN(C(=O)c2ccc(F)c(F)c2)C1] N-30
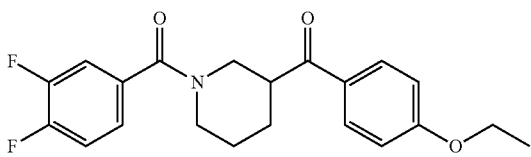 [SMILES: CCOc1ccc(C(=O)C2CCCN(C(=O)c3ccc(F)c(F)c3)C2)cc1] N-31
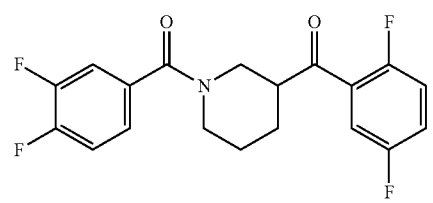 [SMILES: O=C(c1cc(F)ccc1F)C1CCCN(C(=O)c2ccc(F)c(F)c2)C1] N-32
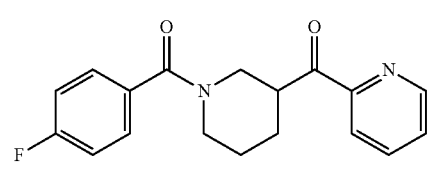 [SMILES: O=C(c1ccccn1)C1CCCN(C(=O)c2ccc(F)cc2)C1] N-33

TABLE A-continued
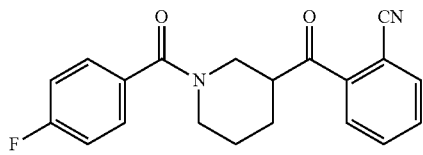 [SMILES: N#Cc1ccccc1C(=O)C1CCCN(C(=O)c2ccc(F)cc2)C1] N-34
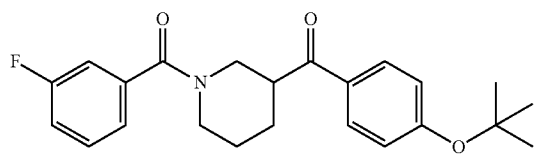 [SMILES: CC(C)(C)Oc1ccc(C(=O)C2CCCN(C(=O)c3cccc(F)c3)C2)cc1] N-35
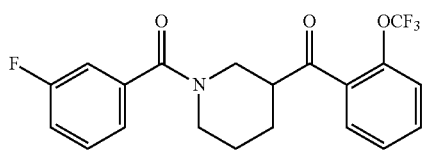 [SMILES: O=C(c1ccccc1OC(F)(F)F)C1CCCN(C(=O)c2cccc(F)c2)C1] N-36
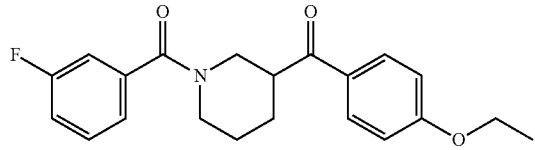 [SMILES: CCOc1ccc(C(=O)C2CCCN(C(=O)c3cccc(F)c3)C2)cc1] N-37
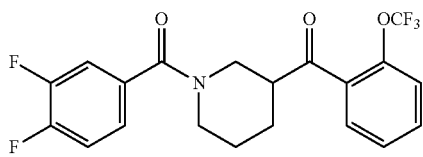 [SMILES: O=C(c1ccccc1OC(F)(F)F)C1CCCN(C(=O)c2ccc(F)c(F)c2)C1] N-38
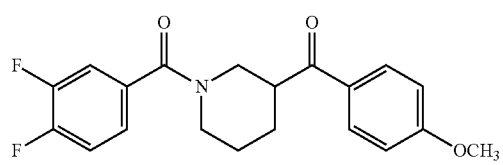 [SMILES: COc1ccc(C(=O)C2CCCN(C(=O)c3ccc(F)c(F)c3)C2)cc1] N-39
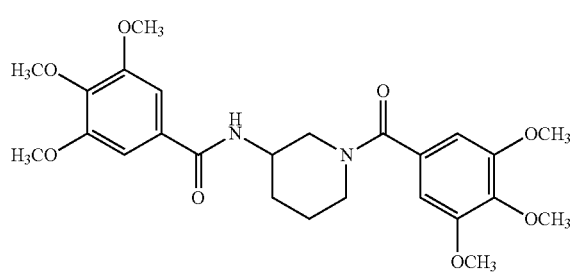 [SMILES: COc1cc(C(=O)NC2CCCN(C(=O)c3cc(OC)c(OC)c(OC)c3)C2)cc(OC)c1OC] N-40
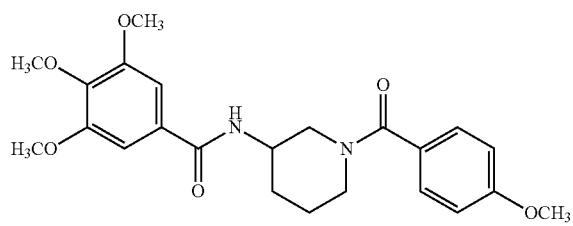 [SMILES: COc1ccc(C(=O)N2CCCC(NC(=O)c3cc(OC)c(OC)c(OC)c3)C2)cc1] N-41

TABLE A-continued
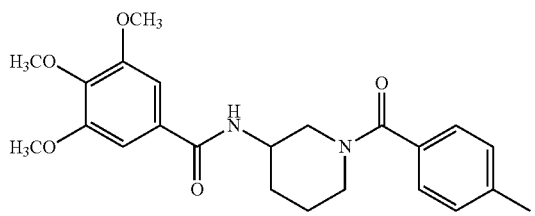 [SMILES: COc1cc(C(=O)NC2CCCN(C(=O)c3ccc(C)cc3)C2)cc(OC)c1OC]
N-42
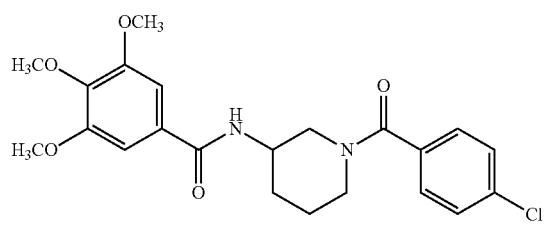 [SMILES: COc1cc(C(=O)NC2CCCN(C(=O)c3ccc(Cl)cc3)C2)cc(OC)c1OC]
N-43
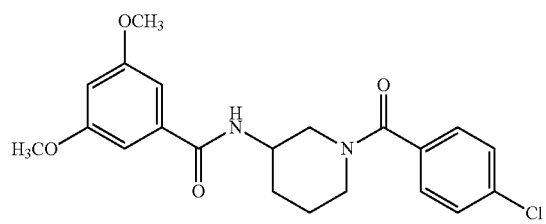 [SMILES: COc1cc(OC)cc(C(=O)NC2CCCN(C(=O)c3ccc(Cl)cc3)C2)c1]
N-44
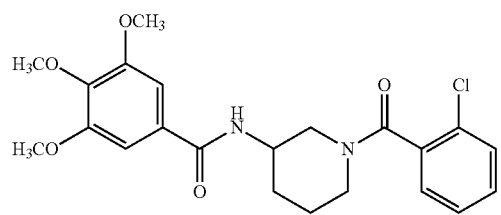 [SMILES: COc1cc(C(=O)NC2CCCN(C(=O)c3ccccc3Cl)C2)cc(OC)c1OC]
N-45
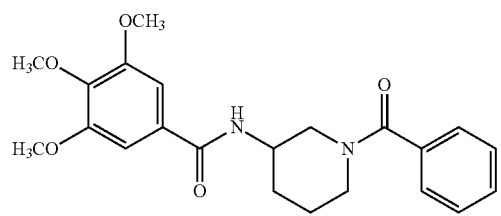 [SMILES: COc1cc(C(=O)NC2CCCN(C(=O)c3ccccc3)C2)cc(OC)c1OC]
N-46
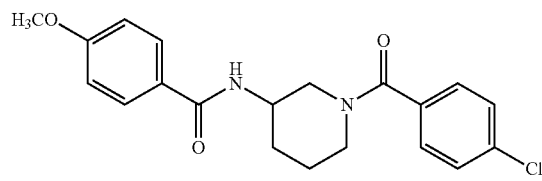 [SMILES: COc1ccc(C(=O)NC2CCCN(C(=O)c3ccc(Cl)cc3)C2)cc1]
N-47
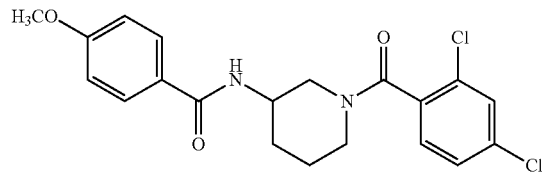 [SMILES: COc1ccc(C(=O)NC2CCCN(C(=O)c3ccc(Cl)cc3Cl)C2)cc1]
N-48

TABLE A-continued
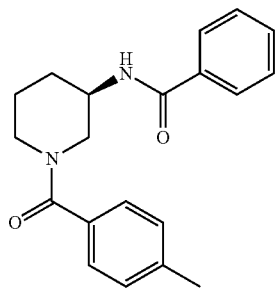 [SMILES: Cc1ccc(C(=O)N2CCC[C@@H](NC(=O)c3ccccc3)C2)cc1]
N-49
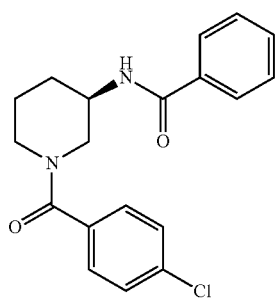 [SMILES: O=C(N[C@@H]1CCCN(C(=O)c2ccc(Cl)cc2)C1)c1ccccc1]
N-50
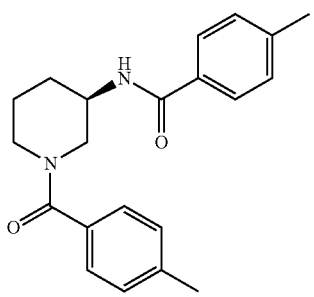 [SMILES: Cc1ccc(C(=O)N[C@@H]2CCCN(C(=O)c3ccc(C)cc3)C2)cc1]
N-51
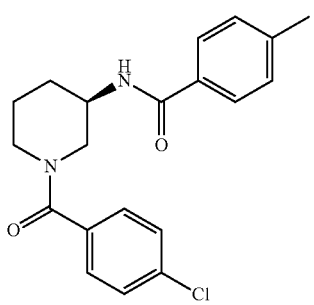 [SMILES: Cc1ccc(C(=O)N[C@@H]2CCCN(C(=O)c3ccc(Cl)cc3)C2)cc1]
N-52
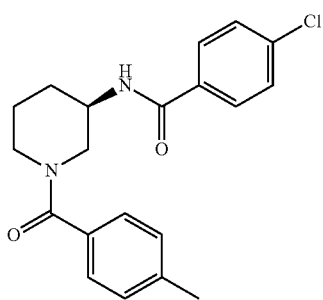 [SMILES: Cc1ccc(C(=O)N2CCC[C@@H](NC(=O)c3ccc(Cl)cc3)C2)cc1]
N-53

TABLE A-continued
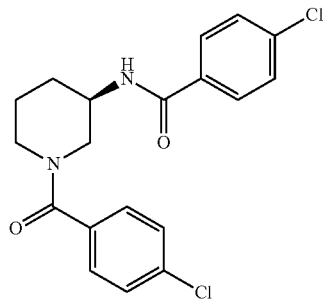 [SMILES: O=C(N[C@@H]1CCCN(C(=O)c2ccc(Cl)cc2)C1)c1ccc(Cl)cc1]
N-54
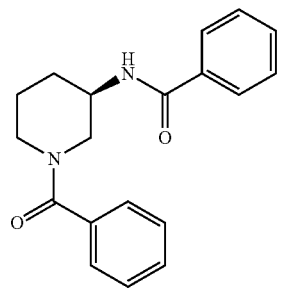 [SMILES: O=C(N[C@@H]1CCCN(C(=O)c2ccccc2)C1)c1ccccc1]
N-55
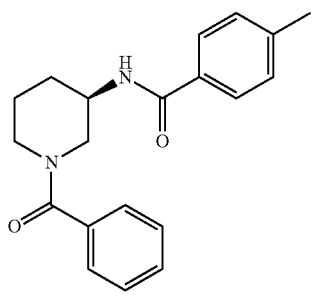 [SMILES: Cc1ccc(C(=O)N[C@@H]2CCCN(C(=O)c3ccccc3)C2)cc1]
N-56
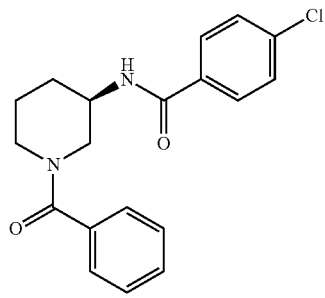 [SMILES: O=C(N[C@@H]1CCCN(C(=O)c2ccccc2)C1)c1ccc(Cl)cc1]
N-57
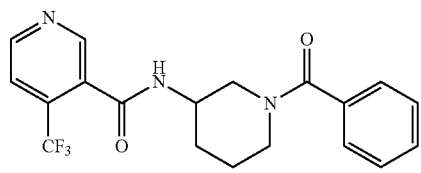 [SMILES: O=C(NC1CCCN(C(=O)c2ccccc2)C1)c1cnccc1C(F)(F)F]
N-58

TABLE A-continued

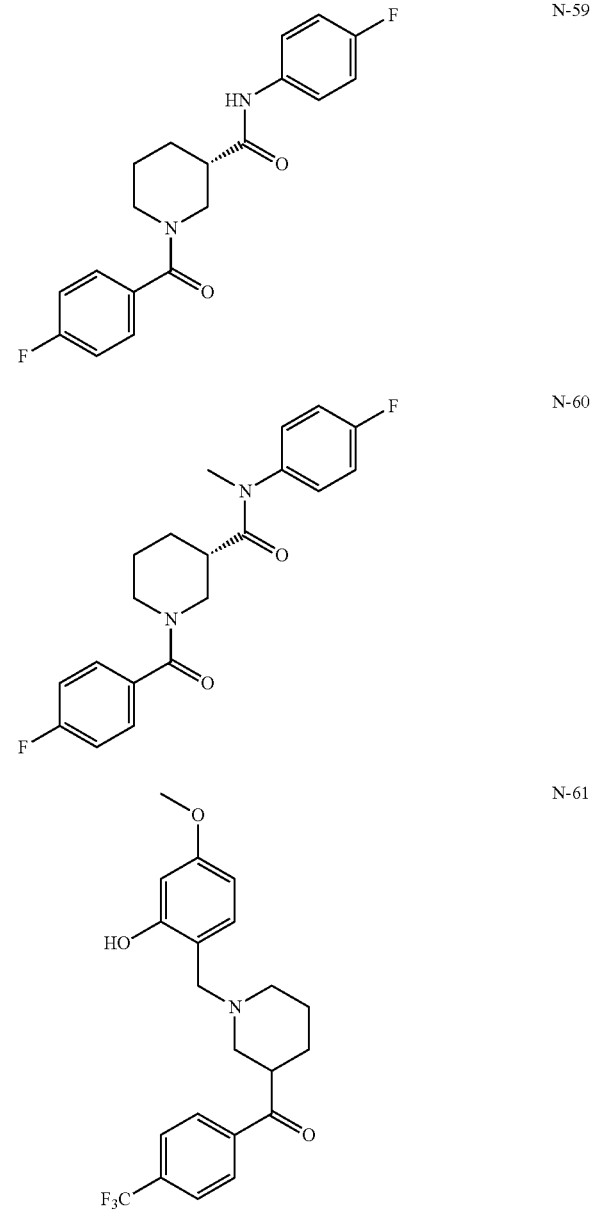

II. Pharmaceutically Acceptable Compositions

According to another embodiment, the invention provides a composition comprising a compound of this invention or a pharmaceutically acceptable salt thereof, and a pharmaceutically acceptable carrier, adjuvant, or vehicle. The amount of compound in compositions of this invention is such that is effective to measurably modulate the interaction between TCR and Nck, in a biological sample or in a patient. In certain embodiments, the amount of compound in compositions of this invention is such that is effective to measurably modulate the interaction between TCR and Nck in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants, or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see supra) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well-known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

III. Uses of Compounds and Pharmaceutically Acceptable Compositions

Compounds and compositions described herein are generally useful for the modulation of TCR signaling and T-cell activation via modulation of the interaction between TCR and Nck.

The activity of a compound utilized in this invention as a modulator of the TCR-Nck interaction, may be assayed in vitro, in vivo or in a cell line. In vitro assays include, for example, assays that measure the proliferation of T-lymphocytes (e.g., Tse, W. T. et al., Transplantation, 2003, 75(3): 389-97, whose contents is incorporated herein in its entirety by reference); measure the polymerization of the actin cytoskeleton induced in T-cells after TCR stimulation (e.g., Fuller, C. L. et al., Immunol. Rev. 2003, 292: 220-36, whose contents is incorporated herein in its entirety by reference); and measure the secretion of cytokines by T-cells caused by stimulation of the TCR (e.g., Finco, D. et al., Cytokine, 2014, 66(2): 143-55, whose contents is incorporated herein in its entirety by reference). In vivo assays include standard animal models for immune and autoimmune disease, which are well-known and are part of the state of the art such as, for example, delayed hypersensitivity (e.g., Kudlacz, E. et al., Am. J. Transplant., 2004, 4(1): 51-7, whose contents is incorporated herein in its entirety by reference); models for rheumatoid arthritis (e.g., Holmdahl, R. et al., APMIS, 1989, 97(7): 575-84, whose contents is incorporated herein in its entirety by reference); models of multiple sclerosis (experimental autoimmune encephalomyelitis) (e.g., Gonzalez-Rey, E. et al., Am. J. Pathol. 2006, 168(4): 1179-88, whose contents is incorporated herein in its entirety by reference; and models of transplant rejection (see, e.g., various animal models described in the references above in relation to the treatment of transplant rejection, incorporated here by reference).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are modulators of the TCR-Nck interaction and are therefore useful for treating one or more disorders associated with activity of TCR. Thus, in certain embodiments, the present invention provides a method for treating a TCR-Nck mediated disorder comprising the step of administering to a patient in need thereof a compound of the present invention, or pharmaceutically acceptable composition thereof.

As used herein, the terms "TCR-Nck mediated" disorders, diseases, and/or conditions means any disease, or other deleterious condition, in which the TCR is known to play a role. Accordingly, another embodiment of the present invention relates to treating or lessening the severity of one or more diseases in which TCR is known to play a role. Such TCT-Nck mediated disorders include, without limitation, autoimmune and inflammatory disorders; disorders associated with transplantation; proliferative disorders; and neurological disorders. (See, e.g., O'Sea, J. et al., Nat. Rev. Drug Doscpv. 2004, 3(7): 555-64; Cetkovic-Cvrlje, M. et al., Curr. Pharm. Des. 2004, 10(15): 1767-84; Cetkovic-Cvrlje, M. et al., Arch. Immunol. Ther. Exp. 2004, 52(2): 69-82).

In some embodiments, the present invention provides a method for treating a disorder mediated by TCR-Nck interaction in a patient in need thereof, comprising the step of administering to said patient a compound according to the present invention or pharmaceutically acceptable composition thereof. In some embodiments, the method of modulating TCR-Nck is used to treat autoimmune and inflammatory disorders; disorders associated with transplantation; proliferative disorders; and neurological disorders. In some embodiments, an autoimmune and inflammatory disorder, a disorder associated with transplantation, a proliferative disorder, and a neurological disorder is selected from the disease/disorder as described herein.

In some embodiments, the method of modulating TCR-Nck is used to treat alopecia areata. (See, e.g., Petukhova, L. et al., Nature, 2010, 466(7302): 113-17). Accordingly, in some embodiments, the present invention provides a method of treating alopecia areata, in a patient in need thereof, comprising the step of administering to said patient a provided compound or a pharmaceutically acceptable salt thereof.

In some embodiments, the method of modulating TCR-Nck is used to treat ankylosing spondylitis. (See, e.g., Smith, J. A., Curr Allergy Asthma Rep. 2015, 15(1): 489). Accordingly, in some embodiments, the present invention provides a method of treating ankylosing spondylitis, in a patient in need thereof, comprising the step of administering to said patient a provided compound or a pharmaceutically acceptable salt thereof.

In some embodiments, the method of modulating TCR-Nck is used to treat asthma. (See, e.g., Robinson, D. S., J. Allergy Clin. Immunol., 2010, 126(6): 1081-91). Accordingly, in some embodiments, the present invention provides a method of treating asthma, in a patient in need thereof, comprising the step of administering to said patient a provided compound or a pharmaceutically acceptable salt thereof.

In some embodiments, the method of modulating TCR-Nck is used to treat autoimmune hepatitis. (See, e.g., Manns, M. P. et al., Hepatology, 2010, 51(6), 2193-213. Accordingly, in some embodiments, the present invention provides a method of treating autoimmune hepatitis, in a patient in need thereof, comprising the step of administering to said patient a provided compound or a pharmaceutically acceptable salt thereof.

In some embodiments, the method of modulating TCR-Nck is used to treat autoimmune lymphoproliferative syndrome (ALPS). (See, e.g., Sneller, M. C. et al., Curr. Opin. Rheumatology, 2003, 15(4) 417-21). Accordingly, in some embodiments, the present invention provides a method of treating ALPS, in a patient in need thereof, comprising the step of administering to said patient a provided compound or a pharmaceutically acceptable salt thereof.

In some embodiments, the method of modulating TCR-Nck is used to autoimmune myocarditis. (See, e.g., Caforio, A. L. and Iliceto, S., Curr. Opin. Cardiol., 2008, 23(3): 219-26). Accordingly, in some embodiments, the present invention provides a method of treating autoimmune myocarditis, in a patient in need thereof, comprising the step of administering to said patient a provided compound or a pharmaceutically acceptable salt thereof.

In some embodiments, the method of modulating TCR-Nck is used to autoimmune orchitis. (See, e.g., Silva, C. A. et al., Autoimmun Rev., 2014, 13(4-5): 431-34). Accordingly, in some embodiments, the present invention provides a method of treating autoimmune orchitis, in a patient in need thereof, comprising the step of administering to said patient a provided compound or a pharmaceutically acceptable salt thereof.

In some embodiments, the method of modulating TCR-Nck is used to autoimmune pancreatitis. (See, e.g., Fan, B. G. and Andren-Sandberg, A., N. Am. J. Med. Sci. 2009, 1(2): 148-51). Accordingly, in some embodiments, the present invention provides a method of treating autoimmune pancreatitis, in a patient in need thereof, comprising the step of administering to said patient a provided compound or a pharmaceutically acceptable salt thereof.

In some embodiments, the method of modulating TCR-Nck is used to treat atopic dermatitis. (See, e.g., Nograles, K. E. et al., J. Allergy Clin. Immunol., 2009, 123(6): 1244-52). Accordingly, in some embodiments, the present invention provides a method of treating systemic atopic dermatitis, in a patient in need thereof, comprising the step of administering to said patient a provided compound or a pharmaceutically acceptable salt thereof.

In some embodiments, the method of modulating TCR-Nck is used to treat Behçet's disease. (See, e.g., Direskeneli, H., Genetics Research International, 2013, Article ID 249157 doi:10.1155/2013/249157). Accordingly, in some embodiments, the present invention provides a method of treating Behçet's disease, in a patient in need thereof, comprising the step of administering to said patient a provided compound or a pharmaceutically acceptable salt thereof.

In some embodiments, the method of modulating TCR-Nck is used to treat Castleman disease. (See, e.g., Al-Maghrabi, J. et al., Histopathology, 2005, 48(3): 233-38). Accordingly, in some embodiments, the present invention provides a method of treating Castleman disease, in a patient in need thereof, comprising the step of administering to said patient a provided compound or a pharmaceutically acceptable salt thereof.

In some embodiments, the method of modulating TCR-Nck is used to treat Celiac disease. (See, e.g., Mazzarella, G., World J. Gastroenterol., 2015, 21(24): 7349-56). Accordingly, in some embodiments, the present invention provides a method of treating Celiac disease, in a patient in need thereof, comprising the step of administering to said patient a provided compound or a pharmaceutically acceptable salt thereof.

In some embodiments, the method of modulating TCR-Nck is used to treat chronic inflammatory demyelinating polyneuropathy. (See, e.g., Notturno, F. et al., J. Neuroimmunol. 2008, 197(2): 124-7). Accordingly, in some embodiments, the present invention provides a method of treating chronic inflammatory demyelinating polyneuropathy, in a patient in need thereof, comprising the step of administering to said patient a provided compound or a pharmaceutically acceptable salt thereof.

In some embodiments, the method of modulating TCR-Nck is used to treat Cogan's syndrome. (See, e.g., Greco, A. et al., Autoimmunity Rev. 2013, 12(3): 396-400). Accordingly, in some embodiments, the present invention provides a method of treating Cogan's syndrome, in a patient in need thereof, comprising the step of administering to said patient a provided compound or a pharmaceutically acceptable salt thereof.

In some embodiments, the method of modulating TCR-Nck is used to treat Churg-Strauss syndrome. (See, e.g., Guida, G. et al., Clin. Immunol., 2008 128(1): 94-102). Accordingly, in some embodiments, the present invention provides a method of treating Churg-Strauss syndrome, in a patient in need thereof, comprising the step of administering to said patient a provided compound or a pharmaceutically acceptable salt thereof.

In some embodiments, the method of modulating TCR-Nck is used to treat Crohn's disease. (See, e.g., Roche, J. K. et al., J. Clin. Invest. 1985, 75(2):522-530; Marks, D. J. and Segal, A. W. J. Pathol. 2008, 214(2): 260-66; Cobrin, G. M. and Abreu, M. T. Immunol. Rev. 2005, 206(1): 277-95). Accordingly, in some embodiments, the present invention provides a method of treating Crohn's disease, in a patient in need thereof, comprising the step of administering to said patient a provided compound or a pharmaceutically acceptable salt thereof.

In some embodiments, the method of modulating TCR-Nck is used to treat Evans syndrome. (See, e.g., Teachery, D. T. et al., Blood, 2004, 105(6):2443-48). Accordingly, in some embodiments, the present invention provides a method of treating Evans syndrome, in a patient in need thereof, comprising the step of administering to said patient a provided compound or a pharmaceutically acceptable salt thereof.

In some embodiments, the method of modulating TCR-Nck is used to treat inclusion body myositis. (See, e.g., Kitazawa, M. et al., J. Neuroscience, 2009, 29(19): 6132-41). Accordingly, in some embodiments, the present invention provides a method of treating inclusion body myositis, in a patient in need thereof, comprising the step of administering to said patient a provided compound or a pharmaceutically acceptable salt thereof.

In some embodiments, the method of modulating TCR-Nck is used to treat inflammatory bowel disease. (See, e.g., Zenewicz, L. A. et al., Trends Mol. Med., 2009, 15(5): 199-207). Accordingly, in some embodiments, the present invention provides a method of treating inflammatory bowel disease, in a patient in need thereof, comprising the step of administering to said patient a provided compound or a pharmaceutically acceptable salt thereof.

In some embodiments, the method of modulating TCR-Nck is used to treat Kawasaki disease. (See, e.g., Onouchi, Y. et al., Nature Genetics, 2008, 40: 35-42). Accordingly, in some embodiments, the present invention provides a method of treating Kawasaki disease, in a patient in need thereof, comprising the step of administering to said patient a provided compound or a pharmaceutically acceptable salt thereof.

In some embodiments, the method of modulating TCR-Nck is used to treat Lyme disease (chronic). (See, e.g., Singh, S. K. and Girschick, H. J. Paediatric Rheumatology, 2004, 10(7): 598-614; Raveche, E. S. et al., J. Clin. Microbiol. 2005, 43(2): 850-56). Accordingly, in some embodiments, the present invention provides a method of treating Lyme disease (chronic), in a patient in need thereof, comprising the step of administering to said patient a provided compound or a pharmaceutically acceptable salt thereof.

In some embodiments, the method of modulating TCR-Nck is used to treat multiple sclerosis. (See, e.g., Babbe, H. et al., J. Exp. Med., 2000, 192(3): 393-404; Dai, K. Z. et al., Genes Immun. 2001, 2(5): 263-8). Accordingly, in some embodiments, the present invention provides a method of treating multiple sclerosis, in a patient in need thereof, comprising the step of administering to said patient a provided compound or a pharmaceutically acceptable salt thereof.

In some embodiments, the method of modulating TCR-Nck is used to treat myasthenia gravis. (See, e.g., Meriggioli, M. N. and Sanders, D. B. S., Lancet Neurology, 2009, 8(5): 475-90). Accordingly, in some embodiments, the present invention provides a method of treating myasthenia gravis, in a patient in need thereof, comprising the step of administering to said patient a provided compound or a pharmaceutically acceptable salt thereof.

In some embodiments, the method of modulating TCR-Nck is used to treat psoriasis. (See, e.g., Cai, Y. et al., Cell Mol. Immunol., 2012, 9(4): 302-09). Accordingly, in some embodiments, the present invention provides a method of treating psoriasis, in a patient in need thereof, comprising the step of administering to said patient a provided compound or a pharmaceutically acceptable salt thereof.

In some embodiments, the method of modulating TCR-Nck is used to treat psoriatic arthritis. (See, e.g., Choy, E., Curr. Rheumatol. Rep. Exp., 2007, 9(6): 437-41). Accordingly, in some embodiments, the present invention provides a method of treating psoriatic arthritis, in a patient in need thereof, comprising the step of administering to said patient a provided compound or a pharmaceutically acceptable salt thereof.

In some embodiments, the method of modulating TCR-Nck is used to treat rheumatoid arthritis. (See, e.g., Cope, A. P. et al., Clin. Exp. Rheumatol., 2007, 25(5): S4-11). Accordingly, in some embodiments, the present invention provides a method of treating rheumatoid arthritis, in a patient in need thereof, comprising the step of administering to said patient a provided compound or a pharmaceutically acceptable salt thereof.

In some embodiments, the method of modulating TCR-Nck is used to treat systemic lupus erythematosus. (See, e.g., Crispin, J. C. et al., J. Immunol., 2008, 181(12): 8761-66; Linterman, M. A. et al., J. Exp. Med. 2009, 206(3): 561-76). Accordingly, in some embodiments, the present invention provides a method of treating systemic lupus erythematosus, in a patient in need thereof, comprising the step of administering to said patient a provided compound or a pharmaceutically acceptable salt thereof.

In some embodiments, the method of modulating TCR-Nck is used to treat type I diabetes. (See, e.g., Roep, B. O., Diabetologia, 46(3): 305-21). Accordingly, in some embodiments, the present invention provides a method of treating type I diabetes, in a patient in need thereof, comprising the step of administering to said patient a provided compound or a pharmaceutically acceptable salt thereof.

In some embodiments, the method of modulating TCR-Nck is used to treat ulcerative colitis. (See, e.g., Kappeler, A. and Mueller, C., Histol Histopathol., 2000, 15(1): 167-72). Accordingly, in some embodiments, the present invention provides a method of treating ulcerative colitis, in a patient in need thereof, comprising the step of administering to said patient a provided compound or a pharmaceutically acceptable salt thereof.

In some embodiments, the method of modulating TCR-Nck is used to treat uveitis. (See, e.g., Horai, R. et al., Immunity, 2015, 43(2): 343-53). Accordingly, in some embodiments, the present invention provides a method of treating uveitis, in a patient in need thereof, comprising the step of administering to said patient a provided compound or a pharmaceutically acceptable salt thereof.

In some embodiments, the method of modulating TCR-Nck is used to treat vitiligo. (See, e.g., Van den Wijngaard, R. et al., Lab Invest. 2000, 80(8): 1299-309). Accordingly, in some embodiments, the present invention provides a method of treating vitiligo, in a patient in need thereof, comprising the step of administering to said patient a provided compound or a pharmaceutically acceptable salt thereof.

In some embodiments, the method of modulating TCR-Nck is used to treat rejection of transplants. (See, e.g., Issa, F. et al., Expert Rev. Clin. Immunol. 2010, 6(1): 155-69). Accordingly, in some embodiments, the present invention provides a method of treating rejection of transplants, in a patient in need thereof, comprising the step of administering to said patient a provided compound or a pharmaceutically acceptable salt thereof.

In some embodiments, the method of modulating TCR-Nck is used to treat granulomatosis with polyangiitis (Wegener's granulomatosis). (See, e.g., Morgan, M. D. et al., Arthritis & Rheumatism, 2011, 63(7): 2127-37). Accordingly, in some embodiments, the present invention provides a method of treating granulomatosis with polyangiitis (Wegener's granulomatosis), in a patient in need thereof, comprising the step of administering to said patient a provided compound or a pharmaceutically acceptable salt thereof.

In some embodiments, the method of modulating TCR-Nck is used to treat hematological cancer. Accordingly, in some embodiments, the present invention provides a method of treating hematological cancer, in a patient in need thereof, comprising the step of administering to said patient a provided compound or a pharmaceutically acceptable salt thereof.

In some embodiments, the method of modulating TCR-Nck is used to treat transplant rejection. (See, e.g., Issa, F. et al., Expert Rev. Clin. Immunol. 2010, 6(1): 155-69). In some embodiments, the method of modulating TCR-Nck is used to treat graft-versus-host disease. (See, e.g., W. D., Nature Rev. Immunology, 2007, 7: 340-52). Accordingly, in some embodiments, the present invention provides a method of treating a disorder associated with transplantation, in a patient in need thereof, comprising the step of administering to said patient a provided compound or a pharmaceutically acceptable salt thereof.

Autoimmune and Inflammatory Disorders

As used herein, "autoimmune and inflammatory disorder" refers to those diseases, illnesses, or conditions engendered when the host's systems are attacked by the host's own immune system. The targets of autoimmune interaction can range anywhere from the cellular level (e.g., myelin basic protein in multiple sclerosis, or the thyrotropin receptor in Graves' disease) to organ specific effects in rheumatoid arthritis or Crohn's disease to system wide effects as seen in systemic lupus erythematosus. Some of the events that have been postulated in the causation of autoimmune diseases have included cytokine over expression, for example TNF-α, IL-2, or IL-2 receptor in inflammatory bowel disease, or under expression (IL-10 under expression in Type 1 diabetes), to defects in allele expression (HLA Class I B27 in ankylosing spondylitis), to altered expression of apoptosis proteins (under expression of Fas in autoimmune lymphoproliferative syndrome type I (ALPS 1). See "Harrison's Principles of Internal Medicine", 16th ed., McGraw-Hill, N.Y., 2005; Chapter 295 for additional information on autoimmune diseases.

In certain embodiments, the autoimmune or inflammatory disorder is Addison's disease, agammaglobulinemia, alopecia areata, alopecia universalis, amyloidosis, ankylosing spondylitis, anti-GBM/anti-TBM nephritis, antiphospholipid syndrome, autoimmune angioedema, autoimmune dysautonomia, autoimmune encelphalomyelitis, autoimmune hepatitis, autoimmune inner ear disease (Meniere's disease), autoimmune myocarditis, autoimmune pancreatitis, autoimmune retinopathy, autoimmune urticarial, axon and neuronal neropathy, Baló disease, Behget's disease, benign mucosal pemphigoid, bullous pemhigoid, Castleman disease, Celiac disease, Chagasa disease, chronic inflammatory demyelination polyneuropathy, chronic recurrent multifocal osteomyelitis, Churg-Strauss, cicatrical pemphioid, Cogan's syndrome, cold agglutinin disease, congenital heart block, Coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, essential mixed cryoglobulinemia, Evan's syndrome, fibromyalgia, fibrosing alveolitis, giant cell arteritis, giant cell myocarditis, glomerulonephritis, Goodpasture's syndrome, granulomatosis with polyangitis, Grave's disease, Guillain-Barre Syndrome, Hashimoto's thyroiditis, hemolytic anemia, Henoch-Schonlein purpura, herpes gestationis or pemphigoid gestationis, hypogammalglobulinemia, IgA nephropathy, IgG4-related sclerosing disease, immune thrombocytopenic purpura, inclusion body myositis, inflammatory bowel disease, interstitial cystitis, juvenile arthritis, juvenile diabetes, juvenile myositis, Kawasaki disease, Lambert-Eaton syndrome, leukocytoclasic vasculitis, lichen planus, lichen sclerosis, ligneous conjunctivitis, linear IgA disease, lupus erythematosus, Lyme disease chronic, Lyme neuroborreliosis, microscopic polyangitis, mixed connective tissue disease, Mooren's ulcer, Mucha-Habermann disease, multiple sclerosis, myasthenia gravis, myositis, neuromyelitis optica, neutropenia, ocular cicatricial pemphigold, optic neuritis, palindromic rheumatism, PANDAS, paraneoplastic cerebellar degeneration, paroxysmal nocturnal hemoglobunuria, Parry-Romberg syndrome, Pars planitis, Parsonage-Turner syndrome, pemphigus, peripheral neuropathy, perivenous encephalomyelitis, pernicious anemia, POEMS syndrome, polyarteritis nodosa, polyglandular syndromes types I, II, and III, polymyalgia rhematica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia, pyoderma gangrenosum, Raynaud's phenomenon, reactive arthritis, reflex sympathetic dystrophy, relapsing polychondritis, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), Susac's syndrome, sympathetic ophthalmia, Takayasu's arteritis, temporal arteritis, thrombocytopenic purpura (TTP), Tolosa-Hunt syndrome, transverse myelitis, type 1 diabetes, ulcerative colitis, undifferentiated connective tissue disease, uveitis, vasculitis, vitiligo and Wegener's granulomatosis (or granulomatosis with polyangiitis).

Disorders Associated with Transplantation

In some embodiments, the disorder is associated with transplantation. In some embodiments the disorder associated with transplantation is transplant rejection. In some embodiments the disorder associated with transplantation is graft-versus-host disease.

Proliferative Disorders

In some embodiments, the disorder is a proliferative disorder. In some embodiments, the proliferative disorder is a cancer.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. An "adenocarcinoma" refers to a carcinoma derived from glandular tissue or in which the tumor cells form recognizable glandular structures. The term "sarcoma" is art recognized and refers to malignant tumors of mesenchymal derivation.

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

In some embodiments the proliferative disorder is a hematological cancers. In some embodiments the proliferative disorder is a leukemia. In some embodiments, the leukemia is a T-cell leukemia.

Neurological Disorders

In some embodiments, the disorder is a neurological disorder. In some embodiments, the neurological disorder is Balo's disease, chronic inflammatory demyelinating polyneuropathy, Devic's neuromyelitis optica, Marburg acute multiple sclerosis, multiple sclerosis, Schilder's disease, or perivenous encephalomyelitis.

Combinations

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. As used herein, additional therapeutic agents that are normally administered to treat a particular disease, or condition, are known as "appropriate for the disease, or condition, being treated."

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating a TCR-Nck mediated disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmicort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevirapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmicort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behget's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behçet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T-cell activation, a cardiovascular disorder, and a CNS disorder.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation.

A compound of the current invention may also be used to advantage in combination with antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; antiandrogens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™ Fulvestrant can be administered under the trade name Faslodex™.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g., under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g., under the trademark Carboplat™. Oxaliplatin can be administered, e.g., in the form as it is marketed, e.g., under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axi receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44;

Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C$_2$α, PI3K-C$_2$β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g., unrelated to protein or lipid kinase inhibition e.g., thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, "Principles of Radiation Therapy", Cancer, in Principles and Practice of Oncology", Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXAMPLES

Figure 1:
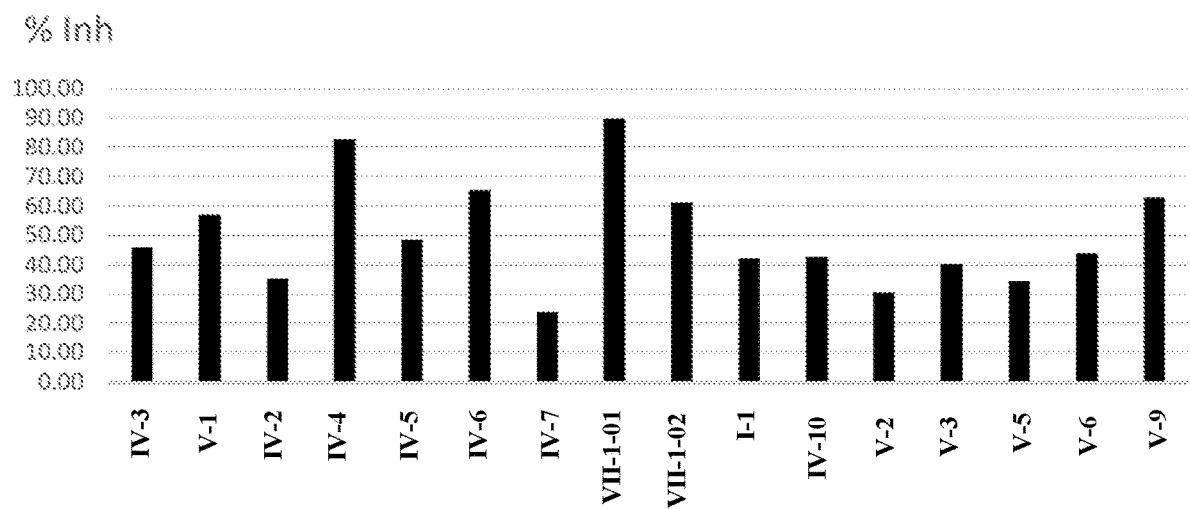
FIG. 1 shows the percentage T cell inhibition (% Inh) of compounds IV-3, V-1, IV-2, IV-4, IV-5, IV-6, IV-7, VII-1-01, VII-1-02, I-1, IV-10, V-2, V-3, V-5, V-6 and V-9, at a concentration of 0.1 nm.

Example 1. Synthesis of the Compounds of the Invention

General: The starting reagents, solvents and products were acquired from commercial sources. The term "concentration" refers to vacuum evaporation using a Büchi rotary evaporator. When specified, the reaction products were purified by means of silica gel flash chromatography (40-63 microns) using the specified solvent system. The spectroscopic data were measured using a Varian Mercury 400 spectrometer. The melting points were measured using a Büchi 535 instrument. The HPLC-MS was performed using a Gilson instrument equipped with a Gilson 321 piston pump, a Gilson 864 vacuum degasser, a Gilson 189 injection module, a Gilson 1/1000 splitter, a Gilson 307 pump, a Gilson 170 detector, and a ThermoQuest Finnigan AQA detector.

Synthesis of compounds: Subseries-1, Subseries-2, Subseries-3 and Subseries-4

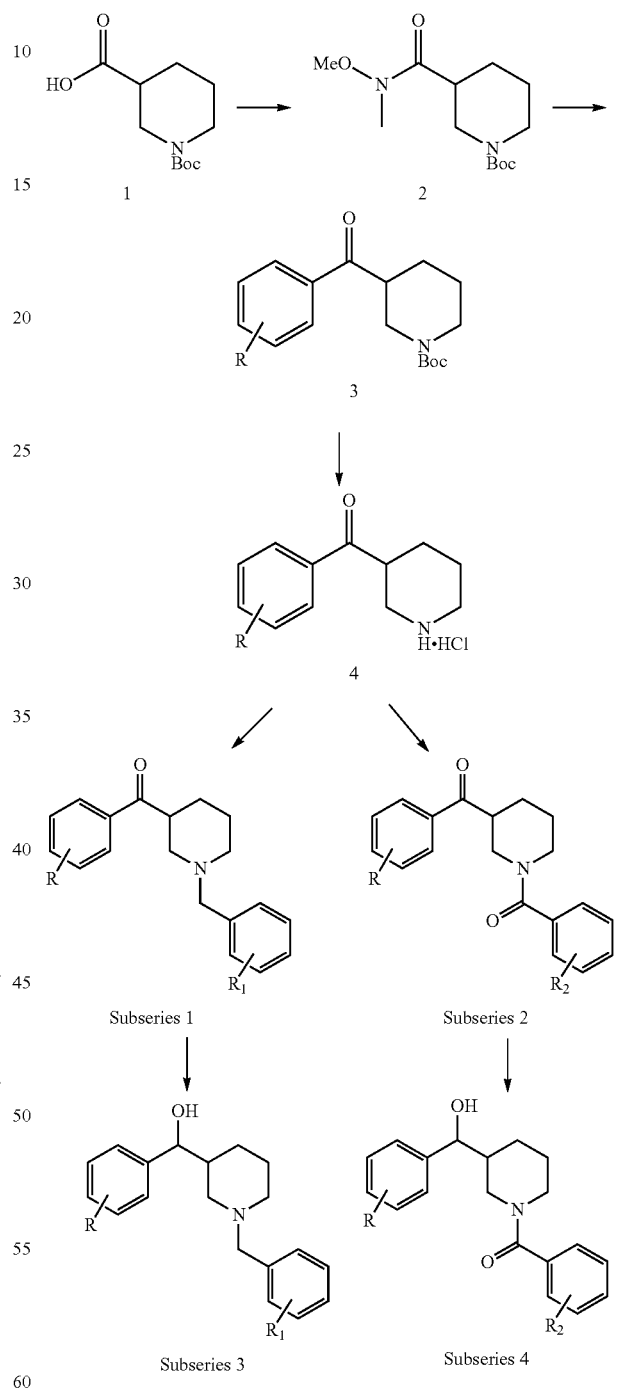

Synthesis of Compound 2: EDC.HCl (3.76 g, 0.019 mol) and HOBT (2.0 g, 0.013 mol) were added to a solution of acid 1 (3.0 g, 0.013 mol), N, O-dimethylhydroxylamine hydrochloride (1.59 g, 0.016 mol) and DIPEA (6.8 ml, 0.039 mol) in DMF (15 ml) and stirred for 12 h at room temperature (r.t.). The reaction mixture was then diluted with ice-cold water (150 ml) and extracted with EtOAC (3×50 ml). The organic extracts were combined, washed with sat. NaHCO$_3$ solution (50 ml, aqueous) followed by water (50 ml) and brine (50 ml) separated and then dried over anhydrous Na$_2$SO$_4$ and concentrated to dryness to afford amide 2 (3.0 g, crude) as a pale yellow oil.

Synthesis of Compound 3: To a cooled solution of amide 2 (3.0 g, 0.011 mol) in dry THE (20 ml) under N$_2$ at −78° C. was added 7.3 ml (0.022 mol) of 3.0 M solution of PhMgBr in THF over 30 min. Reaction temperature was gradually increased to room temperature and stirred at the same temperature for 2 h. After consumption of starting material, the reaction mixture was cooled to 0° C. and quenched by drop wise addition of sat. aq. NH$_4$Cl (30 ml). The reaction mixture was then diluted with water (100 ml); extracted with EtOAc (3×75 ml) and the organic layers were separated. The combined organic extract was washed with by water (100 ml) and brine solution (50 ml) and dried over anhydrous Na$_2$SO$_4$ and concentrated to dryness to get a crude residue which was purified (Silica gel column chromatography) using EtOAC::Hexanes to afford compound 3 (2.1 g) as a pale yellow oil.

Synthesis of Compound 4: To a cooled solution of compound 3 (2.1 g, 0.007 mol) in CH$_2$Cl$_2$(15 ml) was added 2.5 ml of 20% HCl in dioxane drop wise and stirred at room temperature for 4 h under N$_2$ atmosphere. The reaction mixture was evaporated and the residue was washed with n-Pentane (50 ml) to afford a white solid which was dried under vacuum to get compound 4 (1.35 g, 90% yield).

Synthesis of V-1: To a cooled solution of compound 4 (450 mg, 1.9 mmol) and DIPEA (0.69 ml, 3.9 mmol) in acetonitrile (10 ml) at 0° C. was added benzoyl chloride (0.23 ml, 1.9 mmol) and stirred at room temperature for 3 h. The reaction mixture was diluted with EtOAC (100 ml) and washed with sat. aq. NaHCO$_3$ solution (25 ml) followed by water (30 ml). The organic layers were combined, dried over anhydrous Na$_2$SO$_4$ and concentrated to a crude compound which was purified (prep HPLC) to afford compound V-1 (151 mg, 25% yield) as a pale yellow oil.

Remaining compounds from subseries 1 can be synthesize using above experimental procedure.

| R | R$_1$ | Compound Name |
|---|---|---|
| H | 4-Methyl | IV-1 |
| H | 4-fluoro | IV-2 |
| H | H | IV-3 |
| 2-pyridyl | H | IV-4 |
| 3-pyridyl | H | IV-5 |
| 4-pyridyl | H | IV-6 |
| 2-pyrimidyl | H | IV-7 |
| 4-pyrimidyl | H | IV-8 |
| 5-pyrimidyl | H | IV-9 |
| 4-methoxy | H | IV-10 |
| 4-Chloro | H | IV-11 |
| 4-Methyl | H | IV-12 |
| 4-Cyano | H | IV-13 |
| H | 4-methoxy | IV-14 |
| H | 4-Chloro | IV-15 |
| H | 4-Cyano | IV-16 |
| 2-methoxy | H | IV-17 |
| 2-Chloro | H | IV-18 |
| 3-methoxy | H | IV-19 |
| 3-Chloro | H | IV-20 |
| 3,4-Dimethoxy | H | IV-21 |
| 3,4-Dichloro | H | IV-22 |
| H | 2-methoxy | IV-23 |
| H | 2-Chloro | IV-24 |
| H | 3-methoxy | IV-25 |
| H | 3-Chloro | IV-26 |

-continued

| R | R$_1$ | Compound Name |
|---|---|---|
| H | 3,4-Dimethoxy | IV-27 |
| H | 3,4-Dichloro | IV-28 |
| 4-methoxy | 4-methoxy | IV-29 |
| 4-Chloro | 4-Chloro | IV-30 |
| 4-methoxy | 4-Chloro | IV-31 |
| 4-Chloro | 4-methoxy | IV-32 |
| 2-Thiazole | H | IV-33 |
| 1-Methyl-3-pyrazole | H | IV-34 |

Synthesis of Compound IV-1: To a cooled solution of compound 4 (200 mg, 0.8 mmol) and DIPEA (0.18 ml, 1.0 mmol) in acetonitrile (10 ml) at 0° C. was added 0.16 mg of 4-Methyl Benzyl bromide (0.8 mmol) and stirred at room temperature for 3 h. The reaction mixture was diluted with EtOAC (100 ml) and washed with sat. NaHCO$_3$ solution (25 ml) followed by water (30 ml). The organic layer was separated and dried over anhydrous Na$_2$SO$_4$ and concentrated to yield a crude compound which was purified (Silica gel column chromatography) using EtOAC:Hexane to afford compound IV-1 (114 mg, 43% yield) as pale yellow oil.

Remaining compounds from subseries 2 can be synthesize using above experimental procedure.

| R | R$_2$ | Compound Name |
|---|---|---|
| H | H | V-1 |
| 4-methoxy | H | V-2 |
| H | 4-methoxy | V-3 |
| 4-Chloro | H | V-4 |
| H | 4-Chloro | V-5 |
| H | 4-Methyl | V-6 |
| 4-Methyl | H | V-7 |
| 4-Cyano | H | V-8 |
| 4-Methyl | 4-Cyano | V-9 |
| H | 4-fluoro | V-10 |
| 2-methoxy | H | V-11 |
| 2-Chloro | H | V-12 |
| 3-methoxy | H | V-13 |
| 3-Chloro | H | V-14 |
| 3,4-Dimethoxy | H | V-15 |
| 3,4-Dichloro | H | V-16 |
| H | 2-methoxy | V-17 |
| H | 2-Chloro | V-18 |
| H | 3-methoxy | V-19 |
| H | 3-Chloro | V-20 |
| H | 3,4-Dimethoxy | V-21 |
| H | 3,4-Dichloro | V-22 |
| 4-methoxy | 4-methoxy | V-23 |
| 4-Chloro | 4-Chloro | V-24 |
| 4-methoxy | 4-Chloro | V-25 |
| 4-Chloro | 4-methoxy | V-26 |
| 2-pyridyl | H | V-27 |
| 3-pyridyl | H | V-28 |
| 4-pyridyl | H | V-29 |
| 2-pyrimidyl | H | V-30 |
| 4-pyrimidyl | H | V-31 |
| 5-pyrimidyl | H | V-32 |
| 2-Thiazole | H | V-33 |
| 1-Methyl-3-pyrazole | H | V-34 |

Synthesis of VI-1-01 and VI-1-02: Sodium borohydride (0.08 g, 2.15 mmol) was added to a cooled solution of compound IV-3 (400 mg, 1.4 mmol) in MeOH (20 ml) at 0-5° C., and stirred at room temperature for 2 h. After this time, the reaction mixture was concentrated and quenched with aq. NH$_4$Cl solution, extracted with EtOAC (2×100 ml) and washed with water (50 ml) followed by brine (25 ml). The organic layers were collected and dried over anhydrous Na$_2$SO$_4$ and concentrated. The crude compound VI-1 (400 mg) was purified by prep HIPLC to afford VI-1-01 (60 mg) and VI-1-02 (40 mg).

Remaining compounds from subseries 3 can be synthesize using above experimental procedure.

| R | $R_1$ | Compound Name |
|---|---|---|
| H | H | VI-1-01 and VI-1-02 |
| 3-methoxy | H | VI-2-01 and VI-2-02 |

Synthesis of VII-1-01 and VII-1-02: Sodium borohydride (0.1 g, 2.5 mmol) was added to a cooled solution of compound V-1 (300 mg, 1.0 mmol) in MeOH (20 ml) at 0-5° C., and stirred at room temperature for 2 h. After this time, the reaction mixture was concentrated and quenched with aq. $N_4Cl$ solution, extracted with EtOAC (2×100 ml) and washed with water (50 ml) followed by brine (25 ml). The organic layers were collected and dried over anhydrous $Na_2SO_4$ and concentrated. The crude compound VII-1 (250 mg) was purified by prep HPLC to afford VII-1-01 (60 mg) and VII-1-02 (60 mg).

Remaining compounds from subseries 4 can be synthesize using above experimental procedure.

Subseries-4 Compounds

| R | $R_2$ | Compound Name |
|---|---|---|
| H | H | VII-1-01 and VII-1-02 |
| 4-methoxy | H | VII-2-01 and VII-2-02 |
| 4-Chloro | H | VII-3-01 and VII-3-02 |
| H | 4-Chloro | VII-4-01 and VII-4-02 |
| 4-Methyl | H | VII-5-01 and VII-5-02 |
| 4-Cyano | H | VII-6-01 and VII-6-02 |
| 2-methoxy | H | VII-7-01 and VII-7-02 |
| 2-Chloro | H | VII-8-01 and VII-8-02 |
| 3-methoxy | H | VII-9-01 and VII-9-02 |
| 3-Chloro | H | VII-10-01 and VII-10-02 |
| 3,4-Dichloro | H | VII-11-01 and VII-11-02 |
| H | 2-Chloro | VII-12-01 and VII-12-02 |
| H | 3-Chloro | VII-13-01 and VII-13-02 |
| H | 3,4-Dichloro | VII-14-01 and VII-14-02 |
| 4-methoxy | 4-methoxy | VII-15-01 and VII-15-02 |
| 4-Chloro | 4-Chloro | VII-16-01 and VII-16-02 |
| 1-Methyl-3-pyrazole | H | VII-17-01 and VII-17-02 |

Synthetic Route for Subseries-5 (Compound I-1)

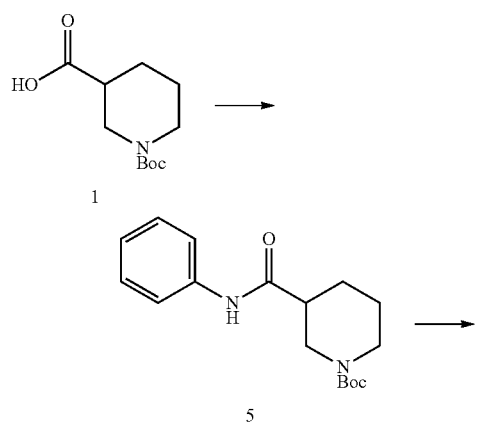

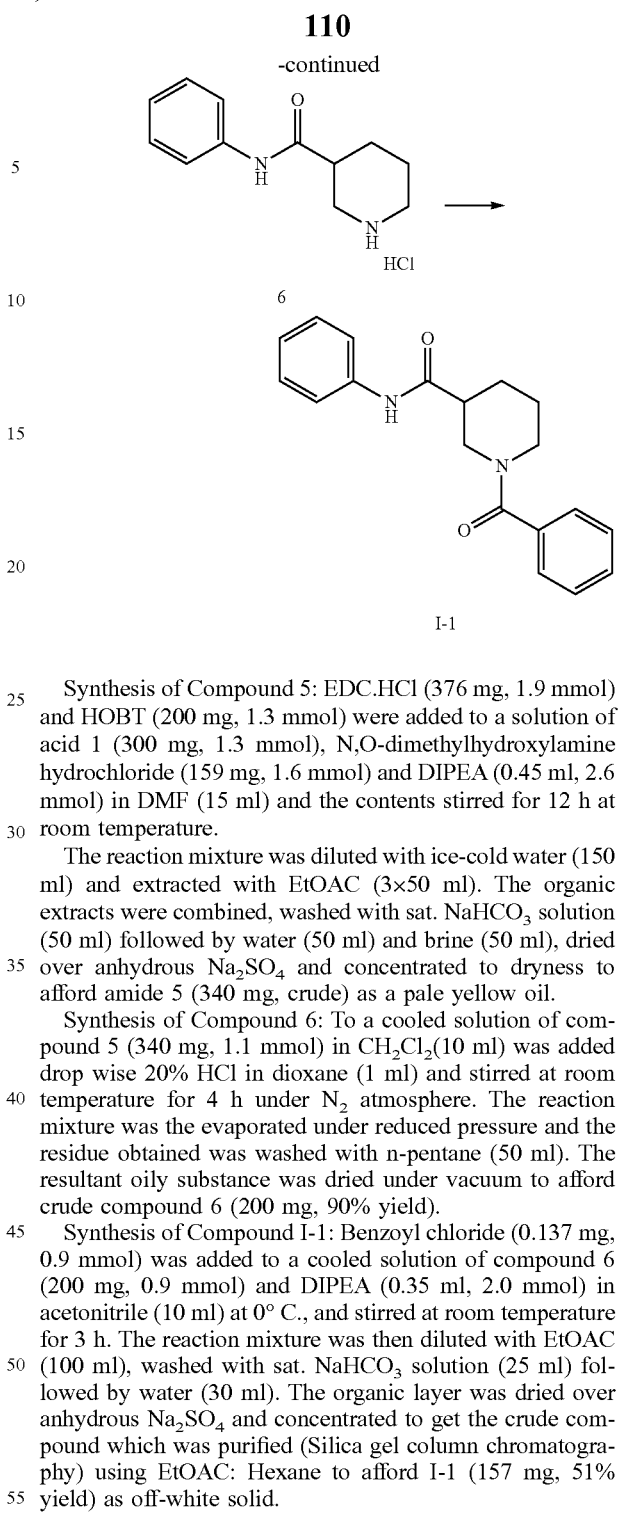

Synthesis of Compound 5: EDC.HCl (376 mg, 1.9 mmol) and HOBT (200 mg, 1.3 mmol) were added to a solution of acid 1 (300 mg, 1.3 mmol), N,O-dimethylhydroxylamine hydrochloride (159 mg, 1.6 mmol) and DIPEA (0.45 ml, 2.6 mmol) in DMF (15 ml) and the contents stirred for 12 h at room temperature.

The reaction mixture was diluted with ice-cold water (150 ml) and extracted with EtOAC (3×50 ml). The organic extracts were combined, washed with sat. $NaHCO_3$ solution (50 ml) followed by water (50 ml) and brine (50 ml), dried over anhydrous $Na_2SO_4$ and concentrated to dryness to afford amide 5 (340 mg, crude) as a pale yellow oil.

Synthesis of Compound 6: To a cooled solution of compound 5 (340 mg, 1.1 mmol) in $CH_2Cl_2$ (10 ml) was added drop wise 20% HCl in dioxane (1 ml) and stirred at room temperature for 4 h under $N_2$ atmosphere. The reaction mixture was the evaporated under reduced pressure and the residue obtained was washed with n-pentane (50 ml). The resultant oily substance was dried under vacuum to afford crude compound 6 (200 mg, 90% yield).

Synthesis of Compound I-1: Benzoyl chloride (0.137 mg, 0.9 mmol) was added to a cooled solution of compound 6 (200 mg, 0.9 mmol) and DIPEA (0.35 ml, 2.0 mmol) in acetonitrile (10 ml) at 0° C., and stirred at room temperature for 3 h. The reaction mixture was then diluted with EtOAC (100 ml), washed with sat. $NaHCO_3$ solution (25 ml) followed by water (30 ml). The organic layer was dried over anhydrous $Na_2SO_4$ and concentrated to get the crude compound which was purified (Silica gel column chromatography) using EtOAC: Hexane to afford I-1 (157 mg, 51% yield) as off-white solid.

Example 2. Activity

Figure 2:
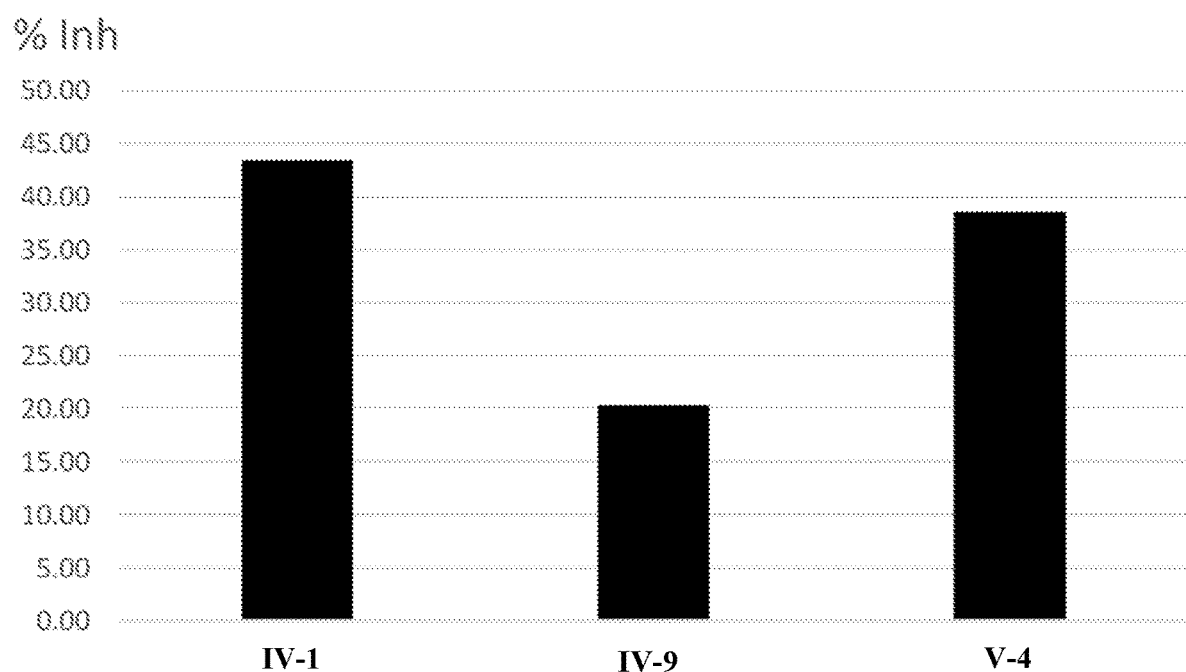
FIG. 2 shows the percentage T cell inhibition (% Inh) of compounds IV-1, IV-9 and V-4, at a concentration of 1.0 nM.

The effect of compounds IV-3, V-1, IV-1, IV-2, IV-4, IV-5, IV-6, IV-7, IV-9, VII-1-01, VII-1-02, I-1, IV-10, V-2, V-4, V-3, V-5, V-6 and V-9, on the capacity of the TCR to induce T cells proliferation was evaluated on primary T cells obtained from the blood of healthy human donors (PBMCs; peripheral blood mononuclear cells). The volunteers' PBMCs were isolated by means of density gradient centrifugation of venous blood using Ficoll-Paque Plus. The purified cells (NWT; Nylon Wood T cells) were labelled with carboxyfluorescein succinimidyl ester (CFSE) in order to analyse the cell division capacity. The labelled cells were pre-incubated for 1 hour in the absence or in the presence of the compounds at a concentration of 0.1 and 1.0 nM. Subsequently, the TCR/CD3 complex was stimulated using immobilised OKT3 (10 µg/ml) on flat-bottom P96 plates from Costar. The cells were cultured in triplicate at a density of $0.2 \times 10^5$ in 200 µl of full medium, and the proliferation was evaluated by means of flow cytometry after 5-7 days, by quantifying the fluorescence of the CFSE. As the cells divide, they dilute the amount of labelling incorporated into the daughter cells, which gives an idea of the degree of cell proliferation. The inhibitory capacity of the compounds tested at a concentration of 0.1 and 1.0 nM, is shown in FIGS. 1 and 2, respectively.

Example 3. CYP Inhibition

The effect of compounds IV-6, IV-7, and V-4 on Cytochromes P450 (CYP) inhibition was evaluated.

For each isozyme, microsomes-buffer-substrate mixture (MBS mix) is prepared by premixing appropriate volumes of buffer, microsomes and substrate. MBS mixture (179 µL) is transferred to a 96-well reaction plate. An aliquot (1 µL) is spiked from corresponding wells of Test Item stock solution plate to reaction plate. The reaction plate is pre-incubated for 5 minutes at 37° C. Reaction is initiated by the addition of 20 µL of NADPH solution. Each experiment is performed in duplicate. Reaction plate is incubated for predetermined time at 37° C. and quenched using either 200 µL of acetonitrile (for CYP2C9, CYP2D6, CYP2C19 and CYP3A4) or 200 µL of a mixture of 70:30 1% formic acid:acetonitrile (for CYP1A2). The protein concentration, incubation time, substrate concentrations and metabolite monitored for each CYP is given in the table below:

| Isozyme | Experimental conditions | |
|---|---|---|
| | Protein (mg/mL) | Metabolite |
| CYP1A2 | 0.15 | Acetaminophen |
| CYP2C9 | 0.15 | 4-hydroxy diclofenac |
| CYP2C19 | 0.25 | 4'-hydroxy mephenytoin |
| CYP2D6 | 0.15 | Dextrorphan |
| CYP3A4 | 0.10 | 1-hydroxy midazolam |
| | 0.15 | 6-β-hydroxy testosterone |

Certain CYP inhibition data is shown in Table 5, below. Class A: IC50≤5 uM; Class B: 5 uM<IC50≤20 uM; Class C: 20 uM<IC50≤50 uM; Class D: IC50 >50 uM.

TABLE 5

CYP Inhibition

| Compound # | CYP IC50 uM | | | | | |
|---|---|---|---|---|---|---|
| | CYP1A2 | CYP2C9 | CYP2C19 | CYP2D6 | CYP3A4[a] | CYP3A4[b] |
| IV-6 | C | B | A | A | A | B |
| IV-7 | D | D | D | B | D | D |
| V-4 | A | B | A | A | D | C |

Example 4. Microsomal Stability

The microsomal stability of compounds IV-6, IV-7, and V-4 was evaluated.

Intrinsic clearance studies are performed individually with mouse, rat and human liver microsomes at 0.5 mg/mL protein concentration. Briefly, for protein concentration 0.5 mg/mL assay, liver microsomal protein (12.5 uL), NAPDH (50 uL) and phosphate buffer (435 uL) are co-incubated (pre-incubation) in a 96-well deep well plate in an orbital incubator (10 min, 37° C.). Reactions are initiated by the addition of 2.5 uL of test item working stock solution (100 uM). Aliquots (50 uL) are withdrawn from the reaction tube at 0, 5, 10, 20 and 30 minutes and the reaction is immediately terminated by transferring to a 96 deep well plate containing 50 uL of acetonitrile. Verapamil is used as a positive control in mouse, rat and human liver microsomes. To the quenched samples internal standard is added and vortex mixed followed by centrifugation at 4000 rpm for 10 minutes and an aliquot of supernatant is taken for LC-MS/MS analysis. Samples are analyzed by a suitable fit-for-purpose multiple reaction monitoring method developed on LC-MS/MS using and API 4000 mass spectrometer to estimate the area ratio (analyte peak area/internal standard peak area).

Certain microsomal stability data is shown in Table 6, below. Class A: T1/2≥30 minutes; Class B: 10 minutes ≤T1/2<30 minutes; Class C: T1/2<10 minutes.

TABLE 6

| | Microsomal Stability | | |
|---|---|---|---|
| | Microsomal stability (T1/2 min) | | |
| Compound # | Mouse | Rat | Human |
| IV-6 | C | C | B |
| IV-7 | A | B | A |
| V-4 | C | C | B |

Example 5. hERG Inhibition

The effect of compounds IV-6, IV-7, and V-4 on hERG inhibition was evaluated.

HEK cells stably transfected with the hERG clone are maintained at 37±2° C. in a 5% CO2 incubator. The cells are initially revived and grown in DMEM/F12+GlutaMAX-I medium supplemented with 9% fetal bovine serum (FBS) and antibiotics (Penicillin 100 IU/mL Streptomycin 100 µg/mL) (complete medium). Furthermore, the cells are continuously maintained and passaged in complete media in addition to the appropriate concentration of selection antibiotic (Geneticin (G418) 200 µg/mL) (Selection media). The cells are sub cultured every 2-3 days and medium is changed with complete medium at least a day before the experiment.

The cells are harvested on the day of experiment, dislodged and suspended in sterile filtered external solution (NaCl 140 mM, KCl 4 mM, MgCl2 1 mM, CaCl2 2 mM, D-Glucose monohydrate 5 mM, Hepes/NaOH 10 mM, pH 7.4, Osmolarity:298+/−5 mOsmol).

The NPC®-1 chip of the Port-a-Patch® is filled with 5 µL of internal solution (KCl 50 mM, NaCl 10 mM, KF1 60 mM, EGTA 20 mM, Hepes/KOH 10 mM, pH 7.2, Osmolarity: 285+/−5 mOsmol) and it is screwed onto the chip holder. The Faraday cage is then fixed on the chip holder, such that the external electrode is placed near to the chip aperture. 5 µL of external solution is added to the center of the aperture so that the external electrode is also in contact with the solution.

The experiment is be initiated. Once the set threshold of resistance attained (i.e., 2-3.5 MOhm), 5 µL of cell suspension is added in the middle of the external solution droplet after the Suction Control unit has generated the suction pulse. The suction automatically attracts a cell to the aperture, resulting in an increase in the chip resistance. When the cell is captured and the set threshold for the resistance is reached, the software recognizes this increase in resistance and proceeds to the next step of the sealing procedure. 20 µL of seal enhancer solution (NaCl 80 mM, KCl 4 mM, MgCl2 10 mM, CaCl$_2$) 35 mM, Hepes (Na+salt)/HCl pH 7.4, Osmolarity: 298+/−5 mOsmol) is added 2-3 times. When the threshold resistance is reached, Patch Control automatically moves to the step of improving the seal. When the desirable resistance (Rpip) is reached, whole cell mode is attained and maintained.

Finally, hERG protocol is selected to run the experiment. The seal enhancer solution is replaced with 20 µL external solution after 2-4 rinses and then the test item is added (from lower to higher concentration) and checked for current inhibition. All the experiments are performed at ambient temperature (22-25° C.).

Figure 3:
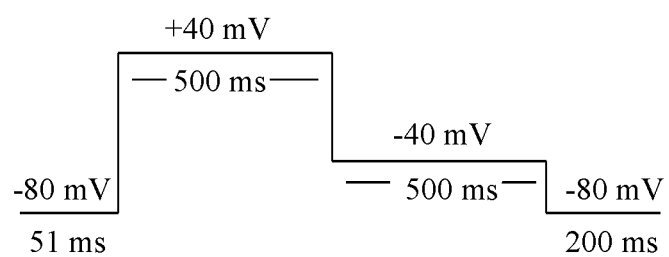
FIG. 3 shows a schematic diagram of the Pulse protocol.

A schematic diagram (FIG. 3) of the Pulse protocol: Cells are stimulated every 10 seconds using the following protocol. The holding potential, sweep intervals and the depolarization/repolarization potentials are furnished in the table below.

| Protocol | Voltage (mili-volts) | Duration (mili-seconds) |
|---|---|---|
| Holding potential | −80 | 51 |
| Depolarization | +40 | 500 |
| Repolarization | −40 | 500 |
| Holding potential | −80 | 200 |

Once the stable current is attained (at least 2-5 minutes) vehicle control is added and the current measured till the stable current is achieved. 3-5 consecutive data points from the last stable current phase are considered for further analysis. The test concentrations are analyzed from the lower to the higher concentrations (1, 3, 10 and 30 µM) in duplicates till stable current is achieved along with positive control. The system performs on-line analysis for several parameters which include functions that acquire data from traces and functions that perform calculations on the results of other functions.

Certain hERG inhibition data is shown in Table 7, below.

TABLE 7 hERG Inhibition

| Compound # | Concentration (µM) | Percent Inhibition Trial I | Trial II | Mean (%) |
|---|---|---|---|---|
| Effect of IV-6 on IKr current | | | | |
| IV-6 | 1 | 0.00 | 4.74 | 2.37 |
| | 3 | 0.00 | 0.00 | 0.00 |
| | 10 | 7.16 | 13.14 | 10.15 |
| | 30 | 39.88 | 31.05 | 35.47 |
| Propafenone | 10 | 80.53 | N/A | 80.53 |
| IC50 = 44.57 µM | | | | |
| Effect of IV-7 on IKr current | | | | |
| IV-7 | 1 | 0.00 | 0.00 | 0.00 |
| | 3 | 1.46 | 0.00 | 0.73 |
| | 10 | 3.44 | 0.54 | 1.99 |
| | 30 | 17.25 | 25.87 | 21.56 |
| Propafenone | 10 | 70.20 | 70.83 | 70.52 |
| IC 50 = 73.23 µM | | | | |
| Effect of V-4 on IKr current | | | | |
| V-4 | 1 | 16.19 | 10.20 | 13.20 |
| | 3 | 20.54 | 17.01 | 18.78 |
| | 10 | 26.38 | 19.75 | 23.07 |
| | 30 | 39.46 | 38.69 | 39.08 |
| Propafenone | 10 | 68.16 | 69.79 | 68.98 |
| IC 50 = 76.03 µM | | | | |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example

The invention claimed is:

1. A compound selected from:

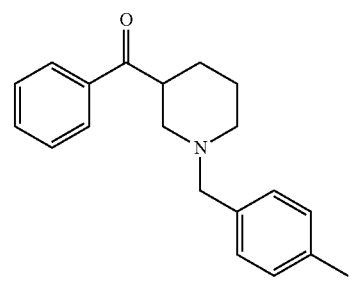

IV-1

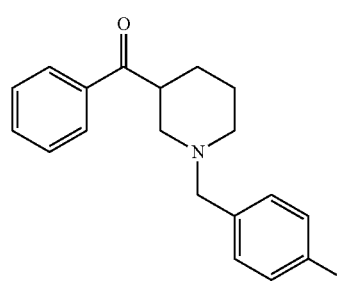

IV-2

IV-4
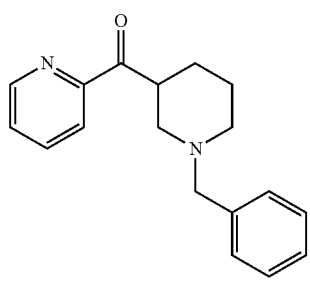
IV-5
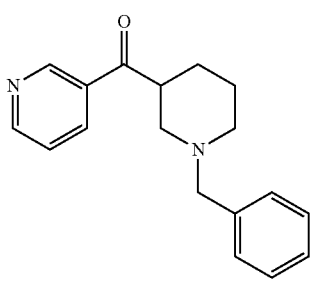
IV-6
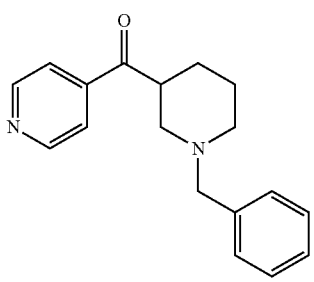
IV-7
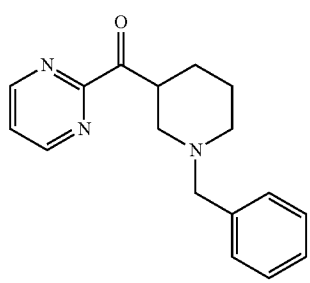
IV-8
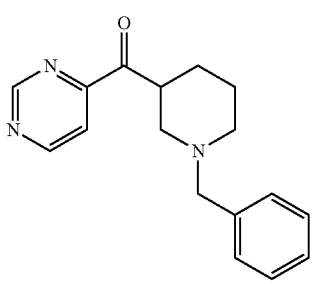
IV-9
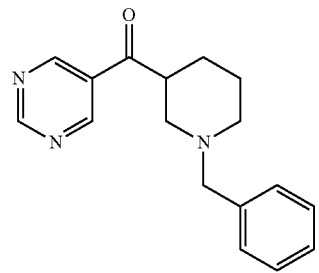
IV-10
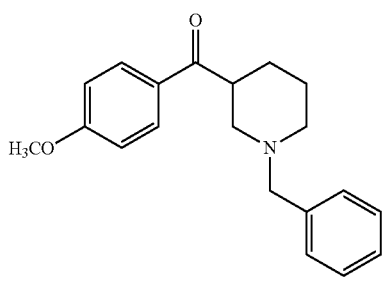
IV-12
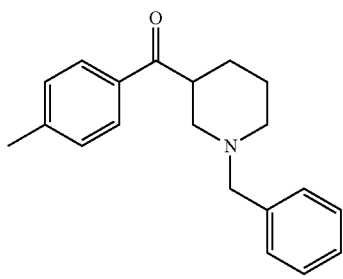
IV-13
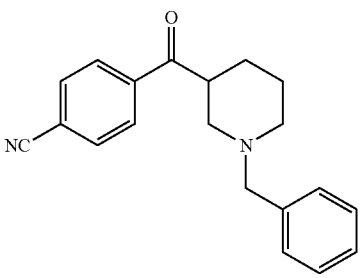
IV-15
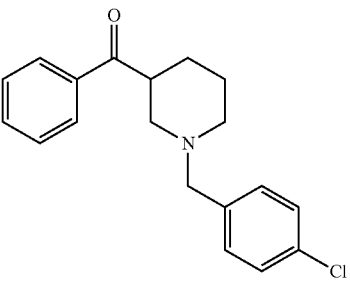

-continued
IV-16
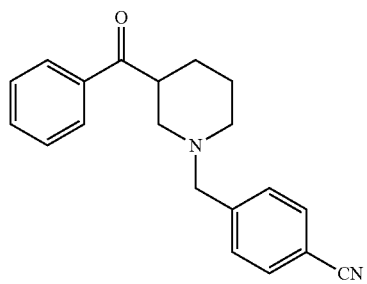
IV-17
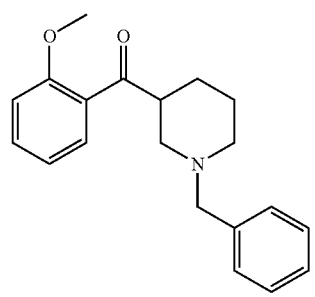
IV-18
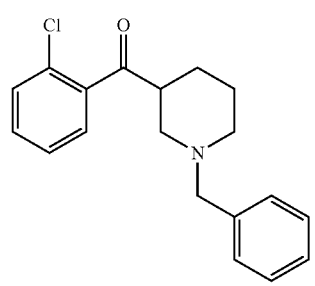
IV-19
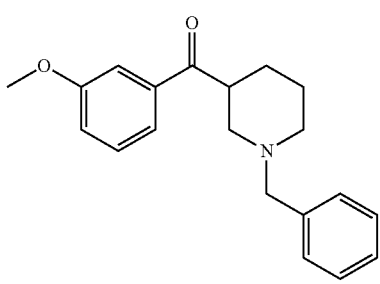
IV-20
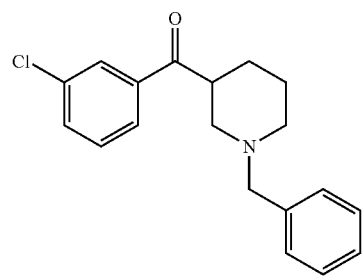
-continued
IV-21
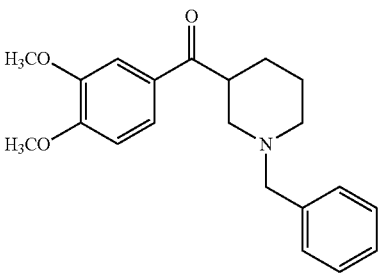
IV-22
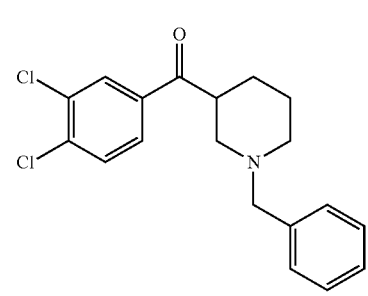
IV-23
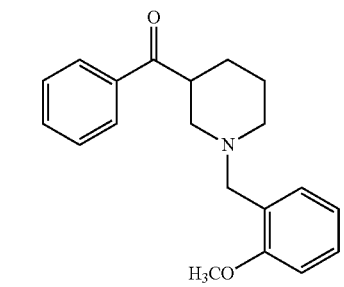
IV-24
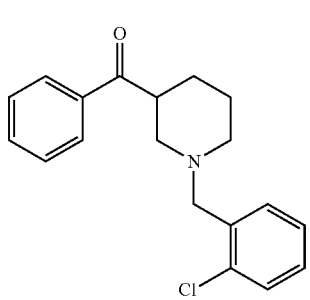
IV-25
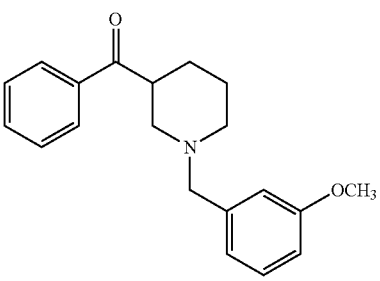

IV-26
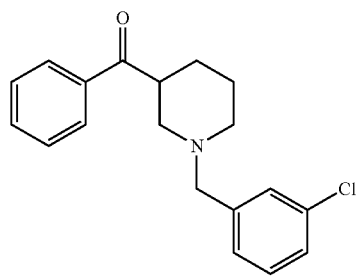
IV-27
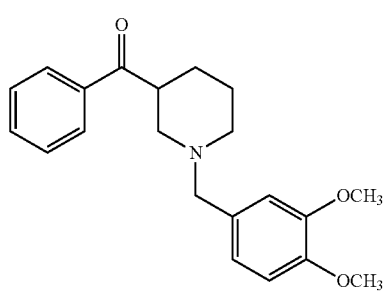
IV-28
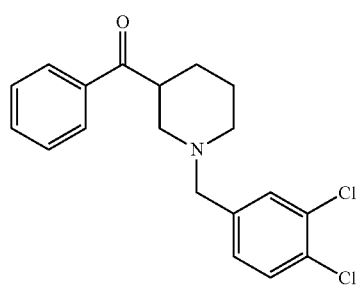
IV-29
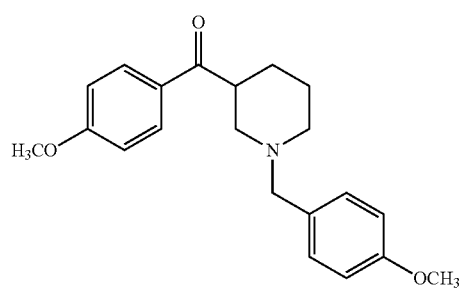
IV-30
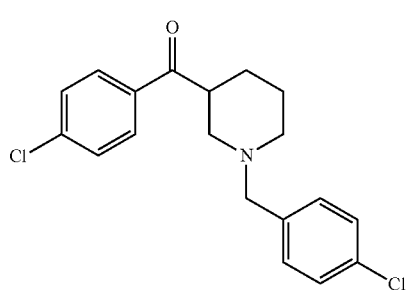
IV-31
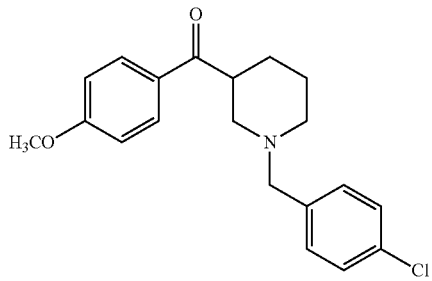
IV-33
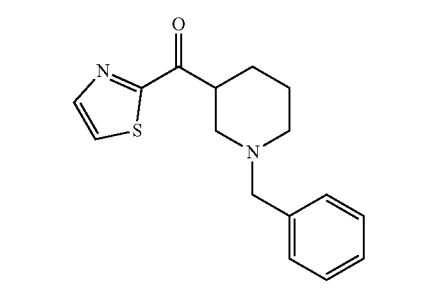
IV-34
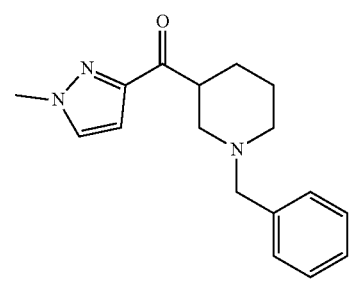
V-7
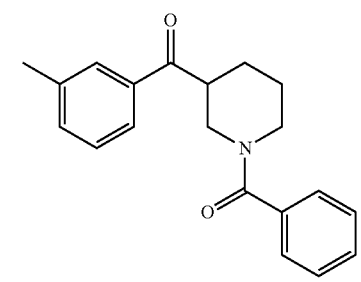
V-8
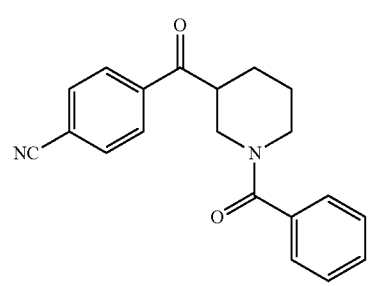

-continued
V-9
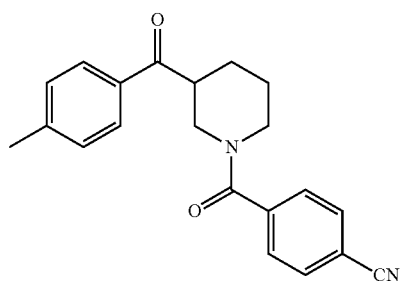
V-11
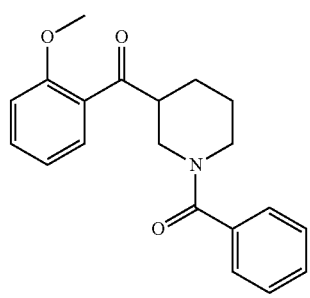
V-12
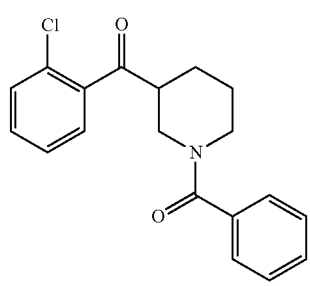
V-13
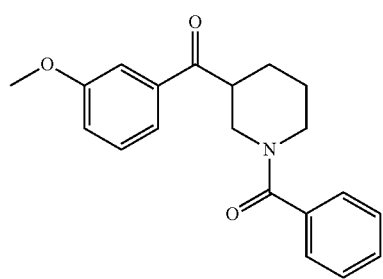
V-15
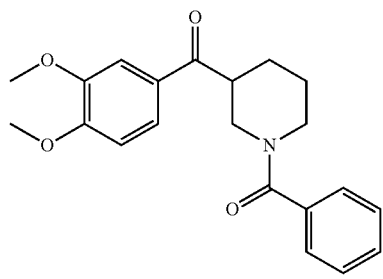
-continued
V-16
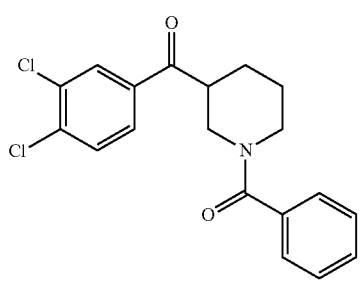
V-26
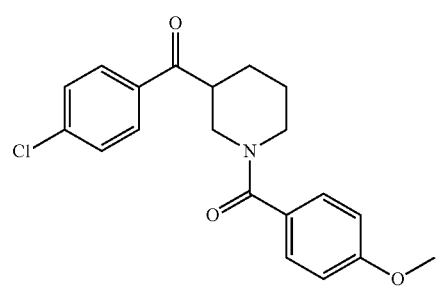
V-27
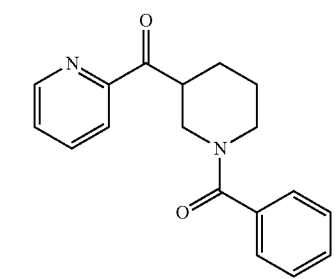
V-28
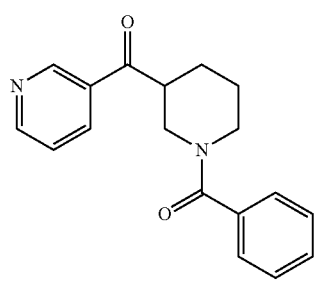
V-29
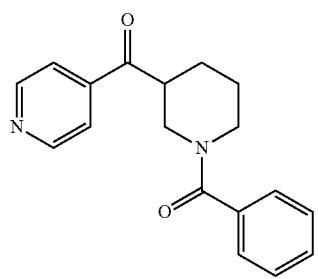

-continued
V-30
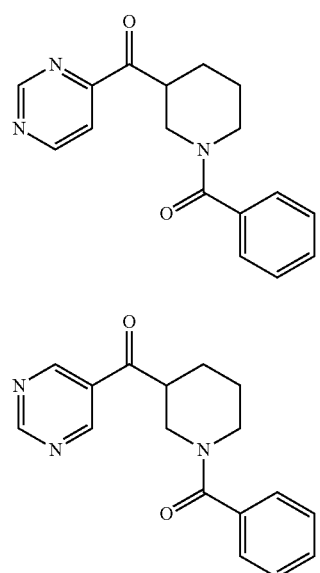
V-31
V-32
V-33
V-34
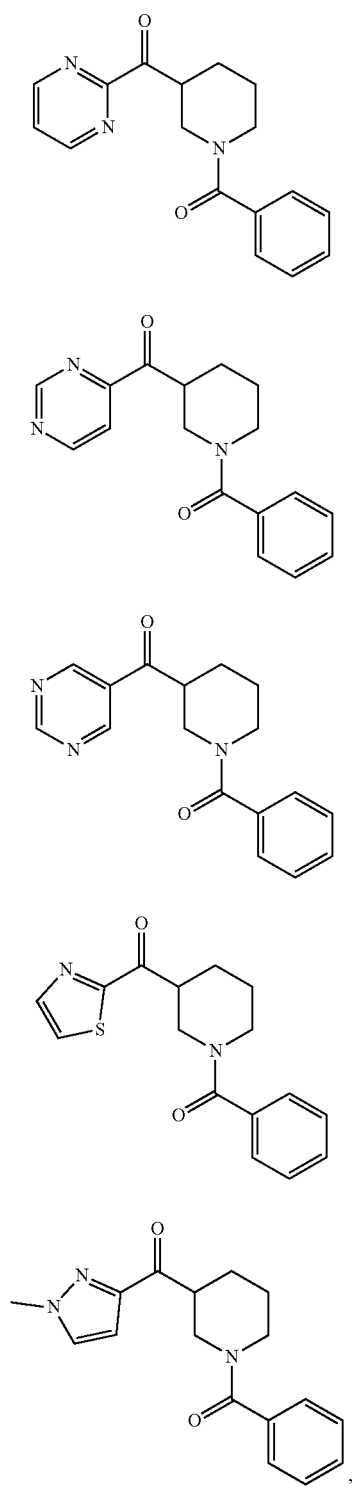
or a pharmaceutically acceptable salt thereof.
2. A pharmaceutical composition comprising the compound of claim 1, or the compound of formula:
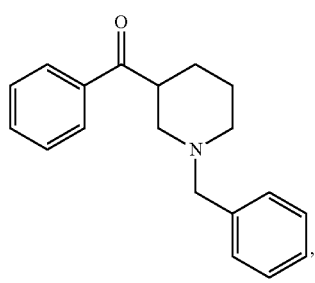
(IV-3)
or a compound selected from:
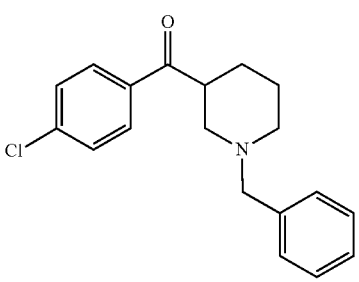
IV-11
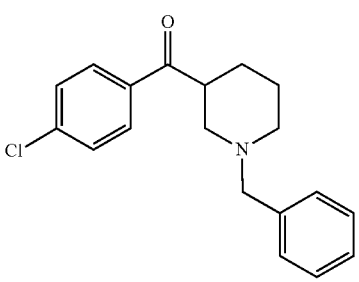
IV-32
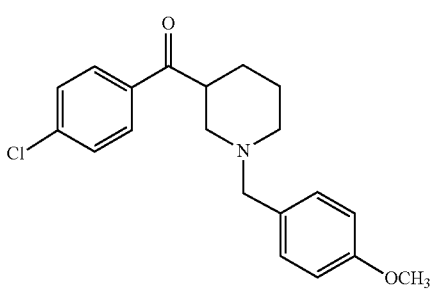
V-2
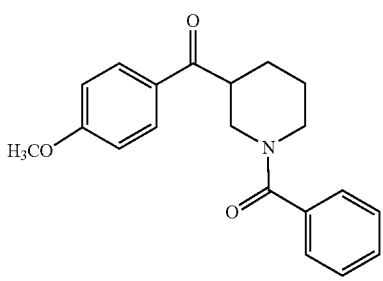
V-3
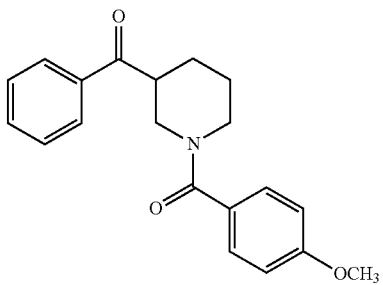

V-4
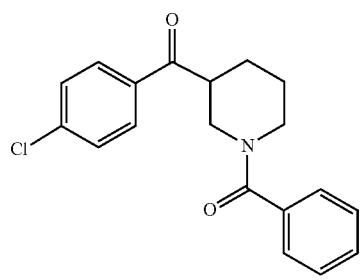
V-5
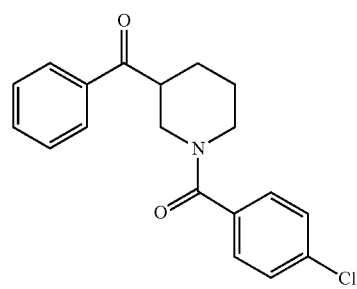
V-6
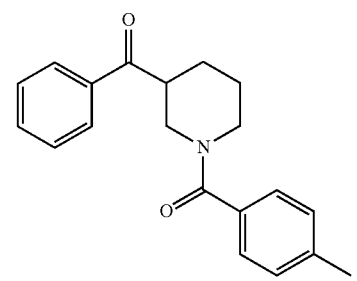
V-10
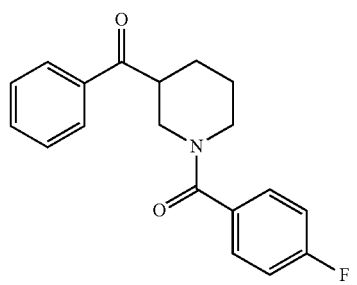
V-14
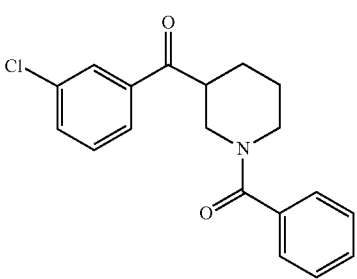
V-17
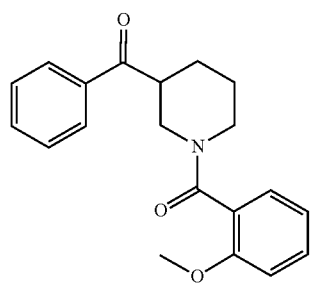
V-18
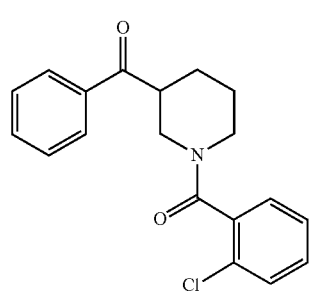
V-19
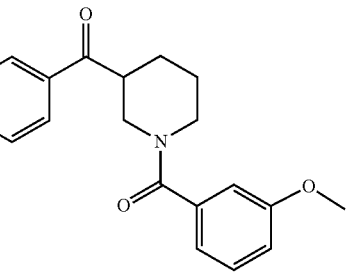
V-20
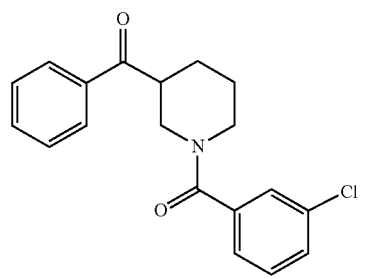
V-21
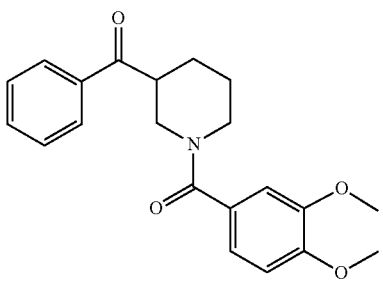

-continued
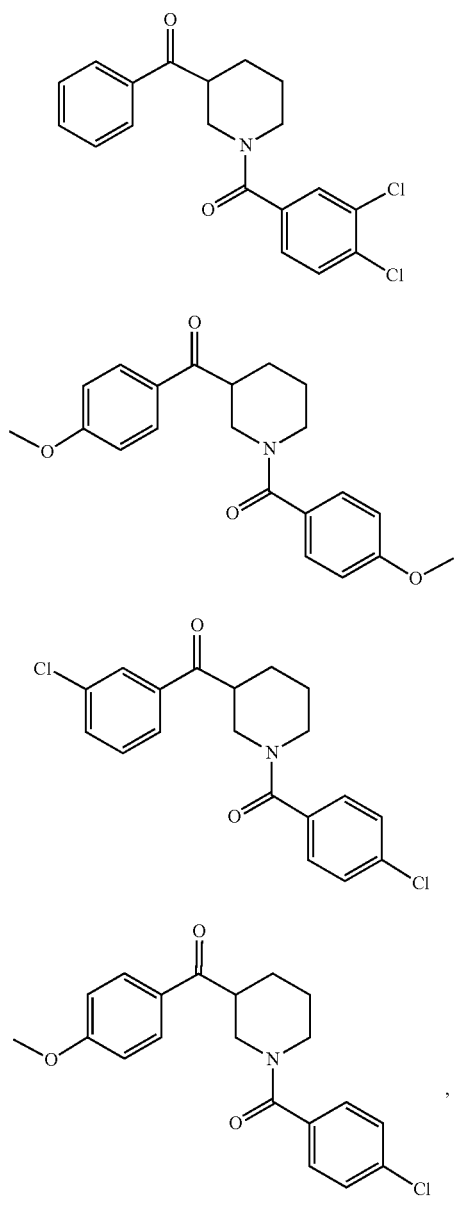
or a pharmaceutically acceptable salt thereof, and a pharmaceutically acceptable carrier, adjuvant, or vehicle.
3. The compound of claim 1, wherein the compound is selected from:
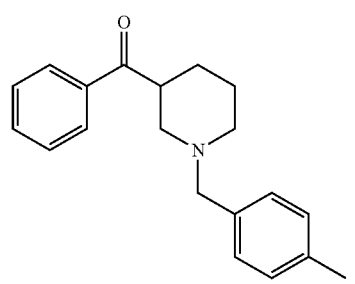
-continued
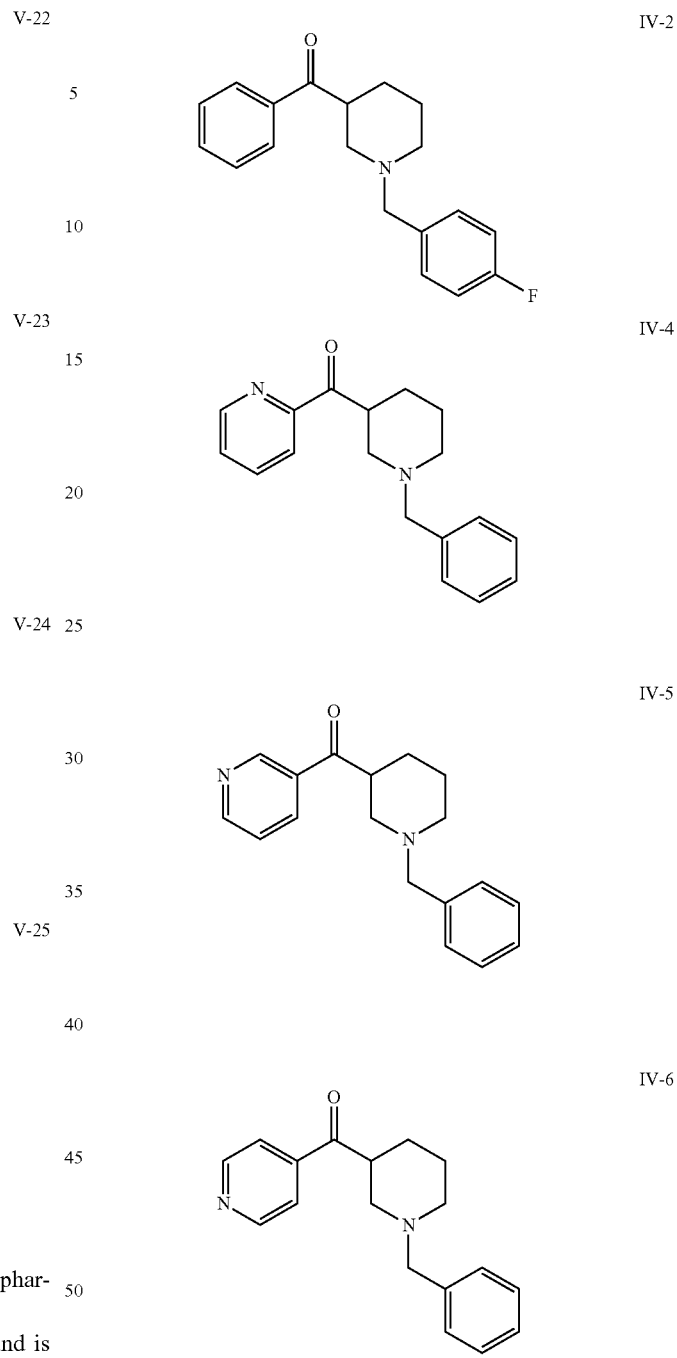

IV-8
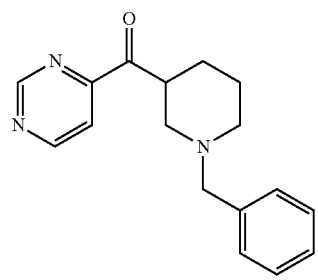
IV-9
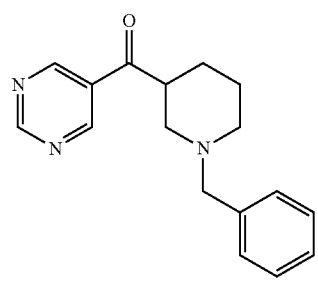
IV-10
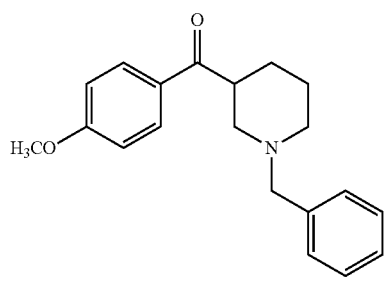
IV-12
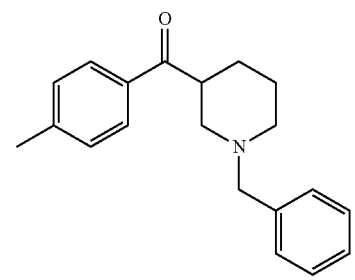
IV-13
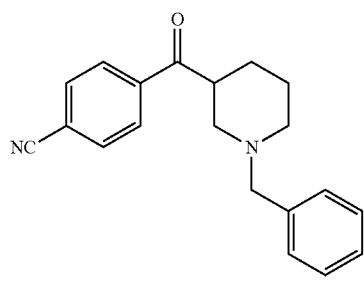
IV-15
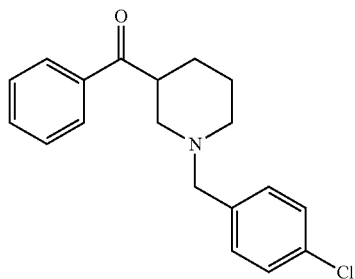
IV-16
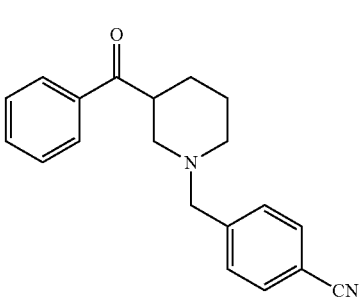
IV-17
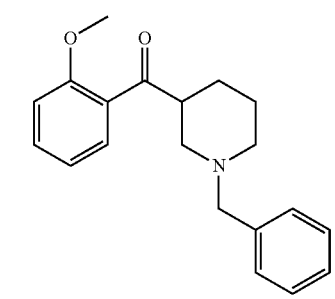
IV-18
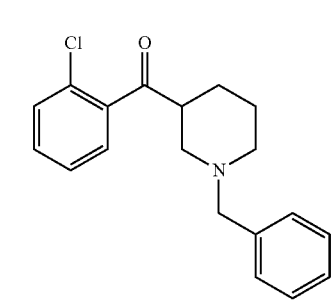
IV-19
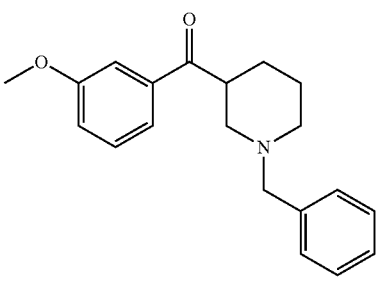

IV-20
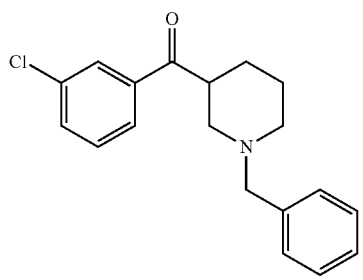
IV-21
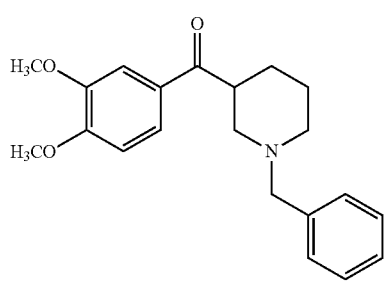
IV-22
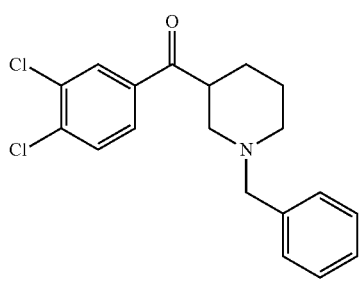
IV-23
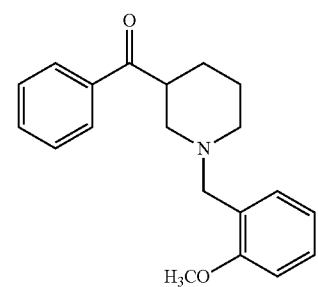
IV-24
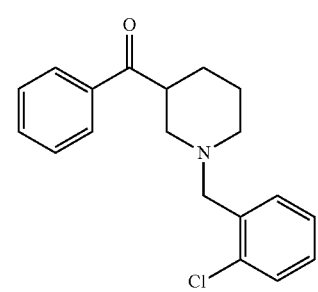
IV-25
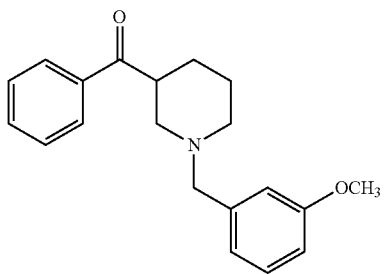
IV-26
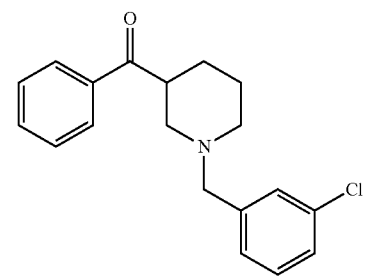
IV-27
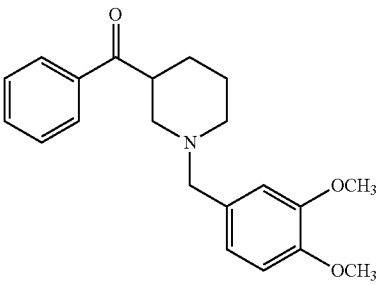
IV-28
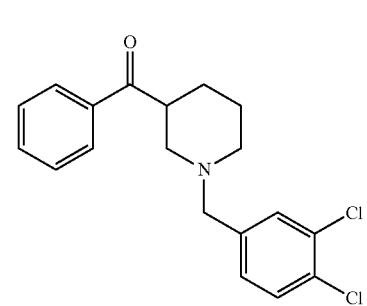
IV-29
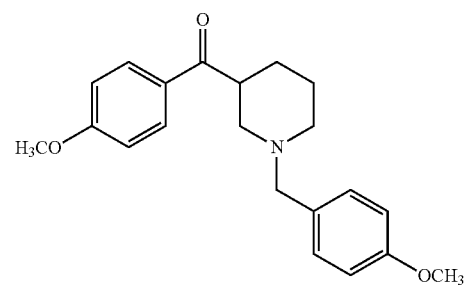

133
-continued
IV-30
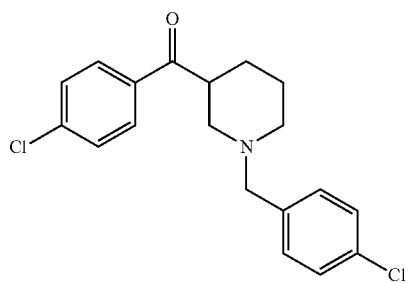
IV-31
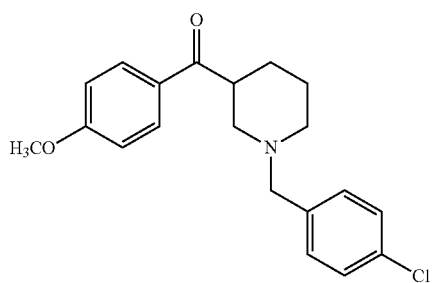
IV-33
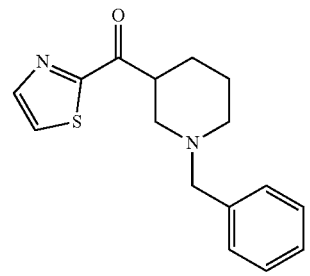
IV-34
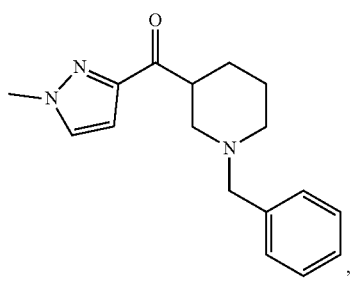
,
or a pharmaceutically acceptable salt thereof.
4. The compound of claim 1, wherein the compound is selected from:
IV-1
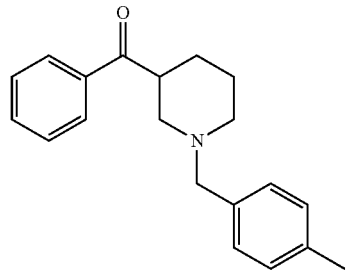
134
-continued
IV-2
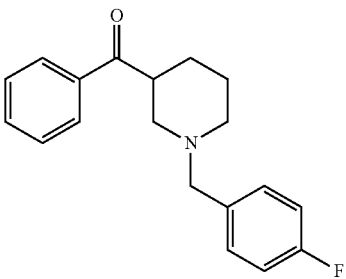
IV-3
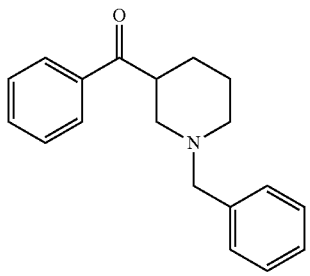
IV-4
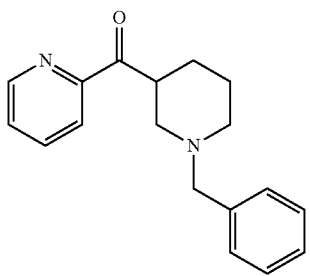
IV-5
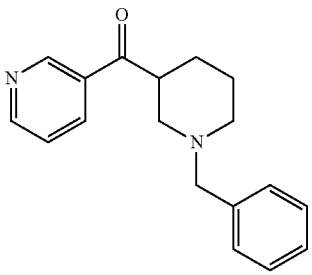
IV-6

IV-7
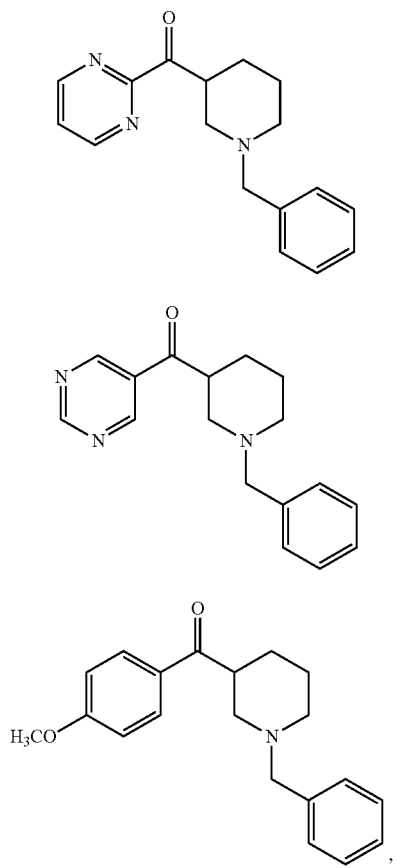
IV-9
IV-10
or a pharmaceutically acceptable salt thereof.
5. The compound of claim 1, wherein the compound is selected
V-7
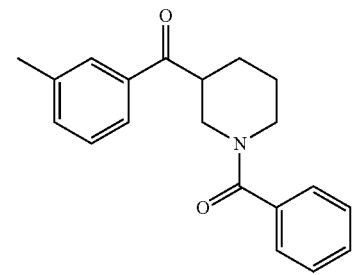
V-8
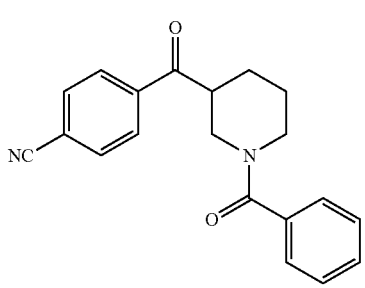
V-9
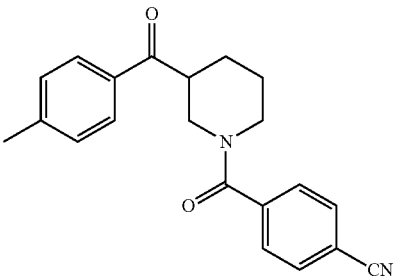
V-11
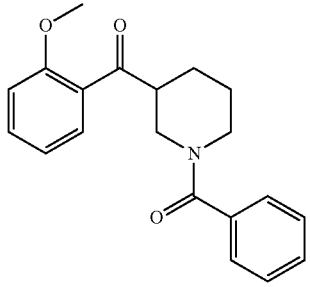
V-12
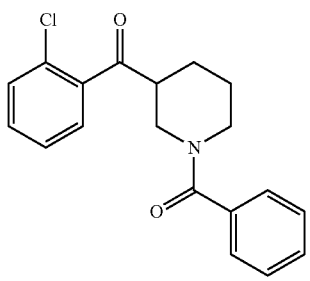
V-13
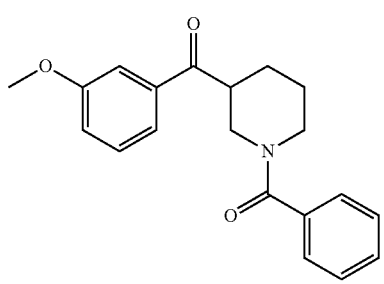
V-15
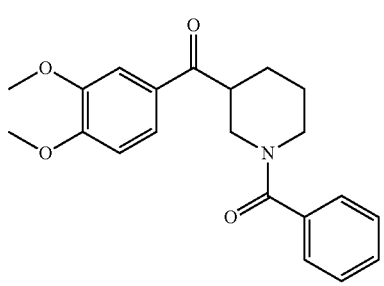

V-16
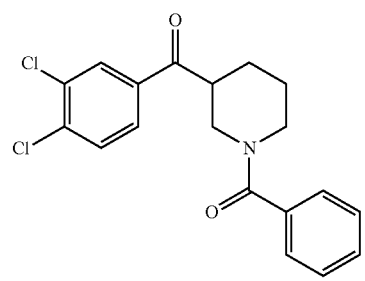
V-26
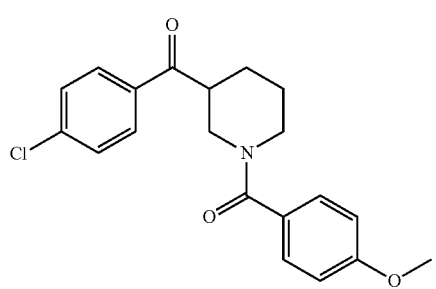
V-27
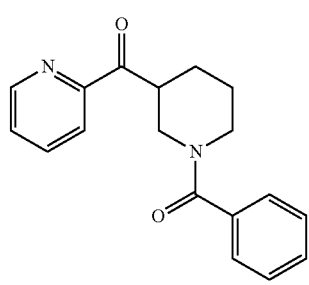
V-28
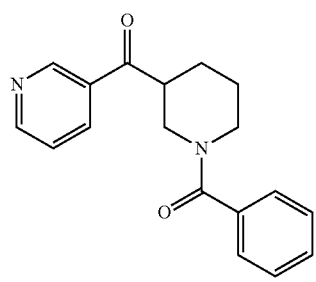
V-29
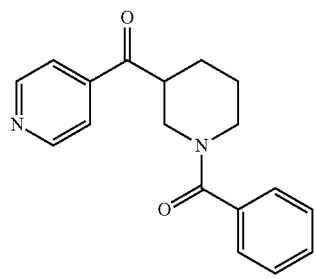
V-30
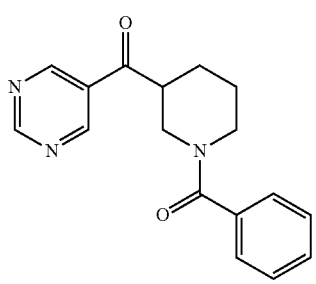
V-31
V-32
V-33
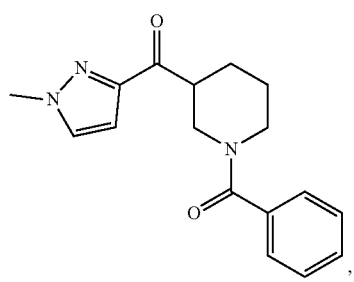
V-34
or a pharmaceutically acceptable salt thereof.

6. The compound of claim 1, wherein the compound is:
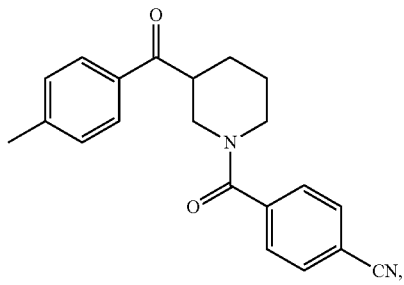
V-9
or a pharmaceutically acceptable salt thereof.
7. A compound selected from:
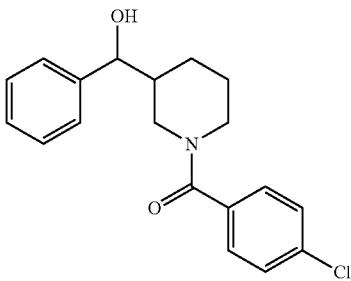
VI-2
VII-1
VII-2
VII-3
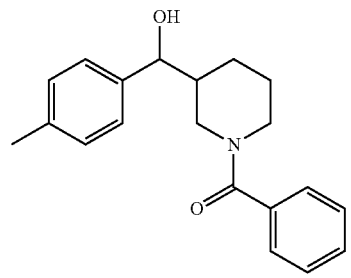
VII-4
VII-5
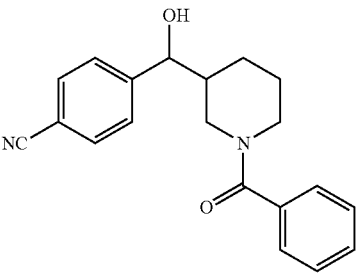
VII-6
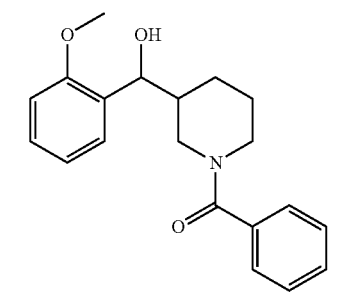
VII-7
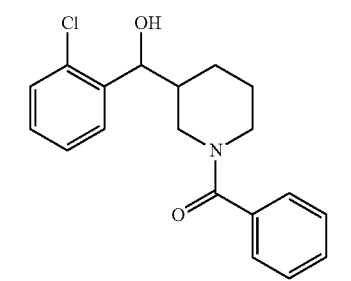
VII-8

-continued
VII-9
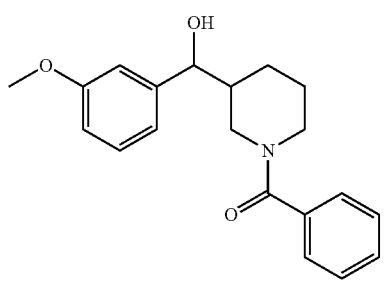
VII-10
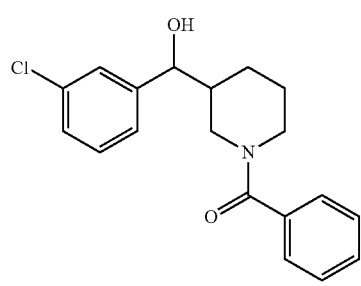
VII-11
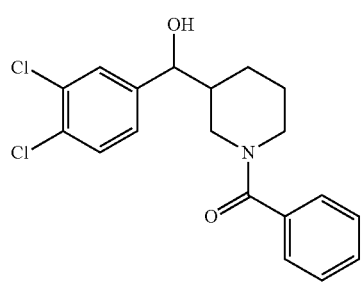
VII-12
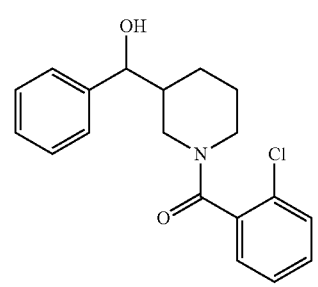
VII-13
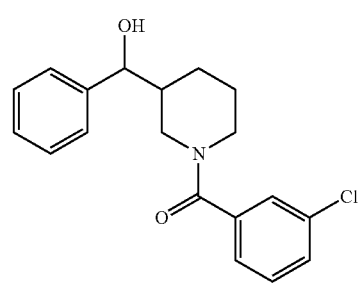
-continued
VII-14
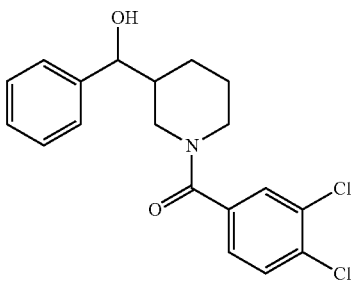
VII-15
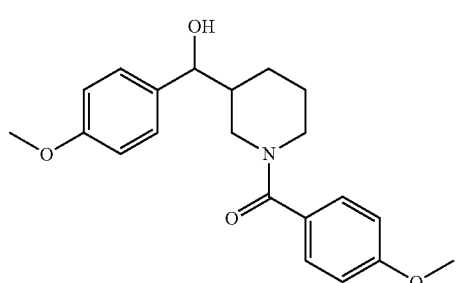
VII-16
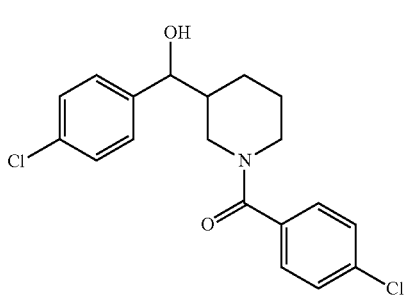
VII-17
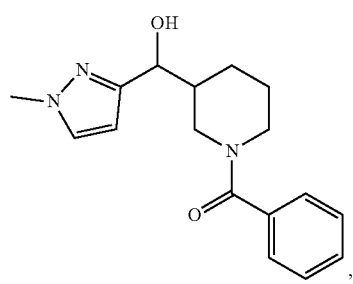
or a pharmaceutically acceptable salt thereof.
8. The compound of claim 7, wherein the compound is:
VI-2
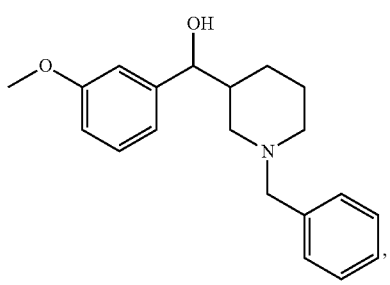
or a pharmaceutically acceptable salt thereof.
9. The compound of claim 7, wherein the compound is selected from:

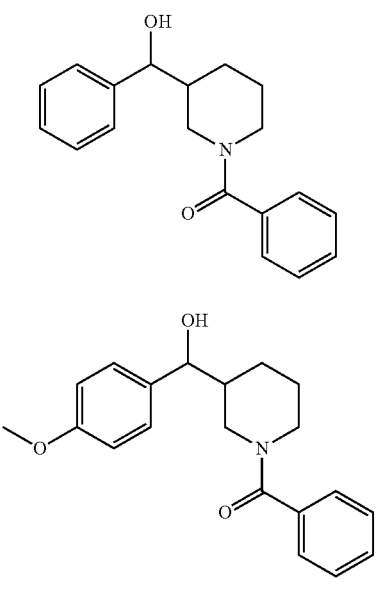
VII-1
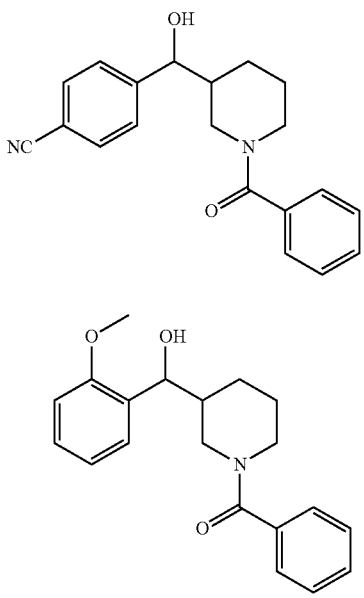
VII-6
VII-2
VII-7
VII-3
VII-8
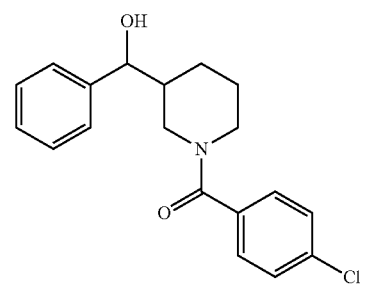
VII-4
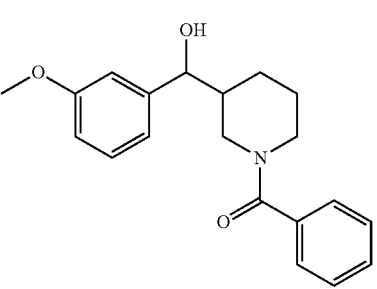
VII-9
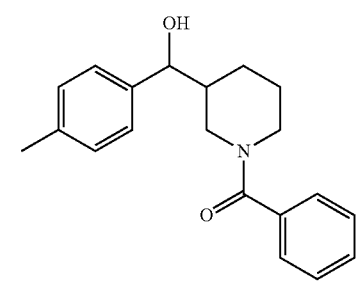
VII-5
VII-10

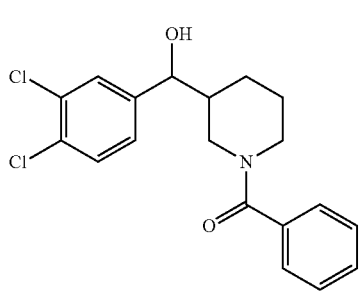
VII-11
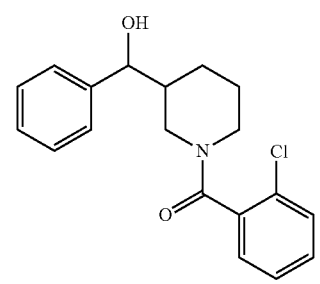
VII-12
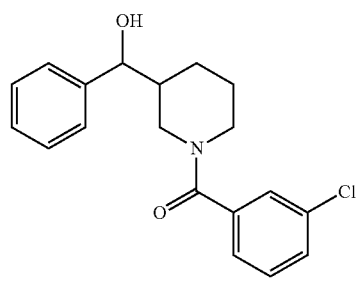
VII-13
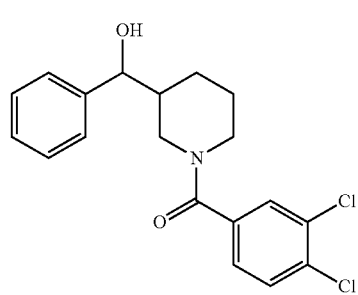
VII-14
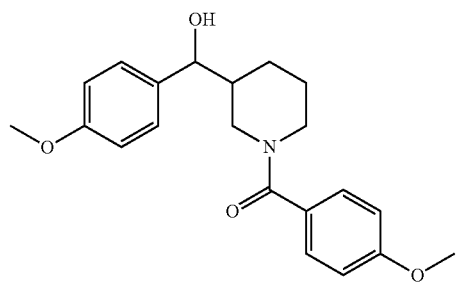
VII-15
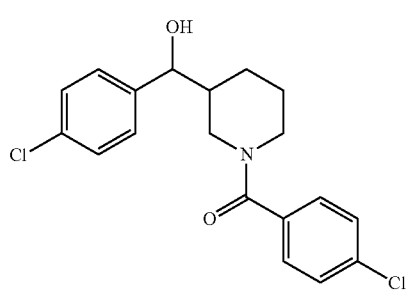
VII-16
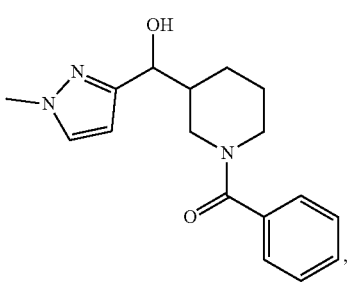
VII-17
or a pharmaceutically acceptable salt thereof.
10. The compound of claim 7, wherein the compound is selected from:
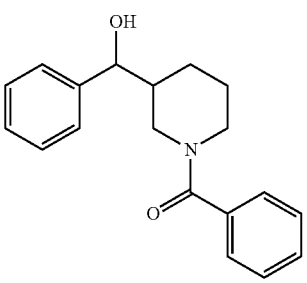
VII-1
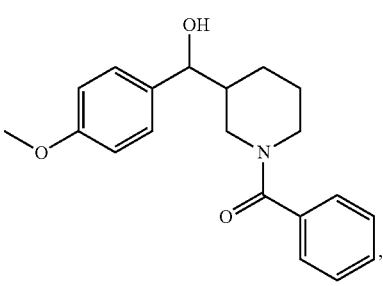
VII-2
or a pharmaceutically acceptable salt thereof.
11. A pharmaceutical composition comprising the compound of claim 7, or the compound of formula:

or a pharmaceutically acceptable salt thereof, and a pharmaceutically acceptable carrier, adjuvant, or vehicle.

12. A compound selected from:

(VI-1)

(IV-6)

(IV-7)

or a pharmaceutically acceptable salt thereof.

13. The compound of claim 12, wherein the compound is:

(IV-6)

or a pharmaceutically acceptable salt thereof.

14. The compound of claim 12, wherein the compound is:

(IV-7)

or a pharmaceutically acceptable salt thereof.

15. The pharmaceutical composition of claim 2, wherein the compound is:

(V-4)

or a pharmaceutically acceptable salt thereof.

16. A pharmaceutical composition comprising the compound of claim 12, or a pharmaceutically acceptable salt thereof, and a pharmaceutically acceptable carrier, adjuvant, or vehicle.

17. A method for treating an autoimmune disease, a lymphoma, or a T-cell leukemia in a patient, comprising administering to the patient the compound of claim 1, or the compound of formula:

(IV-3)

or a compound selected from:
IV-11
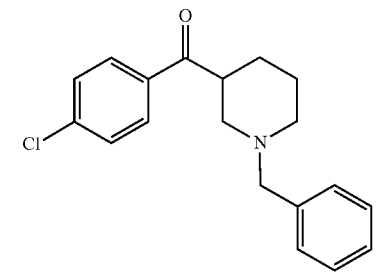
IV-32
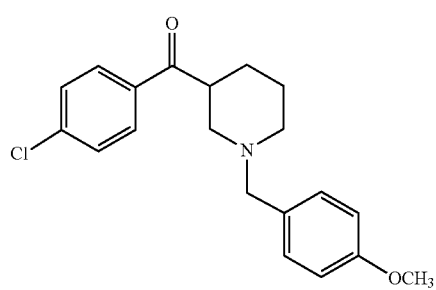
V-2
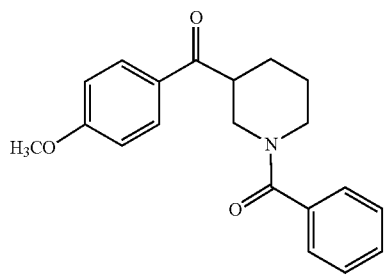
V-3
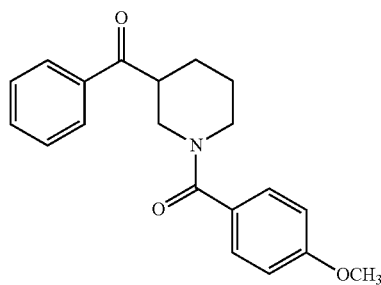
V-4
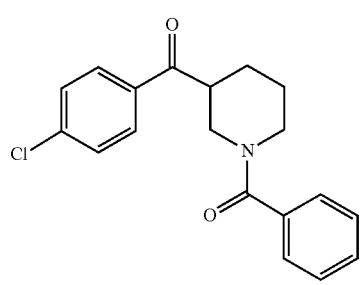
V-5
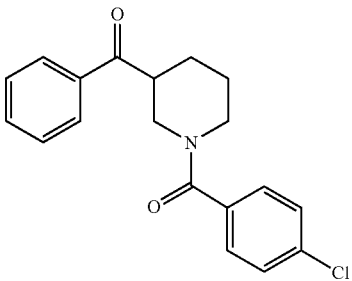
V-6
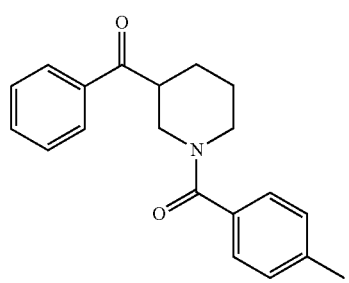
V-10
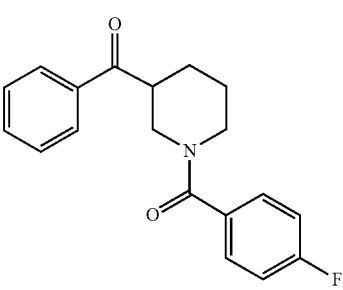
V-14
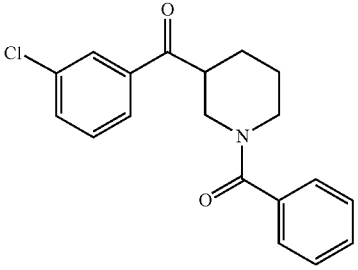
V-17
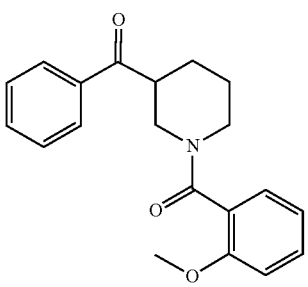

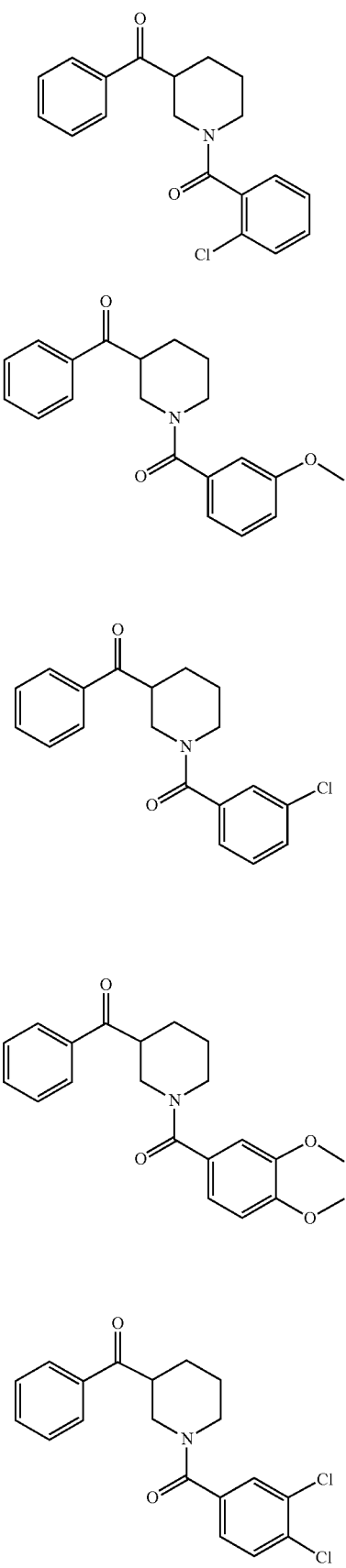

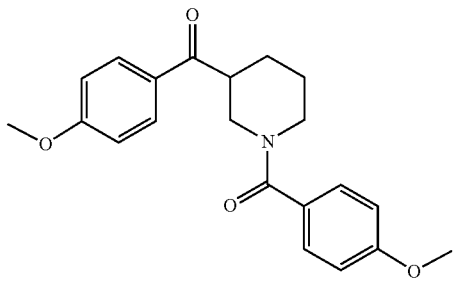

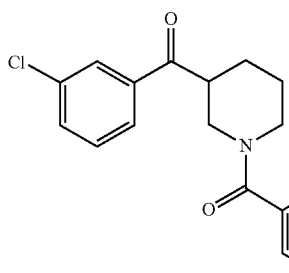

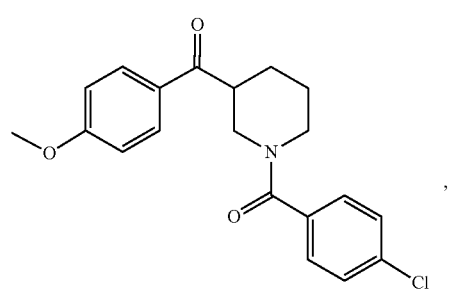

or a pharmaceutically acceptable salt thereof.

18. A method for treating an autoimmune disease, a lymphoma, or a T-cell leukemia in a patient, comprising administering to the patient the compound of claim 7, or the compound of formula:

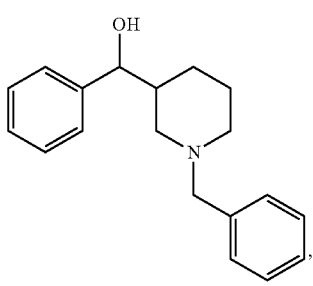

or a pharmaceutically acceptable salt thereof.

19. A method for treating an autoimmmune disease, a lymphoma, or a T-cell leukemia in a patient, comprising administering to the patient the compound of claim 12, or the compound of formula:

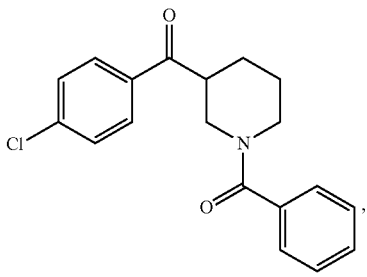

(V-4)

or a pharmaceutically acceptable salt thereof.

20. The method of claim 17, wherein the autoimmune disease is selected from the group consisting of: rheumatoid arthritis, vitiligo, autoimmune hepatitis, myasthenia gravis, ankylosing spondylitis, inflammatory bowel disease, Crohn's disease, ulcerative colitis, psoriatic arthritis, transplant rejection, psoriasis, type I diabetes, multiple sclerosis, systemic lupus erythematosus, asthma, uveitis and atopic dermatitis.

21. The method of claim 18, wherein the autoimmune disease is selected from the group consisting of: rheumatoid arthritis, vitiligo, autoimmune hepatitis, myasthenia gravis, ankylosing spondylitis, inflammatory bowel disease, Crohn's disease, ulcerative colitis, psoriatic arthritis, transplant rejection, psoriasis, type I diabetes, multiple sclerosis, systemic lupus erythematosus, asthma, uveitis and atopic dermatitis.

22. The method of claim 19, wherein the autoimmune disease is selected from the group consisting of: rheumatoid arthritis, vitiligo, autoimmune hepatitis, myasthenia gravis, ankylosing spondylitis, inflammatory bowel disease, Crohn's disease, ulcerative colitis, psoriatic arthritis, transplant rejection, psoriasis, type I diabetes, multiple sclerosis, systemic lupus erythematosus, asthma, uveitis and atopic dermatitis.

* * * * *